US008367696B2

(12) United States Patent
Nagashima et al.

(10) Patent No.: US 8,367,696 B2
(45) Date of Patent: Feb. 5, 2013

(54) AZA-BRIDGED-RING COMPOUND

(75) Inventors: Shinya Nagashima, Tokyo (JP); Toru Kontani, Tokyo (JP); Hiroshi Nagata, Tokyo (JP); Yuji Matsushima, Tokyo (JP); Hisao Hamaguchi, Tokyo (JP); Tadatsura Koshika, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 482 days.

(21) Appl. No.: 12/524,758

(22) PCT Filed: Feb. 8, 2008

(86) PCT No.: PCT/JP2008/052189
§ 371 (c)(1),
(2), (4) Date: Dec. 17, 2009

(87) PCT Pub. No.: WO2008/096870
PCT Pub. Date: Aug. 14, 2008

(65) Prior Publication Data
US 2010/0105658 A1    Apr. 29, 2010

(30) Foreign Application Priority Data

Feb. 9, 2007   (JP) .............................. P.2007-030963

(51) Int. Cl.
*A61K 31/439* (2006.01)
*C07D 221/00* (2006.01)
*C07D 221/02* (2006.01)
(52) U.S. Cl. ....................... 514/299; 546/112
(58) Field of Classification Search ........................ None
See application file for complete search history.

(56) References Cited

U.S. PATENT DOCUMENTS

| 6,916,828 | B2 | 7/2005 | Farrerons Gallemi et al. |
| 7,776,879 | B2 | 8/2010 | Buil Albero et al. |
| 7,879,874 | B2 | 2/2011 | Prat Quinones et al. |
| 2004/0266816 | A1 | 12/2004 | Buil Albero et al. |

FOREIGN PATENT DOCUMENTS

| EP | 0 747 355 | 12/1996 |
| JP | 08-198751 | 8/1996 |
| JP | 08198751 | * 8/1996 |
| JP | 2003-516391 | 5/2003 |
| JP | 2003-267977 | 9/2003 |
| JP | 2004-530641 | 10/2004 |
| RU | 2 282 629 | 1/2005 |
| RU | 2 296 762 | 4/2007 |
| UA | 72 632 | 4/2003 |
| WO | 95/06635 | 3/1995 |
| WO | 95/21820 | 8/1995 |
| WO | WO 97/30998 | 8/1997 |
| WO | 01/42213 | 6/2001 |
| WO | 02/051841 | 7/2002 |
| WO | 2004/000840 | 12/2003 |
| WO | 2004/012684 | 2/2004 |
| WO | 2004/048373 | 6/2004 |
| WO | 2005/087732 | 9/2005 |
| WO | 2006/005057 | 1/2006 |
| WO | 2007/007282 | 1/2007 |
| WO | 2008/041184 | 4/2008 |

OTHER PUBLICATIONS

Naruganahalli. Expert Opinion on Investigational Drugs, 2007, 16(7), 1127-1130.*
"Chronic Obstructive Pulmonary Disease (COPD)-Prevention", http://www.webmd.com/lung/copd/tc/chronic-obstructive-pulmonary-disease-copd-prevent., accessed Mar. 24, 2012.*
Gündisch, et al., "Synthesis and evaluation of phenylcarbamate derivatives as ligands for nicotine acetylcholine receptors", Bioorganic & Medicinal Chemistry, vol. 12 (2004) 4953-62.
Naito, et al., "Selective Muscarinic Antagonists. II. Synthesis and Antimuscarinic Properties of Biphenylylcarbamate Derivatives", Chem. Pharm. Bull., vol. 46, No. 8 (1998) 1286-94.
Fryer, et al., "Muscarinic Receptors and Control of Airway Smooth Muscle", Am. J. Respir. Crit. Care Med., vol. 158 (1998) S-154-60.
Pauwels, et al., "Global Strategy for the Diagnosis, Management, and Prevention of Chronic Obstructive Pulmonary Disease . . .", Am. J. Respir. Crit. Care Med., vol. 163 (2001) 1256-76.
Fryer, et al., "Effects of inflammatory cells on neuronal M2 Muscarinic receptor function in the lung", Life Sciences, vol. 64, Nos. 6/7 (1999) 449-55.
Caufield, "Muscarinic receptors—Characterization, Coupling and Function", Pharmac. Ther., vol. 58 (1993) 319-79.
Silverman, "The Organic Chemistry of Drug Design and Drug Action, 2d ed,", Elsevier Academic Press (2004) 25-34.

* cited by examiner

*Primary Examiner* — Noble Jarrell
(74) *Attorney, Agent, or Firm* — Fitzpatrick, Cella, Harper & Scinto

(57) ABSTRACT

[PROBLEMS] Provided is a compound which has an antagonistic action on a muscarinic $M_3$ receptor and is useful as an active ingredient of a prophylactic and/or therapeutic agent for an inflammatory disease such as a chronic obstructive pulmonary disease (COPD), asthma and the like.
[MEANS For SOLVING PROBLEMS] The present inventors have made studies on a compound having an antagonistic action on the binding of a muscarinic $M_3$ receptor, and they have found that an aza-bridged-ring compound or a salt thereof has an antagonistic action on the binding of a muscarinic $M_3$ receptor, thereby completing the present invention. The aza-bridged-ring compound of the present invention has an antagonistic action on the binding of a muscarinic $M_3$ receptor, and can be used as a prophylactic and/or therapeutic agent for an inflammatory disease such as a chronic obstructive pulmonary disease (COPD), asthma and the like.

6 Claims, No Drawings

AZA-BRIDGED-RING COMPOUND

TECHNICAL FIELD

The present invention relates to an aza-bridged-ring compound which is useful as an active ingredient of a pharmaceutical composition, particularly a pharmaceutical composition for treating an inflammatory disease.

BACKGROUND ART

Acetylcholine released from a cholinergic nerve in the peripheral and central nervous systems causes various biological reactions through binding with two types of acetylcholine receptors, a nicotinic receptor and a muscarinic receptor, respectively. Among these, the muscarinic receptor belongs to a seven-pass transmembrane-type G protein-conjugated receptor superfamily, and at the present time, there exist five subtypes of these receptors, $M_1$, $M_2$, $M_3$, $M_4$, and $M_5$, which are each encoded by different gene sequences. These five types of the receptors are widely distributed in each tissue of a vertebrate body. The muscarinic receptor is known to have both the excitatory and inhibitory actions, depending on its subtype. Specifically, the functional roles of various muscarinic receptors, for example, a contribution of the $M_3$ receptor present in the airway smooth muscle to contraction reactions of the smooth muscle, or other roles, have been reported in General Overview of Caulfield, et al. (Non-Patent Document 1).

In the lung, the muscarinic receptor is present in the tracheal and bronchial smooth muscles, the submucosal glands, and the parasympathetic ganglion. It has been known that the distribution density of the muscarinic receptors is highest in the parasympathetic ganglion, and then in the submucosal glands and the tracheal smooth muscle in this order, and is lowest in the bronchial smooth muscle (Non-Patent Document 2).

As the muscarinic receptor which plays an important role in the lung tissue, three types of $M_1$, $M_2$, and $M_3$ may be mentioned. The $M_3$ receptor which is present in the airway smooth muscle is involved in the smooth muscle contraction, which causes airway obstruction. If the $M_3$ receptor is activated, a phospholipase C in the cytoplasm is activated through the activation of the stimulatory G protein, subsequently phosphatidylinositol 3-phosphate is dissociated into phosphatidylinositol 4,5-diphosphate, and finally a contractile protein is phosphorylated. The $M_3$ receptor is present in the submucosal glands, in addition to in the smooth muscle which is present in the lung tissue. If this type of $M_3$ receptor is activated the mucus is secreted.

The $M_2$ receptors constitute about 50 to 80% of the cholinergic receptors which are present in the airway smooth muscle. Details on the role of this subtype of the receptor are still unclear, but the reduction of the amount of the cAMP's produced in the cytoplasm is believed to inhibit the relaxation of the airway smooth muscle due to the sympathetic innervation. The central $M_2$ receptors are distributed in the postganglionic parasympathetic fibers. Under physiological conditions, the central $M_2$ receptor plays a role in the negative regulation of the release of acetylcholine from the parasympathetic. The $M_2$ receptor which is expressed in the cardiac muscle is due to regulation of the chronotropic action. The $M_1$ receptor is found in the parasympathetic ganglion of the lung tissue, and functions to facilitate neurotransmission. The $M_1$ receptors are distributed not only in the ganglion, but also in the peripheral lung parenchymal tissue, but their function is unclear.

In the lung tissues, the abnormal function of the muscarinic receptor is perceived when a large number of pathologic conditions are formed. Particularly, for an inflammatory disease such as a chronic obstructive pulmonary disease (COPD), asthma and the like, a sustained inflammatory response leads to dysfunction of an inhibitory $M_2$ receptor which is present in a parasympathetic nerve, and increases the release of acetylcholine by vagus nerve stimulation (Non-Patent Document 3). Therefore, the dysfunction of this receptor causes the relative preference of the $M_3$ receptor-mediated function, which leads to the induction of airway hyperreactivity. Therefore, a drug that selectively antagonizes the $M_3$ receptor-mediated function without interfering with the $M_2$ receptor-mediated function is thought to be an effective therapeutic agent.

COPD shows a limit in the airflow, usually by an organic change based on the persistent inflammation in the peripheral airways and primarily, the alveoli, allowing the symptoms of coughing, sputum, breathlessness and the like to be perceived, occupies the fourth leading cause of death as of the year 2005, and is a major cause of death world-wide. Further, by the year 2020, it is expected to be the third leading cause of death. Smoking is a major risk factor of COPD, and recently, in addition to this, air pollution or the like due to dust is also mentioned as a risk factor among other issues. The medical cost required for COPD treatment is very high, and the number of patients is expected to increase in future.

A therapy with an inhaled anticholinergic agent is regarded as a drug firstly chosen for the above-described diseases (Non-Patent Document 4), and in recent years, in each region in the Western countries and Asia, a long-term operating (once a day) anticholinergic agent, tiotropium bromide (Spiriva (registered trademark)), has been launched on the market. However, by taking into account the status of treatment, none of the conventional anticholinergic agents including Spiriva (registered trademark) are complete from the viewpoints of either convenience or safety, and thus, there is a room for improvement at present. Therefore, there is a strong desire to create an oral or inhaled anticholinergic agent which is improved in any of the above-described viewpoints.

For example, there has been known a carbamate compound which has an $M_3$ receptor antagonistic action and has an airway contraction inhibitory action, wherein the Ring A of the following formula is an unsubstituted benzene or an unsubstituted pyridine (Patent Document 1). In this Patent Document, the compound of the present invention is not disclosed or suggested.

[Chem. 1]

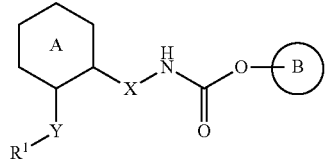

[for the symbols in the formula, refer to this publication]

Further, there has been known a carbamate compound as below, which has an $M_3$ receptor antagonistic action and has an airway contraction inhibitory action (Patent Document 2). However, in this Patent Document, the compound of the present invention is not disclosed or suggested.

[Chem. 2]

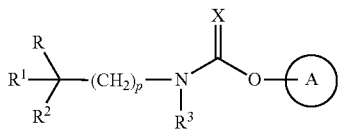

[for the symbols in the formula, refer to this publication]
[Patent Document 1] Pamphlet of International Publication No. WO 95/21820
[Patent Document 2] Pamphlet of International Publication No. WO WO95/06635
[Non-Patent Document 1] Pharmacology and Therapeutics, 1993, vol. 58, pp. 319-379
[Non-Patent Document 2] American Journal Respiratory and Critical Care Medicine, 1998, 158, pp. 154S-160S
[Non-Patent Document 3] Life Science, 1999, vol. 64 (6-7), pp. 449-455
[Non-Patent Document 4] American Journal Respiratory and Critical Care Medicine, 2001, 163, pp. 1256-1276

DISCLOSURE OF THE INVENTION

Problem that the Invention is to Solve

Provided is a compound which is useful as an active ingredient of a pharmaceutical composition, particularly, a pharmaceutical composition for treating an inflammatory disease such as a chronic obstructive pulmonary disease (COPD), asthma and the like.

Means for Solving the Problem

The present inventors have made extensive studies on a compound having an antagonistic action on a muscarinic $M_3$ receptor, and as a result, they have found that an aza-bridged-ring compound is useful for an antagonistic action on a muscarinic $M_3$ receptor, thereby completing the present invention.

Specifically, the present invention relates to a compound of the formula (I) or a salt thereof, and a pharmaceutical composition comprising the compound of the formula (I) or a salt thereof, and an excipient.

[Chem. 3]

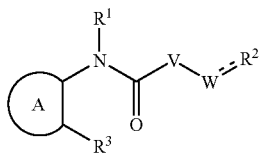

(I)

[$R^1$ is —H or $C_{1-6}$ alkyl;
$R^2$ is an aza-bridged-ring selected from the group consisting of the formulae (a), (b), (c), and (d):

[Chem. 4]

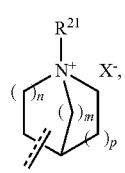

(a)

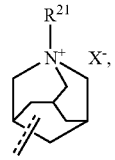

(b)

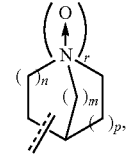

(c)

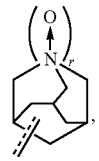

(d)

wherein the ring carbon in the aza-bridged-ring may be substituted with one or more $R^{22}$;
m, n, and p are respectively 1 or 2;
r is 0 or 1;
$R^{21}$ is $C_{1-6}$ alkyl, —$C_{1-6}$ alkyl-O-aryl, or —$C_{1-6}$ alkyl-aryl;
$R^{22}$ is —$C_{1-6}$ alkyl-cycloalkyl or —$C_{1-6}$ alkyl-aryl;
$R^3$ is thienyl, phenyl, pyridyl, pyrazinyl, thiazolyl, or pyrazolyl,
each of which may be substituted with one or more $R^{31}$;
in which $R^{31}$ is halogen, —OH, —CN, —$CF_3$, $C_{1-6}$ alkyl or —O—$C_{1-6}$ alkyl;
Ring A is an aromatic hydrocarbon ring, a hetero ring, or cycloalkane,
each of which may be substituted with $R^4$;
in which $R^4$ is halogen, —CN, —$NH_2$, $C_{1-6}$ alkyl, —O—$C_{1-6}$ alkyl, —$CONH_2$, —NH—$C_{1-6}$ alkyl, —NH—$C_{1-6}$ alkyl-O—$C_{1-6}$ alkyl-aryl, —NH—$C_{1-6}$ alkyl-aryl, or —NH—$C_{1-6}$ alkyl-OH,
in which $C_{1-6}$ alkyl may be substituted with one or more halogen;
V is —NH— or —O—;
W is —$(CH_2)_q$— or —$(CH_2)_s$—CH=;
q is 0, 1, or 2;
s is 1 or 2;
$X^-$ is a counter anion; and
⋯ is a single bond or a double bond;
provided that in the case where Ring A is a substituted benzene, $R^3$ is phenyl, pyridyl, pyrazinyl, thiazolyl, or pyrazolyl, each of which may be substituted with one or more $R^{31}$, and;
in the case where Ring A is an unsubstituted benzene, q is 1 or 2; and
in the case where the Ring A is cycloalkane, $R^3$ is phenyl which may be substituted with one or more $R^{31}$].

Furthermore, unless specified otherwise, in the case where the symbols in any of the formulae in the present specification are also used in other formulae, the same symbols denote the same meanings.

The present invention relates to a pharmaceutical composition for treating an inflammatory disease such as a chronic obstructive pulmonary disease (COPD), asthma and the like, which comprises a compound of the formula (I) or a salt thereof, that is, a therapeutic agent for an inflammatory disease such as a chronic obstructive pulmonary disease (COPD), asthma and the like, which comprises the compound of the formula (I) or a salt thereof.

Further, the present invention relates to use of the compound of the formula (I) or a salt thereof for the preparation of a pharmaceutical composition for treating an inflammatory disease such as a chronic obstructive pulmonary disease (COPD), asthma and the like, and to a method for treating an inflammatory disease such as a chronic obstructive pulmonary disease (COPD), asthma and the like, which comprises administering to a patient an effective amount of the compound of the formula (I) or a salt thereof.

Effect of the Invention

The compound of the formula (I) or a salt thereof has an antagonistic action on the binding of a muscarinic $M_3$ receptor, and can be therefore used as a prophylactic and/or therapeutic agent for an inflammatory disease such as a chronic obstructive pulmonary disease (COPD), asthma and the like.

BEST MODE FOR CARRYING OUT THE INVENTION

Hereinbelow, the present invention will be described in detail.

In the present specification, the "halogen" refers to F, Cl, Br, or I.

In the present specification, the "$C_{1-6}$ alkyl" refers to linear or branched alkyl having 1 to 6 carbon atoms, for example, methyl, ethyl, n-propyl, isopropyl, n-butyl, isobutyl, sec-butyl, tert-butyl, n-pentyl, n-hexyl or the like. In a further embodiment, it is $C_{1-4}$ alkyl. In an even further embodiment, it is methyl, ethyl, or isopropyl.

In the present specification, the "—$C_{1-6}$ alkyl-" refers to, in cases where it has a prefix and a suffix with hyphens, linear or branched $C_{1-6}$ alkylene, for example, methylene, ethylene, trimethylene, tetramethylene, pentamethylene, hexamethylene, propylene, methylmethylene, ethylethylene, 1,2-dimethylethylene, 1,1,2,2-tetramethylethylene or the like. In a further embodiment, it is $C_{1-4}$ alkylene, and in an even further embodiment, methylene, ethylene, or trimethylene.

In the present specification, the "aromatic hydrocarbon ring" means an aromatic hydrocarbon ring having 6 to 14 carbon atoms. In an embodiment, examples thereof include benzene, naphthalene and the like, and in a further embodiment, benzene.

In the present specification, the "hetero ring" means a 5- to 6-membered aromatic hetero ring containing one or more hetero atoms which are the same as or different from each other, selected from the group consisting of nitrogen, oxygen, and sulfur, which may be condensed with a cycloalkyl ring or a benzene ring. Specifically, examples thereof include pyridine, pyrazine, pyrimidine, pyridazine, pyrazole, imidazole, oxalzole, thiazole, thiophene, furan, oxadiazole, isothiazole, isooxazole, thiadiazole, quinoline, isoquinoline, benzothiazole, benzothiophene, benzoxazole, indole, indazole, cyclopentathiophene and the like. In a further embodiment, the hetero ring is a 5-membered hetero ring, and in an even further embodiment, examples thereof include oxazole, thiophene, thiazole, thiadiazole, and cyclopentathiophene. In an even further embodiment, examples thereof include thiophene and thiazole.

In the present specification, the "cycloalkane" means a $C_{3-9}$ non-aromatic carbon ring, which may have a partially unsaturated bond, and may be condensed with a benzene ring. Further, it comprises a bridged ring. Accordingly, specific examples thereof include cyclopropane, cyclobutane, cyclohexane, cycloheptane, cyclooctane, cyclobutene, cyclohexene, cyclooctadiene, norborane, bornene, indane, tetrahydronaphthalene and the like, and in a further embodiment, cyclohexane.

Further, examples of the counter anion of the "$X^-$" include a halide ion, trifluoromethanesulfonate, p-toluenesulfonate, methanesulfonate and the like, and in a further embodiment, it is preferably a halide ion (for example, a chloride ion, a bromide ion, and an iodide ion), but it is not limited thereto. Further, in a further embodiment, examples thereof further include inorganic anions such as a nitric acid ion, a phosphoric acid ion, a carbonic acid ion and the like, carboxylates such as formate ($HCOO^-$), acetate ($CH_3COO^-$), propionate, oxalate and the like, and anions of amino acids such as glutamic acid and the like.

The "anion exchanger" refers to a different compound of the "$X^-$".

In the present specification, the expression "may be substituted" means that it is unsubstituted, or it has 1 to 5 substituents. Furthermore, in the case of having a plurality of substituents, the substituents may be the same as or different from each other.

In the present specification, the substituent, for which the expressions "may be substituted" or "be substituted" are acceptable, can be any substituent which is usually used as a substituent for each group.

For example, examples of the substituent in the Ring A, for which the expressions "may be substituted" or "be substituted" are acceptable, include halogen, —CN, —$NH_2$, $C_{1-6}$ alkyl, —O—$C_{1-6}$ alkyl, —$CONH_2$, —NH—$C_{1-6}$ alkyl, —NH—$C_{1-6}$ alkyl-O—$C_{1-6}$ alkyl-aryl, —NH—$C_{1-6}$ alkyl-aryl, and —NH—$C_{1-6}$ alkyl-OH.

An embodiment [1] according to the present invention is as follows. Regarding the formula (I), (1) the compound, wherein $R^1$ is —H, (2) the compound, wherein $R^2$ is an aza-bridged-ring selected from the group consisting of the formulae (a), (b), (c), and (d):

[Chem. 5]

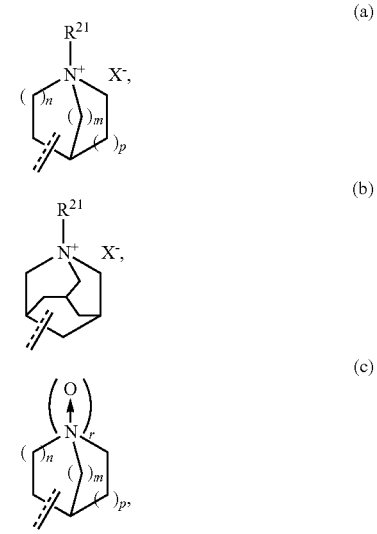

(d)

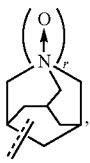

(3) the compound, wherein r is 0,
(4) the compound, wherein X is halogen,
(5) the compound, wherein $R^3$ is phenyl which may be substituted with one or more $R^{31}$, and
$R^{31}$ is halogen, —OH, —CN, —CF$_3$, —C$_{1-6}$ alkyl, or —O—C$_{1-6}$ alkyl,
(6) the compound, wherein Ring A is a hetero ring or cycloalkyl,
each of which may be substituted with a group selected from the group consisting of one or more $R^A$,
(7) the compound, wherein V is —O—,
(8) the compound, wherein W is —(CH$_2$)$_q$— and q is 0 or 1,
(9) the compound, wherein ═ is a single bond,
(10) the compound, wherein m, n, and p are respectively 1 or 2, and
(11) the compound which is a combination of two or more of (1) to (10) as above, or a salt thereof.

Another embodiment [2] of the present invention is as follows.
The compound or a salt thereof of the embodiment [1], wherein
Ring A is a hetero ring or cycloalkane,
each of which may be substituted with a group selected from the group consisting of one or more $R^{A1}$;
in which $R^{A1}$ is halogen, —CN, —NH$_2$, C$_{1-6}$ alkyl, —O—C$_{1-6}$ alkyl, —CONH$_2$, —NH—C$_{1-6}$ alkyl, —NH—C$_{1-6}$ alkyl-O—C$_{1-6}$ alkyl-phenyl, —NH—C$_{1-6}$ alkyl-phenyl, or —NH—C$_{1-6}$ alkyl-OH,
in which C$_{1-6}$ alkyl may be substituted with halogen.

Another embodiment [3] of the present invention is as follows.
The compound or a salt thereof of the embodiment [2], wherein
Ring A is a group selected from the group consisting of thiophene, thiazole, isothiazole, thiadiazole, oxazole, isooxazole, cyclohexane, norborane, benzothiophene, and 5,6-dihydro-4H-cyclopentathiophene, each of which may be substituted with a group selected from the group consisting of one or more $R^{A1}$.

Another embodiment [4] of the present invention is as follows.
The compound or a salt thereof of the embodiment [3], wherein
Ring A is a group selected from the group consisting of thiophene, thiazole, and cyclohexane,
each of which may be substituted with a group selected from the group consisting of one or more $R^{A1}$.

Another embodiment [5] of the present invention is as follows.
The compound or a salt thereof of the embodiment [4], wherein
$R^1$ is —H.

Another embodiment [6] of the present invention is as follows.
The compound or a salt thereof of the embodiment [5], wherein $R^3$ is phenyl which may be substituted with one or more $R^{31}$,
and $R^{31}$ is halogen, —OH, —CN, —CF$_3$, —C$_{1-6}$ alkyl, or —O—C$_{1-6}$ alkyl.

Another embodiment [7] of the present invention is as follows.
The compound or a salt thereof of the embodiment [6], wherein
$R^2$ is an aza-bridged-ring selected from the group consisting of the formulae (a), (b), (c), and (d), in which in case of (a) or (c), (m, n, p) is (2, 1, 1), (1, 1, 2), or (2, 1, 2) for each sequence.

Another embodiment [8] of the present invention is as follows.
The compound or a salt thereof of the embodiment [7], wherein
$R^2$ is an aza-bridged-ring selected from the group consisting of the formulae (a) and (b), and
$R^{21}$ is C$_{1-6}$ alkyl, —C$_{1-6}$ alkyl-O-phenyl, or —C$_{1-6}$ alkyl-phenyl.

Examples of the specific compounds included in the present invention include the following compounds or free bases thereof
(1) 1-azabicyclo[2.2.2]oct-4-ylmethyl(5-phenyl-1,3-thiazol-4-yl)carbamate hydrochloride,
(2) 1-azabicyclo[3.2.2]non-5-yl(5-phenyl-1,3-thiazol-4-yl)carbamate hydrochloride,
(3) (3R)-1-azabicyclo[2.2.2]oct-3-yl[(1R,2S)-2-phenylcyclohexyl]carbamate hydrochloride,
(4) 1-azatricyclo[3.3.1.1-3,7-]dec-4-yl(5-phenyl-1,3-thiazol-4-yl)carbamate hydrochloride,
(5) 1-azabicyclo[2.2.2]oct-3-ylmethyl(2-phenyl-3-thienyl)carbamate hydrochloride,
(6) 1-azabicyclo[2.2.2]oct-4-yl[5-(4-fluorophenyl)-1,3-thiazol-4-yl]carbamate hydrochloride,
(7) 1-azabicyclo[3.2.1]oct-6-ylmethyl(5-phenyl-1,3-thiazol-4-yl)carbamate hydrochloride, or
(8) 1-azabicyclo[2.2.2]oct-3-ylmethyl[5-(4-fluorophenyl)-1,3-thiazol-4-yl]carbamate fumarate.

Examples of the specific compounds included in the present invention include the following compounds or anion exchangers thereof
(1) 4-({[5-(3-chlorophenyl)-1,3-thiazol-4-yl]carbamoyl}oxy)-1-methyl-1-azoniabicyclo[2.2.2]octane iodide,
(2) 1-(3-phenylpropyl)-3-({[(2-phenyl-3-thienyl)carbamoyl]oxy}methyl)-1-azoniabicyclo[2.2.2]octane bromide,
(3) 1-(2-phenylethyl)-4-{[(5-phenyl-1,3-thiazol-4-yl)carbamoyl]oxy}-1-azoniabicyclo[2.2.2]octane bromide,
(4) 1-(2-phenoxyethyl)-4-{[(5-phenyl-1,3-thiazol-4-yl)carbamoyl]oxy}-1-azoniabicyclo[2.2.2]octane bromide,
(5) 4-({[5-(2,5-difluorophenyl)-1,3-thiazol-4-yl]carbamoyl}oxy)-1-methyl-1-azoniabicyclo[2.2.2]octane iodide,
(6) 1-methyl-5-{[(5-phenyl-1,3-thiazol-4-yl)carbamoyl]oxy}-1-azoniabicyclo[3.2.2]nonane iodide,
(7) 4-({[5-(3-chlorophenyl)-1,3-thiazol-4-yl]carbamoyl}oxy)-1-(2-phenoxyethyl)-1-azoniabicyclo[2.2.2]octane iodide,
(8) 4-({[5-(3-chlorophenyl)-1,3-thiazol-4-yl]carbamoyl}oxy)-1-methyl-1-azoniabicyclo[2.2.2]octane bromide,
(9) 4-({[5-(3,5-dichlorophenyl)-1,3-thiazol-4-yl]carbamoyl}oxy)-1-methyl-1-azoniabicyclo[2.2.2]octane iodide,

(10) 4-({[5-(2,5-difluorophenyl)-1,3-thiazol-4-yl]carbamoyl}oxy)-1-methyl-1-azoniabicyclo[2.2.2]octane bromide,
(11) 4-({[5-(2,4-difluorophenyl)-1,3-thiazol-4-yl]carbamoyl}oxy)-1-methyl-1-azoniabicyclo[2.2.2]octane bromide,
(12) 1-methyl-4-{[(5-phenyl-1,3-thiazol-4-yl)carbamoyl]oxy}-1-azoniabicyclo[2.2.2]octane bromide,
(13) 4-({[5-(3,5-dichlorophenyl)-1,3-thiazol-4-yl]carbamoyl}oxy)-1-methyl-1-azoniabicyclo[2.2.2]octane bromide, or
(14) 1-methyl-5-{[(5-phenyl-1,3-thiazol-4-yl)carbamoyl]oxy}-1-azoniabicyclo [3.2.2]nonane bromide.

The compound of the formula (I) may exist in the form of geometrical isomers depending on the kinds of the substituents. In the present specification, the compound of the formula (I) may be described in only one form of an isomer, but the present invention includes other isomers, isolated forms of the isomers, or a mixture thereof.

Further, the compound of the formula (I) may have an asymmetric carbon atom, and correspondingly, may exist in the form of optical isomers. The present invention includes an isolated form of these optical isomers of the compound of the formula (I), or a mixture thereof.

Furthermore, the present invention also includes a pharmaceutically acceptable prodrug of the compound of the formula (I). The pharmaceutically acceptable prodrug refers to a compound having a group which can be converted into an amino group, a hydroxyl group, a carboxyl group and the like by solvolysis or under physiological conditions. Examples of the group to form a prodrug include the groups as described in "Prog. Med., 5, 2157-2161 (1985)", or "Iyakuhin no Kaihatsu (Development of Medicines) (Hirokawa Shoten, 1990), vol. 7, Bunshi Sekkei (Molecular Design)", 163-198.

Moreover, the salt of the compound of the formula (I) refers to a pharmaceutically acceptable salt of the compound of the formula (I), and in some cases, it forms an acid addition salt or a salt with a base, depending on the kind of substituents. Specifically, examples thereof include acid addition salts with inorganic acids such as hydrochloric acid, hydrobromic acid, hydroiodic acid, sulfuric acid, nitric acid, phosphoric acid and the like, and with organic acids such as formic acid, acetic acid, propionic acid, oxalic acid, malonic acid, succinic acid, fumaric acid, maleic acid, lactic acid, malic acid, mandelic acid, tartaric acid, dibenzoyl tartaric acid, ditoluoyl tartaric acid, citric acid, methanesulfonic acid, ethanesulfonic acid, benznesulfonic acid, p-toluenesulfonic acid, asparaginic acid, glutamic acid and the like, and salts with various amino acids and amino acid derivatives such as acetylleucine and the like.

Furthermore, the present invention also includes various hydrates or solvates, and polymorphic crystal substances of the compound of the formula (I) and a salt thereof. Also, the present invention includes the compounds labeled with various radioactive or non-radioactive isotopes.

The abbreviations in the present specification are as follows.

BINAP: (R)-(+)- or (S)-(−)-2,2'-bis(diphenylphosphino)-1,1'-binaphthyl
$CHCl_3$: chloroform
$Cs_2CO_3$: cesium carbonate
$CuCl_2$: copper chloride
DCE: 1,2-dichloroethane
DCM: dichloromethane
DEAD: diethyl azodicarboxylate
DIBOC: di-tert-butyldicarbonate
DIPA: diisopropylamine
DIPEA: N,N-diisopropylethylamine
DMA: dimethylacetamide
DMAP: N,N-dimethyl-4-aminopyridine
DMF: N,N-dimethylformamide
DMSO: dimethylsulfoxide
DPPA: diphenylphosphoric acid azide
DPPF: diphenylphosphinoferrocene
EtOAc: ethyl acetate
EtOH: ethanol
HCl/dioxane: hydrogen chloride/dioxane solution
HCl/EtOAc: hydrogen chloride/ethyl acetate solution
HCl/MeOH: hydrogen chloride/methanol solution
IPE: diisopropylether
$K_2CO_3$: potassium carbonate
KOH: potassium hydroxide
LAH: lithium aluminum hydride
$LiBH_4$: lithium borohydroxide
MCPBA: methachlor-perbenzoic acid
MEK: 2-butanone
MeCN: acetonitrile
MeOH: methanol
$MgSO_4$: anhydrous magnesium sulfate
NBS: N-bromosuccinimide
NCS: N-chlorosuccinimide
NMP: N-methylpyrrolidone
$Na_2CO_3$: sodium carbonate
$Na_2SO_4$: anhydrous sodium sulfate
$Na_2SO_4 \cdot 10H_2O$: sodium sulfate decaanhydride
NaH: sodium hydride
$NaHCO_3$: sodium hydrogen carbonate
NaOAc: sodium acetate
$NaOBu^t$: sodium tertiary butoxide
NaOEt: sodium ethoxide
NaOH: sodium hydroxide
NaOMe: sodium methoxide
$P(Bu^t)_3$: tri(tertiary butyl) phosphine
$PPh_3$: triphenylphosphine
$Pd(OAc)_2$: palladium acetate
$PdCl_2(PPh_3)_2$: dichlorobistriphenylphosphinepalladium
$Pd_2dba_3$: tris(dibenzylideneacetone)dipalladium
$Pd(PPh_3)_4$: tetrakis(triphenylphosphine)palladium (0)
rel: relative configuration
Rt: retention time
TEA: triethylamine
TFA: trifluoroacetic acid
THF: tetrahydrofuran
brine: saturated physiological saline
tBuOH: tertiary butanol
tBuOK: potassium tertiary butoxide (Preparation Methods)

The compound of the formula (I) and a salt thereof can be prepared by applying various known synthetic methods, by the use of the characteristics based on their basic skeletons or the kinds of substituents. At this time, depending on the kinds of functional groups, it is in some cases effective from the viewpoint of the preparation techniques to substitute the functional group with an appropriate protecting group (a group which is easily capable of being converted into the functional group), during the steps from starting materials to intermediates. Examples of such a functional group include the protecting groups as described in "Greene's Protective Groups in Organic Synthesis (4$^{th}$ Edition, 2006)", edited by P. G. M. Wuts and T. W. Greene, which may be appropriately selected and used depending on the reaction conditions. In these methods, a desired compound can be obtained by introducing the protecting group to carry out the reaction, and then, if desired, removing the protecting group.

In addition, a prodrug of the compound of the formula (I) can be prepared by introducing a specific group during the steps from the starting materials to the intermediates, in a similar manner to the aforementioned protecting groups, or by further carrying out a reaction using the resulting compound of the formula (I). The reaction may be carried out by employing a method conventionally known to a person skilled in the art, such as common esterification, amidation, dehydration and the like.

Hereinbelow, representative preparation methods for the compound of the formula (I) are described. Further, the preparation methods of the present invention are not limited to examples shown below.

<Production Process 1>

[Chem. 6]

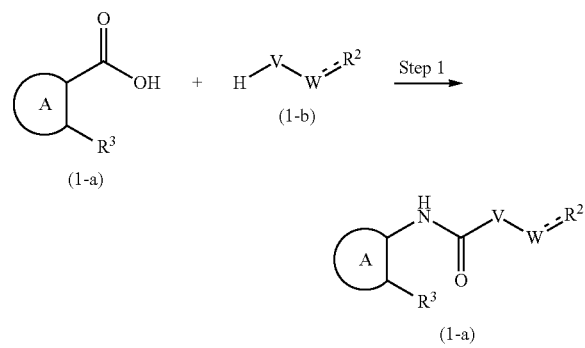

This production process is a process for preparing the compound of the formula (I-a) with $R^1$=H from the compound (1-a).

The step of Step 1 is a reaction for allowing a carboxyl group of the compound (1-a) to undergo a reaction with an azidation agent such as DPPA, sodium azide and the like to constitute a carbamate group or an urea group by a so-called Curtius rearrangement reaction, which is preferably carried out in the presence of a base. As the base, TEA, pyridine or the like can be usually used, and the reaction can be carried out at room temperature, at a room temperature to under heating, or under heating under reflux. Further, the preparation can also be conducted by a process via an isocyanate that is yielded from a carboxylic acid derivative, which uses hydrazoic acid in the presence of concentrated sulfuric acid.

<Production Process 2>

[Chem. 7]

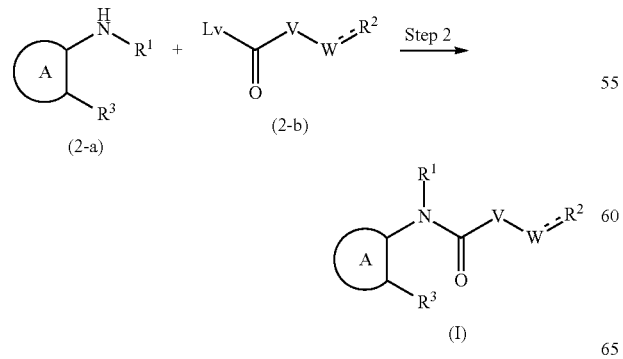

[wherein Lv represents a leaving group].

This production process is a process for preparing the compound of the formula (I) using a compound (2-a) as a starting material.

Step 2 is a reaction for allowing the compound (2-a) to undergo a reaction with a compound (2-b), which is preferably carried out in the presence of a base. As the base, TEA, pyridine or the like can be usually used, and the reaction can be carried out at room temperature, at room temperature to under heating, or under heating under reflux. Here, examples of the leaving group include halogen; methanesulfonyloxy, ethanesulfonyloxy, benzenesulfonyloxy, p-toluenesulfonyloxy, trifluoromethanesulfonyloxy; and the like.

<Production Process 3>

[Chem. 8]

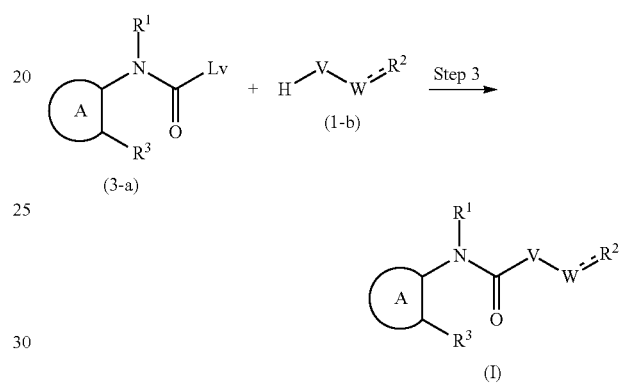

This production process is a process for preparing the compound of the formula (I) from a compound (3-a).

The step of Step 3 is a reaction for allowing the compound (3-a) to undergo a reaction with the compound (1-b), which is preferably carried out in the presence of a base (for example, NaH, NaOMe, NaOEt, NaOH, KOH and the like) to promote the reaction. Here, examples of the leaving group, Lv, include halogen, methoxy, ethoxy, phenoxy, p-nitrophenoxy and the like.

<Production Process 4>

[Chem. 9]

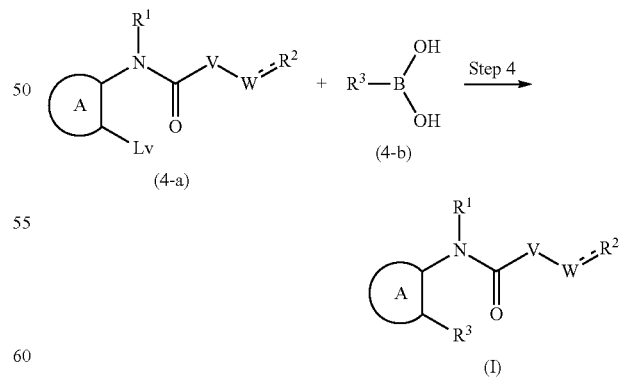

This reaction is a process for preparing the compound of the formula (I) by reacting a halogenated aryl compound (4-a) with an aryl boric acid compound (4-b), and using a so-called Suzuki coupling. The reaction can be carried out without a solvent, or in a solvent which is inert to the reaction, such as aromatic hydrocarbons (for example, benzene, toluene, xylene and the like), ethers (for example, THF, dioxane and the like); halogenated hydrocarbons (for example, DCM, DCE, CHCl$_3$ and the like); DMF, DMA, NMP; EtOAc, MeCN and the like, at room temperature to under heating under reflux. The reaction is carried out in the coexistence of palladium, phosphine ligands, and metal bases. As palladium, a divalent palladium such as Pd(OAc)$_2$ and the like, or a null-valent palladium such as Pd$_2$ dba$_3$ and the like can be used. As the phosphine ligand, a bidentate ligand such as BINAP, DPPF and the like, a monodentate ligand such as P(Bu$^t$)$_3$ and the like can be used. As the metal base, K$_2$CO$_3$, Cs$_2$CO$_3$, potassium phosphate, NaOBu$^t$ and the like can be used. Here, examples of the leaving group, Lv, include halogen, trifluoromethanesulfonyloxy and the like.

<Production Process 5>

[Chem. 10]

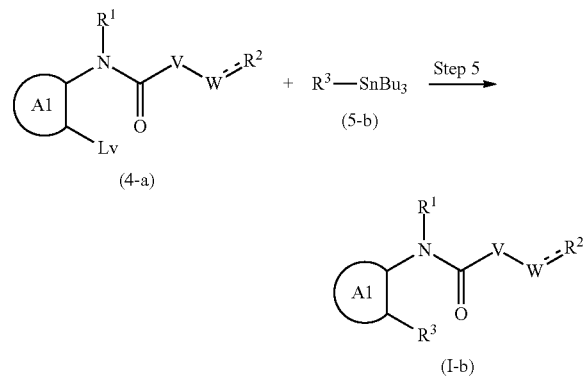

[wherein A1 represents aromatic hydrocarbon or a hetero ring].

This reaction is a process for preparing the compound of the formula (I-b) by reacting a compound (4-a) with a tin compound (5-b), and using a so-called Stille coupling. The reaction can be carried out without a solvent, or in a solvent which is inert to the reaction, such as aromatic hydrocarbons (for example, benzene, toluene, xylene and the like), ethers (for example, THF, dioxane and the like); halogenated hydrocarbons (for example, DCM, DCE, CHCl$_3$ and the like); DMF, DMA, NMP; EtOAc, MeCN and the like, at room temperature to under heating under reflux. The reaction is carried out in the coexistence of palladium, and phosphine ligands. As palladium, a divalent palladium such as Pd(OAc)$_2$ and the like, or a null-valent palladium such as Pd$_2$ dba$_3$ and the like can be used. As the phosphine ligand, a bidentate ligand such as BINAP, DPPF and the like, a monodentate ligand such as P(Bu$^t$)$_3$ and the like can be used. Here, examples of the leaving group include halogen, trifluoromethanesulfonyloxy and the like.

<Production Process 6>

[Chem. 11]

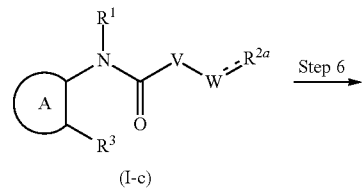

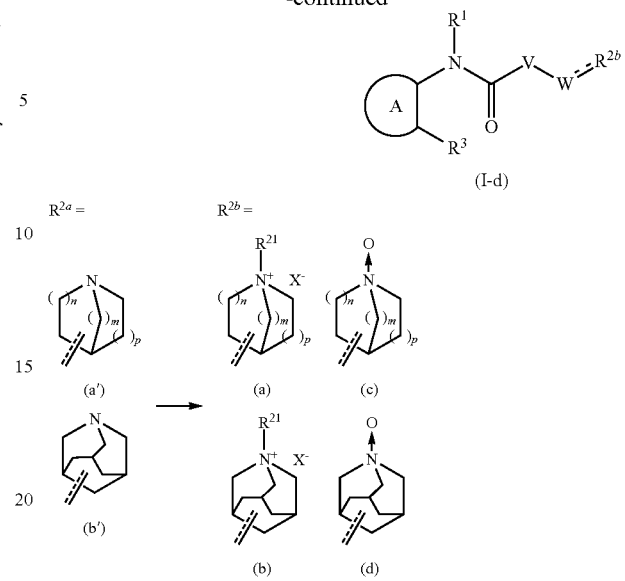

In the compound of the formula (I), the compounds (a, b) in which a nitrogen atom of the aza-bridged-ring group forms a quaternary ammonium salt, or the compounds (c, d) in which said nitrogen atom is oxidized can be prepared by subjecting a tertiary amine compound (1-c) of the present invention compound to an N-alkylation or N-oxidation reaction, which can be usually carried out in the final step.

The N-alkylation reaction can be carried out by a conventional method for an N-alkylation reaction, but specifically, it can be carried out by stirring a tertiary amine compound of the present invention with a corresponding amount of an alkylation agent in an inert solvent such as DMF, CHCl$_3$, acetone, MEK, MeCN, THF and the like, from under ice-cooling to at room temperature, or in some cases, with heating under reflux.

Examples of the alkylation agent include alkyl halide, C$_{1-6}$ alkyl trifluoromethanesulfonate, C$_{1-6}$ alkyl p-toluenesulfonate, C$_{1-6}$ alkylmethanesulfonate and the like.

The N-oxidation reaction can be carried out by a conventional method for an oxidization reaction, but specifically, it can be carried out by stirring a tertiary amine compound of the present invention with a corresponding amount or excessive amount of an oxidant in an inert solvent such as CHCl$_3$, DCM, DCE and the like, alcohols such as MeOH, EtOH and the like, water, or a mixed solvent thereof, from under cooling to at room temperature, or in some cases, with heating under reflux. Examples of the oxidant include an organic peracid such as MCPBA and the like, sodium periodide, hydrogen peroxide and the like.

<Production Process 1 for Intermediate>

[Chem. 12]

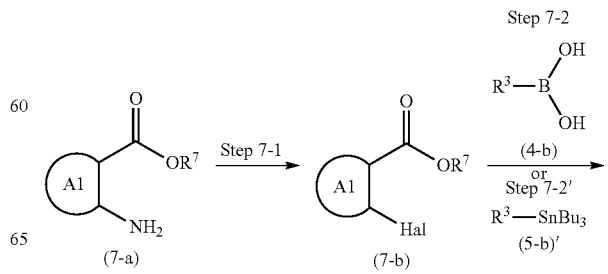

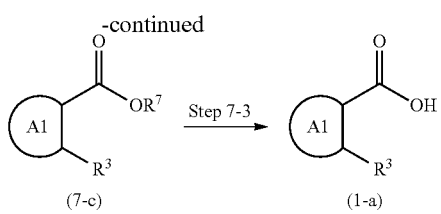

[wherein Hal represents halogen and $R^7$ represents a protecting group of a carboxylic acid].

The compound (1-a) of Step 1 can be prepared in the following process.

Step 7-1 is a process for preparing a compound (7-b) by using compound (7-a) as a starting material. Halogenated aryl can be prepared by allowing an alkali metal salt of a nitric acid or nitric esters to undergo a reaction with the compound (7-a) under an acidic condition to produce a diazonium salt of an aryl amino compound, and adding it to a solution containing hydrogen halide in the presence of a cuprite catalyst. The reaction can be carried out in a solvent such as sulfuric acid, acetic acid, phosphoric acid, acetone, MeCN, DMSO and the like. As the halogenation agent, halogenated copper or halogenated iron can be used, and as the cuprite, $CuCl_2$ or $CuBr_2$ can be used. Regarding the reaction temperature, the reaction can be carried out under ice-cooling to at room temperature, or at room temperature to under a reflux condition.

The steps of Step 7-2 and Step 7-2' can be carried out by the same method as the Fourth or Production Process 5 above.

Step 7-3 is a reaction for obtaining a carboxylic acid by subjecting an ester group to hydrolysis or deprotection, for which the condition for deprotection of a carboxyl group as described in "Protective Groups in Organic Synthesis" above can be applied. Examples of the protecting group include $C_{1-6}$ alkyl which may be substituted; and $—C(=O)—C_{1-6}$ alkyl which may be substituted, and specifically, include methyl, ethyl, benzyl, allyl, and tert-butyl.

<Production Process 2 for Intermediate>

[Chem. 13]

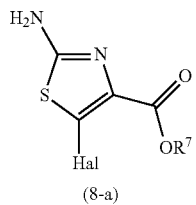
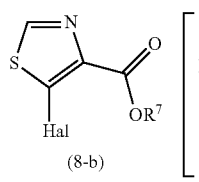
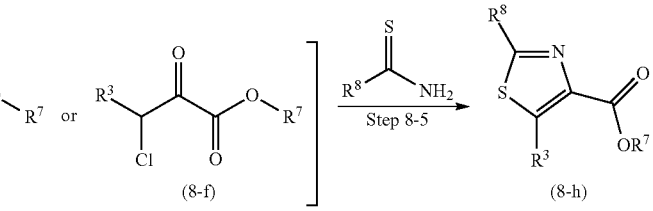
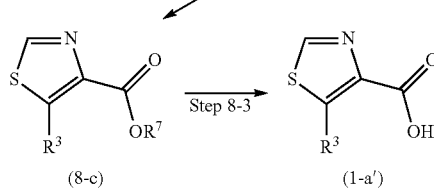
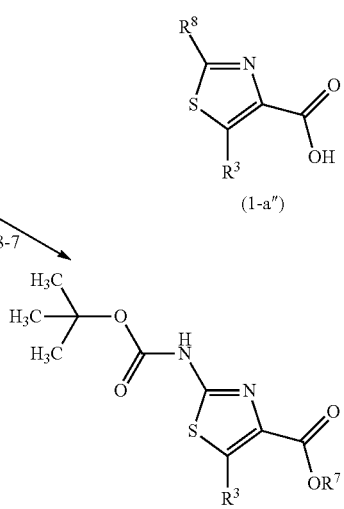

Step 8-8

-continued

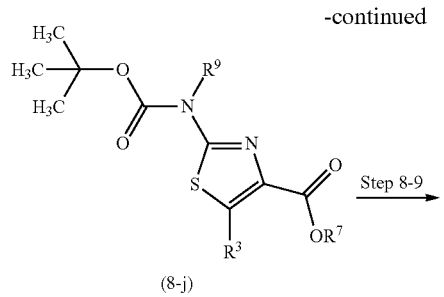

(8-j)

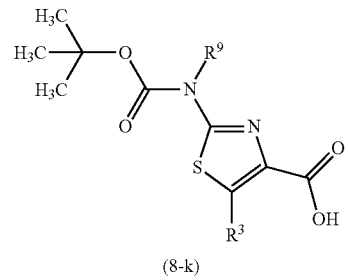

(8-k)

[wherein $R^8$ represents a $C_{1-6}$ alkyl group which may be substituted with halogen and $R^9$ represents a $C_{1-6}$ alkyl group].

Further, preparation can be performed in the following method in the case where the Ring A of the carboxylic acid compound (1-a) which is a starting material of Step 1 of Production Process 1 is thiazole.

Step 8-1 is a process for preparing a deaminated product (8-b) by using a compound (8-a) as a starting material. The preparation can be performed by allowing an alkali metal salt of a nitric acid or nitric esters to undergo a reaction under acidic conditions to produce a diazonium salt, with the removal of nitrogen. The reaction can be carried out in a solvent such as sulfuric acid, acetic acid, phosphoric acid, acetone, MeCN, DMSO and the like.

Step 8-2 is a process for preparing a compound (8-c) by allowing an aryl boric acid or alkyl tin compound to undergo a reaction with the compound (8-b). It can be carried out by the same method as Production Processes 4 and 5 above.

Step 8-3 is a reaction for obtaining a carboxylic acid compound (1-a') by subjecting an ester group to hydrolysis or deprotection, and can be carried out by the same method as Step 7-3 above.

In Step 8-4, a compound of the formula (8-e) or the formula (8-f) can be obtained from a compound (8-d) and an aldehyde by a method by TSUBOI, et al. (Bulletin of Chemical Society of Japan., 1987, Vol. 60, p. 2475), and in Step 8-5, a thiazole compound (8-g) or a compound (8-h) can be obtained by the reaction of the compound (8-e) or the compound (8-f) with thiourea or thioamide. The reaction is carried out in an alcohol or MeCN under heating.

Step 8-6 is a process for preparing the deaminated compound (8-c) from a 2-aminothiazole compound (8-g), and can be carried out by the same method as Step 8-1 above.

Step 8-7 is a process for preparing a compound (8-i) from the compound (8-g) having a 2-amino thiazole group, for which the condition for protection of an amino group as described in the above "Protective Groups in Organic Synthesis" can be applied.

Step 8-8 is a process for preparing an N-alkyl N-tert-botoxycarbonyl product from the tert-botoxycarbonyl product (8-i) by a method by KIM, et al. (Synlett., 1999, pp. 1239).

Step 8-9 is a reaction for obtaining a carboxylic acid compound (8-k) by subjecting an ester group to hydrolysis or deprotection, and can be carried out by the same method as Step 7-3 above.

<Production Process 3 for Intermediate>

Furthermore, the heteroaryl carbamate compound (4-a) used in the step of Production Processes 4 and 5 in which $R^1$ is —H can be prepared by the same method as Production Process 1.

[Chem. 14]

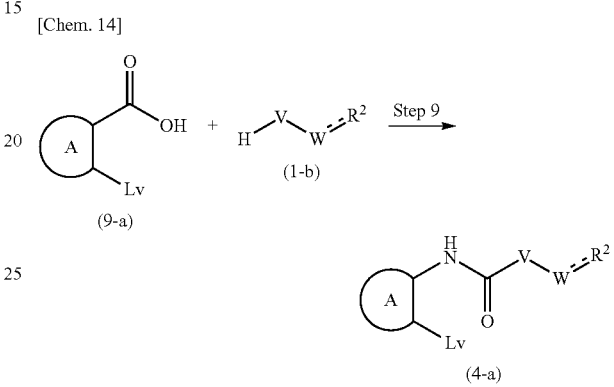

Moreover, several compounds of the formula (I) can be prepared from the compound of the present invention produced as above, by any combination of well-known processes that can be usually employed by a person skilled in the art, such as alkylation, acylation, substitution reaction, oxidation, reduction, hydrolysis, deprotection and the like.

The compound of the formula (I) is isolated and purified as its free compound, a salt, a hydrate, a solvate, or a polymorphic crystal substance thereof. The salt of the compound of the formula (I) can also be prepared in accordance with a conventional method for a salt formation reaction.

Isolation and purification are carried out by employing common chemical operations such as extraction, fractional crystallization, various types of fraction chromatography and the like.

Various isomers can be prepared by selecting an appropriate starting compound, or can be separated by making a use of the difference in the physicochemical properties between isomers. For example, the optical isomer can be obtained by means of general optical resolution methods of racemic products (for example, fractional crystallization for inducing diastereomers with optically active bases or acids, chromatography using a chiral column, etc. and the like). In addition, the isomers can also be prepared from an appropriate optically active starting material.

The pharmacological activity of the compound of the formula (I) was confirmed by the following test.

Test Example 1

Test of Muscarinic Receptor Affinity (In Vitro)

a. Preparation of a Membrane Specimen

The submandibular gland/heart and the cerebral cortex were harvested from male SD rats (Japan SLC, Inc.) and a 10-fold volume of a 25 mM Tris buffer (pH=7.4, hereinafter referred to as a Tris buffer) containing 3.75 mM magnesium chloride was added thereto, followed by homogenization under ice-cooling. Centrifugation was performed at 1,000 g, 4° C. for 10 minutes, and then ultracentrifugation was performed at 100,000 g, 4° C. for 30 minutes. This precipitate was suspended in a Tris buffer and stored at −80° C. After this, it was melted in use, and tested.

b. Experiment of the Muscarinic Receptor Binding

A membrane specimen of any one of the submandibular gland, the heart, and the cerebral cortex, [$^3$H]-N-methylscopolamine (N-methylscopolamine) and a compound to be tested were incubated in 0.3 mL of a Tris buffer at 25° C. for 2 hours, and suction-filtered through a glass filter (Whatman GF/B), and the filter was washed 8 times with 0.3 mL of a Tris buffer. The radioactivity of [$^3$H]-N-methylscopolamine adsorbed on the filter was measured with Top Count. Further, the receptor-specific binding was determined by adding 1 μM N-methylscopolamine. The affinity of the compound to be tested for the muscarinic receptor was determined as a dissociation constant (Ki) calculated from a concentration (IC$_{50}$) of the compound to be tested which inhibits the binding of the [$^3$H]-N-methylscopolamine as a labelled ligand by 50%.

As a result, for any one compound of the compounds of the formula (I), the results of the experiment of the receptor binding antagonistic experiments (activity values, Ki values, nM) are shown in Table 1.

TABLE 1

| Number of Example Ex | Ki value (nM) |
|---|---|
| 2 | 0.51 |
| 6 | 0.45 |
| 12 | 0.32 |
| 26 | 0.56 |
| 32 | 0.049 |
| 35 | 0.021 |
| 46 | 0.083 |
| 95 | 0.2 |
| 110 | 0.67 |
| 130 | 0.21 |
| 136 | 0.065 |
| 139 | 0.36 |
| 153 | 0.85 |
| 246 | 0.074 | a. Test Example 2

Test of Muscarinic Receptor Antagonism (In Vivo)

a. Test of Rat Airway Contraction

Male SD rats (250 to 400 g) were anesthetized by the intraperitoneal administration of pentobarbital sodium (Nembutal; 50 mg/kg), and the major airway was dissected. An airway cannula was intubated into the trachea, and the pressure in the airway was measured by a pressure transducer. After administration of pancuronium bromide (0.2 mg/kg, i.v.), a stable pressure in the airway was obtained before the experiment was initiated. For the experiment, by administration into the external maxillary vein/administration into the duodenum/oral administration/administration into the airway, physiological saline (in the case of oral administration/administration into the duodenum, distilled water) or a compound to be tested was administered, and after 5 to 30 minutes in the case of intravenous administration, after 0.25 to 6 hours in the case of oral administration into the duodenum, and after 0.25 to 72 hours in the case of administration into the airway, carbachol was intravenously administered at a dose (volume) of 30 μg/kg (1 mL/kg), and the pressures in the airway were then measured, respectively, for a period of 5 minutes. An inhibition rate of a drug to be tested on the carbachol-induced rise in the pressure in the airway in administration of physiological saline was determined, and a dose of the compound to be tested which inhibited the rise by 50% was taken as an ED$_{50}$ value.

b. Test of Rat Salivary Secretion

Male SD rats (250 to 400 g) were anesthetized by the intraperitoneal administration of pentobarbital sodium (Nembutal; 50 mg/kg). The compound to be tested (for a control group, physiological saline) was administered, and after 5 minutes, carbachol was administered at a dose of 30 μg/kg (1 mL/kg). The administration of a drug was performed in the same method as for the above-described test method by administration into the external maxillary vein/administration into the duodenum/oral administration/administration into the airway. The saliva secreted for 5 minutes immediately after administration of carbachol was recovered with cotton balls, and its weight was measured. An inhibition rate on the amount of saliva secreted in the control group was determined, and the dose of the compound to be tested which inhibited the amount of the saliva secreted in the control group by 50% was taken as an ID$_{50}$ value.

c. Test of Rat Bradycardia

Male SD rats (250 to 400 g) were anesthetized by the intraperitoneal administration of pentobarbital sodium (50 mg/kg), the neck was dissected, and the airway was secured by intubating a cannula into the trachea. Under artificial respiration (10 mL/kg at 90 times per minute), the heart rate was monitored from the total maxillary artery. A cannula was intubated into the external maxillary vein, whereby a drug was administered. After intubating a cannula into the trachea, and leaving it to stand for 10 minutes, the compound to be tested was administered intravenously/administered into the duodenum/administered orally/administered into the airway (for the control group, physiological saline was administered in the case of intravenous administration/oral administration, and distilled water was administered in the case of oral administration into the duodenum). After 5 to 30 minutes, carbachol was administered at a dose of 30 μg/kg (1 mL/kg), and an effect on the reduction of the heart rates in the control group up to 5 minutes from administration was measured. An inhibition rate for the reduction of the heart rates was determined, and the dose of the compound to be tested which inhibited the reduction of the heart rate in the control group by 50% was taken as an ID$_{50}$ value. For any one compound of the compounds of the formula (I), the results of the carbachol-induced airway contraction inhibitory action are shown in Tables 2 and 3. (Table 2: Evaluation after 3 hours from oral administration and Table 3: Evaluation after 24 hours from administration into the trachea, of 0.5 μg/kg of a drug, respectively)

TABLE 2

| Number of Example Ex | ID$_{50}$ (mg/kg) |
|---|---|
| 6 | 0.1 |
| 14 | 0.027 |
| 26 | 2.45 |
| 110 | 0.41 |
| 136 | 0.68 |
| 156 | 0.091 |
| 264 | 0.21 |

TABLE 3

| Number of Example Ex | Inhibition rate (%) |
|---|---|
| 32 | 82 |
| 43 | 64 |
| 46 | 90 |
| 50 | 61 |
| 57 | 64 |
| 65 | 61 |
| 66 | 80 |

From the results of the tests above, it was confirmed that the compound of the formula (I) has an antagonistic action on the binding of a muscarinic $M_3$ receptor. Therefore, it can be used for the treatment of respiratory diseases such as chronic obstructive pulmonary disease (COPD), chronic bronchitis, asthma, chronic airway obstruction, a pulmonary fiber disease, emphysema, rhinitis and the like; diseases of the digestive system such as irritable bowel syndrome, spastic colitis, gastroduodenal ulcers, gastrointestinal seizures or increased motor function, pains due to diverticulitis and contraction of the smooth muscle in the digestive system, and the like; diseases of the urinary system involving dysuria such as urinary incontinence, urgency of urination, urinary frequency and the like in the diseases such as neurogenic urinary frequency, neurogenic bladder, enuresis nocturna, bladder instability, bladder spasms, chronic cystitis and the like; lifestyle diseases such as obesity, diabetes and the like; motion sickness and the like.

A pharmaceutical composition comprising one or two or more kinds of the compound of the formula (I) or a salt thereof as an active ingredient can be prepared in accordance with a method which is usually used in the art, using an excipient which is usually used in the art, that is, a pharmaceutically acceptable excipient, a pharmaceutically acceptable soluble carrier or the like.

The administration can be carried out in any form of oral administration via tablets, pills, capsules, granules, powders, liquid preparations or the like, or parenteral administration via injections such as intraarticular, intravenous, intramuscular, suppositories, eye drops, eye ointments, percutaneous liquid preparations, ointments, percutaneous patches, transmucosal liquid preparations, transmucosal patches, inhalations and the like.

Regarding the solid composition for oral administration, tablets, powders, granules or the like are used. In such a solid composition, one or two or more kinds of active ingredients are mixed with at least one inert excipient such as lactose, mannitol, glucose, hydroxypropylcellulose, microcrystalline cellulose, starch, polyvinyl pyrrolidone, and/or magnesium aluminometasilicate and the like. According to a conventional method, the composition may contain inert additives such as a lubricant such as magnesium stearate, a disintegrator such as carboxymethylstarch sodium and the like, a stabilizing agent, and a solubilizing agent. As occasion demands, the tablets or the pills may be coated with a film of a sugar coating, or a gastric or enteric coating agent.

The liquid composition for oral administration includes a pharmaceutically acceptable emulsion, soluble liquid preparation, suspension, syrup, elixir or the like, and contains a generally used inert diluent, for example, purified water or EtOH. In addition to the inert diluent, this liquid composition may contain an auxiliary agent such as a solubilizing agent, a moistening agent, and a suspending agent, a sweetener, a flavor, an aromatic, or an antiseptic.

Injections for parenteral administration contain sterile aqueous or non-aqueous soluble liquid preparations, suspensions and emulsions. The aqueous solvent includes, for example, distilled water for injection or physiological saline. Examples of the non-aqueous solvent include propylene glycol, polyethylene glycol, plant oils such as olive oil, alcohols such as EtOH, Polysorbate 80 (Japanese Pharmacopeia) and the like. This composition may further contain a tonicity agent, an antiseptic, a moistening agent, an emulsifying agent, a dispersing agent, a stabilizing agent, or a solubilizing agent. These are sterilized, for example, by filtration through a bacteria retaining filter, blending of a bactericide, or irradiation. In addition, these can also be used by producing a sterile solid composition, and dissolving or suspending it in sterile water or a sterile solvent for injection prior to its use.

The drugs for external use includes ointments, plasters, creams, jellies, patches, sprays, lotions, eye drops, eye ointments and the like. The drugs contain generally used ointment bases, lotion bases, aqueous or non-aqueous soluble liquid preparations, suspensions, emulsions and the like. Examples of the ointment bases or the lotion bases include polyethylene glycol, propylene glycol, white vaseline, bleached bee wax, polyoxyethylene hydrogenated castor oil, glyceryl monostearate, stearyl alcohol, cetyl alcohol, lauromacrogol, sorbitan sesquioleate and the like.

Regarding the transmucosal agents such as inhalations, a transnasal agent and the like, those in the form of a solid, liquid, or semi-solid state are used, and may be prepared in accordance with a conventionally known method. For example, a known excipient, and also a pH adjusting agent, an antiseptic, a surfactant, a lubricant, a stabilizing agent, a thickening agent or the like may be appropriately added thereto. For their administration, an appropriate device for inhalation or blowing can be used. For example, a compound may be administered alone or as a powder of formulated mixture, or as a solution or suspension in combination with a pharmaceutically acceptable carrier, using a conventionally known device or sprayer, such as a measured administration inhalation device. The dry powder inhaler or the like may be for single or multiple administration use, and a dry powder or a powder-containing capsule may be used. Alternatively, this may be in a form such as a high pressure aerosol spray which uses an appropriate propellant, for example, a suitable gas such as chlorofluoroalkane, hydrofluoroalkane, carbon dioxide and the like, or other forms.

In oral administration, the daily dose is generally from about 0.001 to 100 mg/kg, preferably from 0.1 to 30 mg/kg, and even more preferably from 0.1 to 10 mg/kg, per body weight, administered in one portion or in 2 to 4 divided portions. In the case of intravenous administration, the daily dose is suitably from about 0.01 to 10 mg/kg per body weight, once a day or two or more times a day. In addition, a drug as a transmucosal agent is administered at a dose from about 0.001 to 100 mg/kg per body weight, once a day or two or more times a day. In the case of inhalation administration, the daily dose is from about 0.1 to 100 µg/kg per body weight, once a day or two or more times a day. The dose is appropriately decided in response to an individual case by taking the symptoms, the age, the gender and the like into consideration.

The compound of the formula (I) can be used in combination of various therapeutic agent or prophylactic agents for the diseases for which the compound of the formula (I) is considered to be effective, as described above. The combinations may be administered simultaneously, or separately and continuously, or at a desired time interval. The preparations to be co-administered may be a blend, or may be prepared individually.

EXAMPLES

Hereinbelow, the methods for preparing the compound of the formula (I) are described in more detail with reference to Examples. Also, the present invention is not intended to be limited to the compounds described in Examples below. Further, the production processes for the starting compound are each described with reference to Production Examples. Moreover, the preparation methods for the compound of the formula (I) are not limited to these specific preparation methods of Examples, and thus the compound of the formula (I) can also be prepared by a combination of such preparation methods, or a known production method which is apparent to a skilled person in the art.

By using such a preparation method, a method which is apparent to a skilled person in the art, or a modified method thereof, the compounds shown in the Tables below were prepared. The structures and physicochemical data of these compounds of the Examples, and the preparation methods therefor are shown in the Tables. Also, the symbols in the Tables have the following meanings.

[Pr: Production Example number
Ex: Example number
Syn: Preparation method (the numeral shows that the compound of the Example was prepared using the same preparation method as for the compound having its number as the Example number).
Structure: Structural formula
data: Physicochemical data. For example, NMR and MS are as follows.
NMR: Signal $\delta$ (ppm) of $^1$H-NMR, using DMSO-$d_6$ as a measurement solvent
NMR (CDCl$_3$): Signal $\delta$ (ppm) of $^1$H-NMR, using CDCl$_3$ as a measurement solvent
ESI (+): Values as measured in a positive mode
ESI (−): Values as measured in a negative mode Production Example 1

Under ice-cooling, to a suspension of CuBr$_2$ in MeCN was added tert-butyl nitrate. Next, methyl 2-amino-5,6-dihydro-4H-cyclopenta[b]thiophene-3-carboxylate was added portion wise thereto, followed by stirring under ice-cooling for 2 hours and then at room temperature for 3 hours. To the reaction mixture was added hydrochloric acid, and the aqueous layer was extracted with EtOAc. The organic layer was washed with water and brine in this order, dried over MgSO$_4$, and concentrated under reduced pressure. The residue was purified by medium-pressure preparative liquid chromatography (silica gel, YAMAZEN, YFLC WPrep2XY, hexane:EtOAc) to obtain methyl 2-bromo-5,6-dihydro-4H-cyclopenta[b]thiophene-3-carboxylate as a colorless liquid.

The compounds of Production Examples 1-1 to 1-2 shown in Tables below were synthesized in the same method as in Production Example 1, using the corresponding starting materials.

Production Example 2

To a solution of ethyl 2-amino-5-phenylthiazole-4-carboxylate in MeCN was added CuCl$_2$ at 0° C., and the isoamyl nitrate was slowly added dropwise thereto, followed by stirring for 1 hour. To the reaction mixture was added CHCl$_3$, followed by stirring at 0° C. for 2 hours and then at room temperature for 2 hours. The reaction mixture was neutralized by addition of a 1 M aqueous NaOH solution, and filtered through Celite. The filtrate was extracted with EtOAc, and the organic layer was washed with water and brine in this order and then dried over MgSO$_4$. After concentration under reduced pressure, the residue obtained was purified by medium-pressure preparative liquid chromatography (silica gel YAMAZEN YFLC WPrep2XY, hexane:EtOAc) to obtain ethyl 2-chloro-5-phenylthiazole-4-carboxylate as a yellow oil.

Production Example 3

To a suspension of methyl 2-bromo-5,6-dihydro-4H-cyclopenta[b]thiophene-3-carboxylate, phenyl boronic acid, and Pd(PPh$_3$)$_4$ in dioxane was added a 2 M aqueous Na$_2$CO$_3$ solution, followed by stirring at 90° C. for 15 hours. Water was added thereto, and the aqueous layer was extracted with EtOAc. The organic layer was dried over MgSO$_4$ and then concentrated under reduced pressure. The residue was purified by medium-pressure preparative liquid chromatography (silica gel, YAMAZEN YFLC WPrep2XY, hexane:EtOAc) to obtain methyl 2-phenyl-5,6-dihydro-4H-cyclopenta[b]thiophene-3-carboxylate as a colorless liquid.

The compounds of Production Examples 3-1 to 3-24 shown in Tables below were synthesized in the same method as in Production Example 3, using the corresponding starting materials.

Production Example 4

To a solution of methyl 2-phenyl-5,6-dihydro-4H-cyclopenta[b]thiophene-3-carboxylate in EtOH was added a 1 M aqueous NaOH solution, followed by heating under reflux for 5 hours. The reaction mixture was adjusted into pH=2 by addition of 1 M hydrochloric acid, and the solid precipitated was collected by filtration, and washed with water to obtain 2-phenyl-5,6-dihydro-4H-cyclopenta[b]thiophene-3-carboxylic acid as a white solid.

The compounds of Production Examples 4-1 to 4-20 shown in Tables below were synthesized in the same method as in Production Example 4, using the corresponding starting materials.

Production Example 5

To a solution of ethyl 2-chloro-5-phenylthiazole-4-carboxylate in THF was added a 1 M aqueous KOH solution, followed by stirring at 60° C. for 30 minutes. To the reaction mixture was added 1 M hydrochloric acid, and the solid precipitated was collected by filtration to obtain 2-chloro-5-phenylthiazole-4-carboxylic acid as a white solid.

The compounds of Production Examples 5-1 to 5-23 shown in Tables below were synthesized in the same method as in Production Example 5, using the corresponding starting materials.

Production Example 6

To a solution of 2-phenyl-5,6-dihydro-4H-cyclopenta[b]thiophene-3-carboxylic acid and TEA in toluene was added a solution of DPPA in toluene, followed by stirring at room temperature for 40 minutes, and then stirring at 90° C. for 60 minutes. Furthermore, a solution of (3R)-quinuclidinole in DMF was added thereto, followed by heating under reflux for 15 hours. To the reaction liquid was added water, followed by extraction with EtOAc. The organic layer was washed with water and brine in this order, dried over MgSO$_4$, and then concentrated under reduced pressure. The oily substance obtained was purified by medium-pressure preparative liquid chromatography (silica gel, YAMAZEN YFLC WPrep2XY, hexane:EtOAc) to obtain 2-phenyl-5,6-dihydro-4H-cyclopenta[b]thiophene-3-amine as a pale brown oil, but not a desired (3R)-1-azabicyclo[2.2.2]oct-3-yl(2-phenyl-5,6-dihydro-4H-cyclopenta[b]thien-3-yl)carbamate.

Production Example 7

To a solution of 2-bromothiophene-3-carboxylic acid and TEA in toluene was added dropwise a solution of DPPA in toluene. The reaction liquid was stirred at room temperature for 40 minutes, and then stirred at 90° C. for 60 minutes. To this solution was added a solution of 3-quiclidinole in DMF, followed by heating under reflux for 15 hours. To the reaction liquid was added water, followed by extraction with EtOAc. The organic layer was washed with water and brine in this order, dried over $MgSO_4$, and then concentrated under reduced pressure. The residue was purified by medium-pressure preparative liquid chromatography (silica gel, YAMAZEN YFLC WPrep2XY, $CHCl_3$:MeOH) to obtain 1-azabicyclo[2.2.2]oct-3-yl(2-bromo-3-thienyl)carbamate as a pale brown solid.

The compounds of Production Examples 7-1 to 7-5 shown in Tables below were synthesized in the same method as in Production Example 7, using the corresponding starting materials.

Production Example 8

To a solution of 2-phenylthiophene-3-carboxylic acid and TEA in toluene was added dropwise a solution of DPPA in toluene, followed by stirring at room temperature for 40 minutes, and then stirring at 90° C. for 60 minutes. To this solution was added tBuOH, followed by heating under reflux for 15 hours. To the reaction solution was added water, followed by extraction with EtOAc. The organic layer was washed with water and brine in this order, dried over $MgSO_4$, and then concentrated under reduced pressure. The residue was purified by medium-pressure preparative liquid chromatography (silica gel, YAMAZEN YFLC WPrep2XY, hexane:EtOAc) to obtain tert-butyl (2-phenyl-3-thienyl)carbamate as a pale brown oil.

Production Example 9

To a suspension of LAH in THF was added a solution of tert-butyl (2-phenyl-3-thienyl)carbamate in THF, followed by stirring at room temperature for 30 minutes and the stirring at 70° C. for 4 hours. After cooling at room temperature, $Na_2SO_4 \cdot 10H_2O$ was added thereto, followed by stirring at room temperature for 30 minutes. The reaction mixture was filtered and concentrated under reduced pressure to obtain 3-methylamino-2-phenylthiophene as a colorless oily substance.

Production Example 10

To a mixture of methyl 2-chloroisonicotinate, $Pd(PPh_3)_4$, and [(E)-2-phenylvinyl]boric acid in dioxane was added a 2 M aqueous $Na_2CO_3$ solution, followed by stirring at 90° C. for 5 hours. To the reaction mixture was added water, and the aqueous layer was extracted with EtOAc. The organic layer was dried over $MgSO_4$, and the filtrate was then concentrated under reduced pressure. The residue was purified by medium-pressure preparative liquid chromatography (silica gel, YAMAZEN YFLC WPrep2XY, hexane:EtOAc) to obtain methyl 2-[(E)-2-phenylvinyl]isonicotinate as a pale yellow solid.

Production Example 11

To a solution of methyl 2-[(E)-2-phenylvinyl]isonicotinate in hydrochloric acid and MeOH was added platinum oxide, followed by stirring at room temperature for 8 hours under a hydrogen atmosphere of 3 atm. The reaction mixture was filtered through Celite, and the filtrate was then concentrated under reduced pressure. To the residue were added an aqueous $Na_2CO_3$ solution and xylene, and the aqueous layer was extracted with $CHCl_3$. The organic layer was dried over $MgSO_4$ and then concentrated under reduced pressure to obtain methyl 2-(2-cyclohexylethyl)piperidine-4-carboxylate as a colorless oily substance.

Production Example 12

To a solution of methyl 2-[(E)-2-phenylvinyl]isonicotinate in acetic acid was added platinum oxide, followed by stirring at room temperature for 8 hours under a hydrogen atmosphere of 3 atm. The reaction mixture was filtered through Celite, and the filtrate was then concentrated under reduced pressure. To the residue were added an aqueous $Na_2CO_3$ solution, and the EtOAc was extracted. The organic layer was dried over $MgSO_4$ and then concentrated under reduced pressure to obtain methyl 2-(2-phenylethyl)piperidine-4-carboxylate as a colorless oil.

Production Example 13

To a suspension of methyl 2-(2-phenylethyl)piperidine-4-carboxylate in xylene were added ethyl bromoacetate and $K_2CO_3$, followed by heating under reflux for 8 hours. The reaction mixture was diluted with EtOAc, the organic layer was washed with water and brine in this order, dried over $MgSO_4$, and then filtered. The filtrate was concentrated under reduced pressure. To the residue was added hexane, and the insolubles were removed by filtration, followed by concentration under reduced pressure. The residue was purified by medium-pressure preparative liquid chromatography (silica gel, YAMAZEN YFLC WPrep2XY, hexane:EtOAc) to obtain methyl 1-(2-ethoxy-2-oxoethyl)-2-(2-phenylethyl)piperidine-4-carboxylate as a pale brown oil.

The compound of Production Example 13-1 shown in Tables below was synthesized in the same method as in Production Example 13, using the corresponding starting material.

Production Example 14

A suspension of tBuOK in toluene was heated under reflux, and a solution of methyl 1-(2-ethoxy-2-oxoethyl)-2-(2-phenylethyl)piperidine-4-carboxylate in toluene was added dropwise thereto, followed by stirring at the same temperature for 15 hours. After cooling to room temperature, concentrated hydrochloric acid was added thereto. The aqueous layer was separated and the organic layer was extracted with concentrated hydrochloric acid. The hydrochloric acid layer was heated under reflux for 15 hours. The reaction mixture was neutralized by addition of $K_2CO_3$ and the aqueous layer was extracted with $CHCl_3$. The organic layer was dried and then concentrated under reduced pressure. The residue obtained was purified by medium-pressure preparative liquid chromatography (silica gel, YAMAZEN YFLC WPrep2XY, $CHCl_3$:MeOH) to obtain 6-(2-phenylethyl)quinuclidin-3-one as a pale brown oil.

The compound of Production Example 14-1 shown in Tables below was synthesized in the same method as in Production Example 14, using the corresponding starting material.

Production Example 15

To a suspension of LAH in diethyl ether was added a solution of 6-(2-phenylethyl)quinuclidin-3-one in THF, followed by heating under reflux for 4 hours. To the reaction mixture was added Na$_2$SO$_4$.10H$_2$O, followed by stirring at room temperature for overnight. The reaction mixture was filtered, and the filtrate was then concentrated under reduced pressure to obtain 6-(2-phenylethyl)quinuclidin-3-ol as a colorless oil.

The compounds of Production Examples 15-1 and 15-2 shown in Tables below were synthesized in the same method as in Production Example 15, using the corresponding starting materials.

Production Example 16

To 1-azatricyclo[3.3.1.1$^{3,7}$]decane-4-carbonitrile was added concentrated hydrochloric acid, followed by heating under reflux for 3 hours. The reaction liquid was concentrated under reduced pressure to obtain 1-azatricyclo[3.3.1.1$^{3,7}$]decane-4-carboxylic acid hydrochloride as a solid. It was used in the next reaction without purification.

Production Example 17

To a solution of 1-azatricyclo[3.3.1.1$^{3,7}$]decane-4-carboxylic acid hydrochloride in EtOH was added concentrated sulfuric acid, followed by heating under reflux for 18 hours. The reaction liquid was concentrated under reduced pressure and then diluted with EtOAc. The EtOAc layer was washed with an aqueous NaHCO$_3$ solution and brine in this order, dried over MgSO$_4$, and then concentrated under reduced pressure to obtain a yellow oily substance. This was purified by silica gel column chromatography (CHCl$_3$:MeOH) to obtain ethyl 1-azatricyclo[3.3.1.1$^{3,7}$]decane-4-carboxylate as a yellow solid.

Production Example 18

To a suspension of LAH in THF was added dropwise a solution of ethyl 1-azatricyclo[3.3.1.1$^{3,7}$]decane-4-carboxylate in THF at 0 to 5° C., followed by stirring at the same temperature for 1 hour. Under ice-cooling, to the reaction mixture were added water, a 15% aqueous NaOH solution, and then water in this order. The insolubles were removed by filtration through Celite, followed by washing with EtOAc. The filtrate was dried over MgSO$_4$ and then concentrated under reduced pressure to obtain 1-azatricyclo[3.3.1.1$^{3,7}$]decan-4-yl methanol as a colorless oily substance.

The compounds of Production Examples 18-1 to 18-11 shown in Tables below were synthesized in the same method as in Production Example 18, using the corresponding starting materials.

Production Example 19

To a solution of methyl 2-phenylthiophene-3-carboxylate and NCS in CHCl$_3$ was added perchloric acid, followed by stirring at 50° C. for overnight. To the reaction mixture was added water, and the aqueous layer was extracted with EtOAc. The organic layer was washed with water and brine in this order, dried over MgSO$_4$, and then concentrated under reduced pressure. The residue obtained was purified by medium-pressure preparative liquid chromatography (silica gel, YAMAZEN YFLC WPrep2XY, hexane:EtOAc) to obtain methyl 5-chloro-2-phenylthiophene-3-carboxylate as a white solid.

Production Example 20

To a solution of 60% oily NaH in MeOH was added ethyl 2-chloro-5-phenylthiazole-4-carboxylate, followed by stirring at 70° C. for 1 hour. To the reaction mixture was added water, followed by extraction with EtOAc. The organic layer was washed with water and brine in this order, dried over MgSO$_4$, and then concentrated under reduced pressure. The residue was purified by medium-pressure preparative liquid chromatography (silica gel, YAMAZEN YFLC WPrep2XY, CHCl$_3$:MeOH) to obtain methyl 2-methoxy-5-phenylthiazole-4-carboxylate as a white solid.

Production Example 21

To a solution of ethyl 2-methyl-5-phenyl-1,3-thiazole-4-carboxylate in carbon tetrachloride was added NBS, followed by heating under reflux. The reaction liquid was filtered and concentrated under reduced pressure. The residue was purified by silica gel column chromatography (hexane:EtOAc=from 8:1 to 6:1) to obtain ethyl 2-(bromomethyl)-5-phenyl-1,3-thiazole-4-carboxylate (21a) and ethyl 2-(dibromomethyl)-5-phenyl-1,3-thiazole-4-carboxylate (21b) as a yellow solid, respectively.

The compound of Production Example 21-1 shown in Tables below was synthesized in the same method as in Production Example 21, using the corresponding starting material.

Production Example 22

A suspension of ethyl 2-(bromomethyl)-5-phenyl-1,3-thiazole-4-carboxylate obtained in Production Example 21 and NaOAc in MeCN was heated under reflux. To the reaction mixture was added water, followed by extraction with EtOAc. The organic layer was washed with water and brine in this order, dried over MgSO$_4$, and then concentrated under reduced pressure. The residue was purified by silica gel column chromatography (hexane:EtOAc=4:1) to obtain ethyl 2-(acetoxymethyl)-5-phenyl-1,3-thiazole-4-carboxylate as a pale yellow solid.

Production Example 23

To a solution of ethyl 2-(acetoxymethyl)-5-phenyl-1,3-thiazole-4-carboxylate obtained in Production Example 22 in EtOH was added a 1 M aqueous NaOH solution, followed by stirring at room temperature. The reaction liquid was neutralized by addition of 1 M hydrochloric acid, and extracted with CHCl$_3$. The organic layer was washed with brine, dried, and then concentrated under reduced pressure. The residue was purified by silica gel column chromatography (hexane:EtOAc=1:1) to obtain ethyl 2-(hydroxymethyl)-5-phenyl-1,3-thiazole-4-carboxylate as a pale yellow solid.

Production Example 24

To a solution of ethyl 2-(hydroxymethyl)-5-phenyl-1,3-thiazole-4-carboxylate obtained in Production Example 23 in DCM was added bis(2-methoxyethyl)aminosulfur trifluoride (Deoxo-Fluor(R)) at 0° C., followed by stirring for 30 minutes. The reaction was stopped by adding aqueous NaHCO$_3$ to the reaction mixture, followed by extraction by addition of EtOAc. The organic layer was washed with brine, dried over Na$_2$SO$_4$, and then concentrated under reduced pressure. The residue was purified by silica gel column chromatography (hexane:EtOAc) to obtain ethyl 2-(fluoromethyl)-5-phenyl-1,3-thiazole-4-carboxylate as a pale yellow oily substance.

The compounds of Production Examples 24-1 and 24-2 shown in Tables below were synthesized in the same method as in Production Example 24, using the aldehyde compounds of Production Examples 25 and 25-1 as described below as starting materials.

Production Example 25

To a solution of an aqueous solution of the dibromo product (21b) obtained in Production Example 21 in EtOH was added an aqueous silver nitrate solution, followed by heating under reflux for 15 minutes. To the reaction liquid was added 1 M hydrochloric acid, the solid precipitated was removed by filtration, and the filtrate was then extracted with $CHCl_3$. The organic layer was washed with brine, dried over $MgSO_4$, and then concentrated under reduced pressure. The residue was purified by silica gel column chromatography (hexane:EtOAc) to obtain ethyl 2-formyl-5-phenyl-1,3-thiazole-4-carboxylate as a pale yellow solid.

The compound of Production Examples 25-1 shown in Tables below was synthesized in the same method as in Production Example 25, using the corresponding starting material.

Production Example 26

A solution of ethyl 3-chloro-2-oxo-3-phenylpropanoate and trifluorothioacetamide in MeCN was heated under reflux. To the reaction mixture was added an aqueous $Na_2CO_3$ solution, followed by extraction with EtOAc. The organic layer was washed with water and brine in this order, dried, and then concentrated under reduced pressure. The residue was purified by medium-pressure preparative liquid chromatography (silica gel, YAMAZEN YFLC WPrep2XY, hexane: EtOAc) to obtain ethyl 5-phenyl-2-(trifluoromethyl)-1,3-thiazole-4-carboxylate as a white solid.

Production Example 27

To a suspension of methyl (2-bromo-4-methylphenyl)carbamate, and quinuclidin-3-ol and MS4A in toluene was added 60% oily NaH, followed by heating under reflux for 36 hours. The reaction mixture was filtered and the filtrate was concentrated under reduced pressure. The residue was purified by medium-pressure preparative liquid chromatography (silica gel, YAMAZEN YFLC WPrep2XY, $CHCl_3$: MeOH) to obtain 1-azabicyclo[2.2.2]oct-3-yl 2-bromo-4-methylphenyl)carbamate as a white solid.

Production Example 28

To a suspension of ethyl 5-bromothiazole-4-carboxylate, 1-methyl-4-(4,4,5,5-tetramethyl-1,3,2-dioxaborolan-2-yl)-1H-pyrazole and $Pd(PPh_3)_4$ in dioxane was added a 2 M aqueous $Na_2CO_3$ solution, followed by heating under reflux for 4 hours. To the reaction mixture was added water and the aqueous layer was extracted with EtOAc. The organic layer was dried over $MgSO_4$ and then concentrated under reduced pressure. The residue was purified by silica gel chromatography (hexane:EtOAc) to obtain ethyl 5-(1-methyl-1H-pyrazol-4-yl)-1,3-thiazole-4-carboxylate as a brown solid.

Production Example 29

Sodium was portion wise added to EtOH at 60° C. under stirring. EtOH was removed by evaporation, and diethyl ether was added thereto, and ethyl 2,2-dichloro-3-oxobutanate was then added dropwise thereto at 0° C. To the reaction mixture was added dropwise 2,6-difluorobenzaldehyde, followed by stirring at 0° C. for 30 minutes, and then heating under reflux for 4 hours. To the reaction mixture was added ice-water, followed by neutralization with 2 M HCl and extraction with EtOAc. The organic layer was washed with brine, dried, and then concentrated under reduced pressure. The residue was purified by silica gel column chromatography (hexane:EtOAc=from 85:15 to 6:4) to obtain ethyl 2-chloro-3-(2,6-difluorophenyl)oxirane-2-carboxylate as a yellow oil.

Production Example 30

To a solution of ethyl 2-chloro-3-(2,6-difluorophenyl)oxirane-2-carboxylate in EtOH was added thiourea, followed by heating under reflux for 4 hours. To the reaction mixture was added ice-water, followed by addition of $K_2CO_3$ to make it basic. The solid precipitated was collected by filtration and washed with water to obtain ethyl 2-amino-5-(2,6-difluorophenyl)-1,3-thiazole-4-carboxylate as a yellow solid.

Production Example 31

To a solution of ethyl 2-amino-5-(2,6-difluorophenyl)-1,3-thiazole-4-carboxylate in THF was slowly added dropwise tert-butyl nitrate under heating under reflux. After completion of dropwise addition, it was further stirred at the same temperature for 4 hours. The reaction mixture was cooled to room temperature, followed by addition of water and extraction with EtOAc. The organic layer was washed with brine, dried, and then concentrated under reduced pressure. The residue was purified by silica gel column chromatography (hexane: EtOAc=9:1-7:3) to obtain ethyl 5-(2,6-difluorophenyl)-1,3-thiazole-4-carboxylate as a yellow oily substance.

Production Example 32

To a mixed solution of ethyl 2-amino-5-phenyl-1,3-thiazole-4-carboxylate, acetic acid, and sulfuric acid was slowly added an aqueous $NaNO_2$ solution (5 mL) at 0° C., followed by stirring at the same temperature for 1 hour. This solution was added to an aqueous solution (40 mL) containing CuCN, NaCN, and $NaHCO_3$ (30 g) over 30 minutes, followed by stirring at the same temperature for 1 hour. EtOAc was added thereto, and the insolubles were filtered through Celite. The filtrate was extracted with EtOAc, the organic layer was dried, and the solvent was removed by evaporation under reduced pressure. The residue was purified by silica gel column chromatography (hexane:EtOAc=from 5:1 to 3:1 to 2:1) to obtain ethyl 2-cyano-5-phenyl-1,3-thiazole-4-carboxylate as a yellow solid.

Production Example 33

To a solution of ethyl 2-cyano-5-phenyl-1,3-thiazole-4-carboxylate in THF was added a 1 M aqueous KOH solution, followed by stirring at room temperature for 12 hours. To the reaction mixture was added 1 M hydrochloric acid, and the solid precipitated was collected by filtration to obtain 2-carbamoyl-5-phenyl-1,3-thiazole-4-carboxylic acid as a pale yellow solid.

Production Example 34

To a solution of ethyl 5-bromo-1,3-thiazole-4-carboxylate in toluene were added 2-(tributylstannyl)-1,3-thiazole and $PdCl_2(PPh_3)_2$, followed by heating under reflux for 6 hours. Water was added thereto and the aqueous layer was extracted with EtOAc. The organic layer was dried over $MgSO_4$, filtered, and concentrated under reduced pressure. The residue was purified by medium-pressure preparative liquid chromatography (silica gel, YAMAZEN YFLC WPrep2XY, hexane: EtOAc) to obtain ethyl 2,5'-bi-1,3-thiazole-4'-carboxylate as a yellow solid.

The compound of Production Examples 34-1 shown in Tables below was synthesized in the same method as in Production Example 34, using the corresponding starting material.

Production Example 35

To a solution of ethyl 2-amino-5-phenylthiazole-4-carboxylate in THF were added DIBOC, DMAP, and TEA, followed by stirring at room temperature. To the reaction mixture was added 1 M hydrochloric acid, followed by extraction with EtOAc. The organic layer was washed with water and brine in this order, dried over MgSO$_4$, and then concentrated under reduced pressure. The residue was purified by medium-pressure preparative liquid chromatography (silica gel, YAMAZEN YFLC WPrep2XY, hexane: EtOAc) to obtain ethyl 2-[(tert-butoxycarbonyl)amino]-5-phenyl-1,3-thiazole-4-carboxylate as a yellowish white amorphous substance.

Production Example 36

To a solution of ethyl 2-[(tert-butoxycarbonyl)amino]-5-phenyl-1,3-thiazole-4-carboxylate in THF were added EtOH, PPh$_3$, and DEAD, followed by stirring at room temperature. The reaction mixture was concentrated under reduced pressure. The residue was purified by medium-pressure preparative liquid chromatography (silica gel, YAMAZEN YFLC WPrep2XY, hexane: EtOAc) to obtain ethyl 2-[(tert-butoxycarbonyl) (ethyl)amino]-5-phenyl-1,3-thiazole-4-carboxylate as a yellow oil.

The compounds of Production Examples 36-1 and 36-2 shown in Tables below were synthesized in the same method as in Production Example 36, using the corresponding starting materials.

Production Example 37

To a suspension of 60% oily NaH in THF was added diethylphosphonoethyl acetate under ice-cooling. The reaction mixture was stirred for 30 minutes under ice-cooling, and a mixture of quinuclidin-3-one hydrochloride and THF was then added thereto under ice-cooling, followed by stirring at room temperature for 3 hours, and then stirring at 60° C. for 3 hours. The reaction mixture was cooled to room temperature, followed by addition of water and extraction with EtOAc. The organic layer was extracted with 1 M hydrochloric acid. The aqueous layer was basified with a 6 M aqueous NaOH solution and extracted with CHCl$_3$. The organic layer was washed with water and brine in this order, dried over MgSO$_4$, and then concentrated under reduced pressure to obtain a mixture of ethyl (2E)-1-azabicyclo[2.2.2]oct-3-ylidene acetate and ethyl (2Z)-1-azabicyclo[2.2.2]oct-3-ylidene acetate as a colorless oil.

Production Example 38

To quinuclidin-4-yl acetonitrile (500 mg) that had been synthesized by the method as described in Published Japanese translation of PCT application, No. 2001-521033 was added concentrated hydrochloric acid (3 mL), followed by heating under reflux. The reaction mixture was concentrated under reduced pressure, toluene was added, followed by concentration under reduced pressure. To the residue were added EtOH (10 mL) and concentrated sulfuric acid (1 mL), followed by stirring at 100° C. The reaction mixture was concentrated under reduced pressure, neutralized by addition of a 1 M aqueous NaOH solution, and extracted with CHCl$_3$. The organic layer was dried over MgSO$_4$ and then concentrated under reduced pressure to obtain ethyl quinuclidin-4-yl acetate (500 mg) as a yellow oily substance.

Production Example 39

To 1-benzyl-5-hydroxy-1-azoniabicyclo[3.2.1]octane 4-methylbenzenesulfonate (800 mg) that had been synthesized by the method as described in Published Japanese Patent Application No. 63-290878 was added a mixture of EtOH (8 mL), 10% Pd/Carbon with a 50% hydration (200 mg), and ammonium formate (500 mg), followed by heating under reflux. The reaction mixture was alkalified with addition of a 1 M aqueous NaOH solution, and extracted with a mixed solvent (CHCl$_3$:MeOH=9:1). The organic layer was dried over MgSO$_4$ and then concentrated under reduced pressure to obtain 1-azabicyclo[3.2.1]octan-5-ol (180 mg) as a colorless oily substance.

The compound of Production Example 39-1 in Tables below was prepared in the same method as in Production Example 39, using Production Example 44 to be described below as a starting material.

Production Example 40

In an ice-bath, to DIPA (4.1 mL) was added dropwise a 1 M solution of n-butyl lithium in hexane (10.1 mL). The reaction mixture was diluted with diethyl ether (10 mL), followed by stirring for 20 minutes. Next, the reaction mixture was stirred at −78° C., and a solution of ethyl 1-benzyl piperidine-3-carboxylate (6.0 g) in diethyl ether (20 mL) was added dropwise thereto, followed by stirring at −50° C. for 15 minutes. Next, after addition of 1,3-dibromopropane (2.8 mL) at 70° C., it was slowly returned to room temperature. Next, it was heated under reflux for 30 minutes. The reaction mixture was cooled, diluted with water, and extracted with diethyl ether. The organic layer was dried over MgSO$_4$ and then concentrated under reduced pressure. The residue was purified by medium-pressure preparative liquid chromatography (silica gel, YAMAZEN YFLC WPrep2XY, hexane: EtOAc) to obtain ethyl 1-benzyl-(3-bromopropyl)piperidine-3-carboxylate (1.08 g) as a colorless oily substance.

Production Example 41

A mixture of ethyl 1-benzyl-(3-bromopropyl)piperidine-3-carboxylate (1.08 g), toluene (10 mL), and CHCl$_3$ (2 mL) was heated under reflux for 2 hours. It was cooled to room temperature and then concentrated under reduced pressure. To the residue was added EtOAc, and the solid was collected by filtration to obtain 1-benzyl-5-(ethoxycarbonyl)-1-azoniabicyclo[3.3.1]nonane bromide (942 mg) as a colorless solid.

Production Example 42

A mixture of 1-benzyl-5-(ethoxycarbonyl)-1-azoniabicyclo[3.3.1]nonane bromide (932 mg), 10% Pd/Carbon with a 50% hydration (25 mg), and EtOH (15 mL) was stirred at room temperature under a hydrogen atmosphere of 3 atm. The reaction mixture was filtered through Celite and the filtrate was concentrated under reduced pressure to obtain a colorless solid. To this solid were added CHCl₃ and a saturated aqueous NaHCO₃ solution, and the organic layer was separated. Furthermore, the aqueous layer was extracted with CHCl₃. The organic layer was collected, dried over MgSO₄, and then concentrated under reduced pressure to obtain ethyl 1-azabicyclo[3.3.1]nonane-5-carboxylate (376 mg).

The compound of Production Example 42-1 in Tables below was prepared in the same method as in Production Example 42, using Production Example 56 to be described below as a starting material.

Production Example 42-2

To a solution of 1-benzyl-1-azoniabicyclo[2.2.1]heptane-4-carboxylate (3.25 g) in MeOH was added 10% Pd carbon with a 50% hydration (650 mg), followed by stirring at room temperature for 5 hours under a hydrogen atmosphere of 3 atm. The reaction mixture was filtered through Celite and the filtrate was concentrated. The residue was dissolved in MeOH and added with sulfuric acid (3 mL), followed by heating under reflux for 1 hour. The reaction mixture was neutralized with an aqueous K₂CO₃ solution and extracted with EtOAc. The organic layer was washed with water and brine in this order, dried over MgSO₄, and then concentrated under reduced pressure. The residue was purified by medium-pressure preparative liquid chromatography (silica gel, YAMAZEN YFLC WPrep2XY, CHCl₃: MeOH: 28% aqueous ammonia) to obtain methyl 1-azabicyclo[2.2.1]heptane-4-carboxylate (890 mg) as a colorless oily substance.

Production Example 43

To a solution of DIPA (3.1 mL) in THF (30 mL) was added dropwise a 2.6 M solution (8.6 mL) of n-butyl lithium in hexane at −70° C. After stirring at 0° C. for 40 minutes, EtOAc (2.3 mL) was added dropwise thereto at −70° C., followed by stirring for 5 minutes. A solution of 1-benzylazepan-4-one (3.6 g) in THF (10 mL) was added dropwise thereto, followed by stirring for 40 minutes. To the reaction mixture was added a saturated aqueous NH₄Cl solution, followed by addition of water and extraction with EtOAc. The organic layer was washed with brine, dried over MgSO₄, and then concentrated under reduced pressure. The residue was purified by medium-pressure preparative liquid chromatography (silica gel, YAMAZEN YFLC WPrep2XY, CHCl₃: MeOH: aqueous ammonia) to obtain ethyl (1-benzyl-4-hydroxyazepan-4-yl)acetate (5.0 g) as a yellow oily substance.

The compound of Production Example 43-1 shown in Tables below was synthesized in the same method as in Production Example 43, using the corresponding starting material.

Production Example 44

To a solution of 1-benzyl-4-(2-hydroxyethyl)azepan-4-ol (2.0 g) in DCM (20 mL) were added pyridine (4 mL) and p-toluenesulfonylchloride (1.68 g) at 0° C., followed by stirring at 0° C. for 3 hours and then at room temperature for overnight. The reaction mixture was concentrated under reduced pressure, alkalified by addition of a saturated aqueous NaHCO₃ solution, and then extracted with EtOAc. The organic layer was washed with water and brine in this order, dried over MgSO₄, and then concentrated under reduced pressure to obtain a pale red solid. EtOAc was added thereto and the solid was pulverized and collected by filtration to obtain 1-benzyl-5-hydroxy-1-azoniabicyclo[3.2.2]nonane 4-methylbenzenesulfonate (1.85 g) as a pale red powder.

Production Example 45

To a solution of tert-butyl 3-(2-ethoxy-2-oxoethyl)-3-hydroxypyrrolidine-1-carboxylate (6.35 g) in THF (100 mL) was added LiBH₄ (1.01 g), followed by heating under reflux for 4 hours. The reaction mixture was cooled to room temperature, then added with water, and extracted with EtOAc. The organic layer was washed with water and brine in this order, dried over MgSO₄, and then concentrated under reduced pressure to obtain tert-butyl 3-hydroxy-3-(2-hydroxyethyl)pyrrolidine-1-carboxylate (4.72 g) as a colorless oily substance.

Production Example 46

Under cooling with a cryogen (−10° C. to 0° C.), to a solution of tert-butyl 3-hydroxy-3-(2-hydroxyethyl)pyrrolidine-1-carboxylate (4.72 g) in pyridine (10 mL) was added p-toluene sulfonylchloride (1.68 g), followed by stirring at room temperature for overnight. The reaction mixture was concentrated under reduced pressure, and 1 M hydrochloric acid was added thereto, followed by extraction with EtOAc. The organic layer was washed with water and brine in this order, dried over MgSO₄, and then concentrated under reduced pressure. The residue was purified by medium-pressure preparative liquid chromatography (silica gel, YAMAZEN YFLC WPrep2XY, hexane: EtOAc) to obtain tert-butyl 3-hydroxy-3-(2-{[(4-methylphenyl)sulfonyl]oxy}ethyl)pyrrolidine-1-carboxylate (3.25 g) as a colorless oily substance.

Production Example 47

To a solution of tert-butyl 3-hydroxy-3-(2-{[(4-methylphenyl)sulfonyl]oxy}ethyl)pyrrolidine-1-carboxylate (3.24 g) in EtOH was added 4 M HCl/dioxane, followed by stirring at room temperature for overnight. The reaction mixture was concentrated under reduced pressure, followed by addition of an aqueous Na₂CO₃ solution and extraction with EtOAc. The aqueous layer was washed with EtOAc, and then concentrated under reduced pressure. The residue was purified by silica gel column chromatography (CHCl₃:MeOH:aqueous ammonia=7:3:0.3) to obtain 1-azabicyclo[2.2.1]heptan-4-ol (950 mg) as a colorless solid.

Production Example 48

To DIPA (3.6 mL) was added dropwise a 2.64 M solution of n-butyl lithium in hexane (8.93 mL) at −78° C., followed by stirring for 30 minutes. To the reaction mixture was added ethyl 1-benzyl-pyrrolidine-3-carboxylate (5.0 g), followed by stirring for 30 minutes. To the reaction mixture was added dropwise a solution of 1,2-dibromoethane (6.05 g) in THF, followed by warming to room temperature and stirring for 2 hours. To the reaction mixture was added an aqueous K₂CO₃ solution, followed by extraction with EtOAc. The aqueous layer was concentrated under reduced pressure, and to the residue was added EtOH, followed by stirring at room temperature for 30 minutes. The insolubles were removed by filtration and the filtrate was concentrated under reduced pressure. To the residue was added EtOH, followed by stirring at room temperature for 10 minutes. The insolubles were removed by filtration, and the filtrate was concentrated under reduced pressure to obtain 1-benzyl-1-azoniabicyclo[2.2.1]heptane-4-carboxylate (3.25 g) as a colorless solid.

Production Example 49

To a solution of ethyl 2-methyl-1,3-thiazole-4-carboxylate (14.53 g) in MeCN (150 mL) was added NBS (22.66 g), followed by heating under reflux for 3 hours. To the reaction mixture was added NBS (7.55 g), followed by heating under reflux for 2 hours. Under ice-cooling, to the reaction mixture was added a saturated aqueous NaHCO$_3$ solution, followed by stirring for 5 minutes, and then extraction with EtOAc. The organic layer was dried over MgSO$_4$ and then concentrated under reduced pressure. The residue obtained was purified by silica gel column chromatography (hexane:EtOAc=from 100:0 to 60:40) to obtain ethyl 5-bromo-2-methyl-1,3-thiazole-4-carboxylate (8.52 g) as a yellow solid.

Production Example 50

A mixture of 1-azabicyclo[2.2.1]heptan-3-one (Journal of Medicinal Chemistry, 1990, 33, pp. 2690-2697), hydrochloride (350 mg), platinum oxide (35 mg), and EtOH (5 mL) was stirred at room temperature under a hydrogen atmosphere. The reaction mixture was filtered through Celite, and the filtrate was concentrated under reduced pressure to obtain 1-azabicyclo[2.2.1]heptan-3-ol hydrochloride as a pale brown solid.

The compounds of Production Examples 50-1 and 50-2 shown in Tables below were synthesized in the same method as in Production Example 50, using the corresponding starting materials.

Production Example 51

A mixture of 1-azabicyclo[3.3.1]nonane-4-carbonitrile (U.S. Pat. No. 5,834,499, REFERENCE EXAMPLE 44) (1.7 g) and concentrated hydrochloric acid (10 mL) was heated under reflux for 4 hours. The reaction mixture was cooled to room temperature, and then concentrated under reduced pressure. To the residue were added EtOH (10 mL) and concentrated sulfuric acid (2 drops), followed by heating under reflux for 3 hours. The reaction mixture was cooled to room temperature and then concentrated under reduced pressure, and the residue was added with CHCl$_3$ and a 10% aqueous K$_2$CO$_3$ solution and partitioned. The aqueous layer was extracted with CHCl$_3$, and the organic layer was then combined, washed with brine, dried over MgSO$_4$, and then concentrated under reduced pressure. The residue was purified by medium-pressure preparative liquid chromatography (silica gel, YAMAZEN YFLC WPrep2XY, CHCl$_3$:MeOH:aqueous ammonia) to obtain ethyl 1-azabicyclo[3.3.1]nonane-4-carboxylate (2.2 g) as a pale brown oily substance.

The compound of Production Example 51-1 shown in Tables below was synthesized in the same method as in Production Example 51, using the corresponding starting material.

Production Example 52

To a mixture of a hydrochloride (2.3 g) of 1-azabicyclo[3.2.1]octan-4-one (Journal of Medicinal Chemistry, 1993, 36, pp. 683-689), dimethoxyethane (23 mL), and tBuOH (4.6 mL) was added tBuOK (1.60 g), followed by stirring at room temperature for 1 hour. To the reaction mixture was added p-toluenesulfonylmethyl isocyanide (3.06 g), followed by stirring in the ice bath. To the reaction mixture was added tBuOK (3.19 g) in two divided portions, followed by stirring for 30 minutes, and then stirring at room temperature for 2 hours. To the reaction mixture was added water, followed by extraction with CHCl$_3$. The organic layer was washed with water and brine in this order, and then extracted with 1 M hydrochloric acid. The aqueous layer was washed with EtOAc, and concentrated under reduced pressure to obtain a pale brown solid (1.9 g). This was added with concentrated hydrochloric acid (10 mL), heated under reflux for 4 hours, cooled to room temperature, and then concentrated under reduced pressure. To the residue were added EtOH (20 mL) and concentrated sulfuric acid (2 drops), followed by heating under reflux for 3 hours. The reaction mixture was cooled to room temperature and then concentrated under reduced pressure, and the residue was neutralized by addition with a 1 M aqueous NaOH solution, and extracted with EtOAc. The organic layer was washed with water and brine in this order, dried over MgSO$_4$, and then concentrated under reduced pressure. The residue was purified by medium-pressure preparative liquid chromatography (silica gel, YAMAZEN YFLC WPrep2XY, CHCl$_3$:MeOH:aqueous ammonia) to obtain ethyl 1-azabicyclo[3.2.1]octane-4-carboxylate (850 mg) as a colorless oily substance.

The compound of Production Example 52-1 shown in Tables below was synthesized in the same method as in Production Example 52, using the 1-benzylazepan-4-one.

Production Example 53

To a mixture of a hydrochloride (21.63 g) of 1-azabicyclo[3.2.1]octan-6-one (Journal of Medicinal Chemistry, 1993, 36, pp. 683-689), dimethoxyethane (210 mL), and tBuOH (43 mL) was added tBuOK (15 g) under ice-cooling, followed by stirring at room temperature for 40 minutes. Next, under ice-cooling, p-toluenesulfonylmethyl isocyanide (28.74 g) was added thereto, to which tBuOK (30 g) was added in two divided portions, followed by stirring for 30 minutes, and stirring at room temperature for 4 hours. To the reaction mixture was added water, followed by extraction with CHCl$_3$. The organic layer was washed with water and brine in this order, dried over MgSO$_4$, and then concentrated under reduced pressure. The residue was purified by medium-pressure preparative liquid chromatography (silica gel, YAMAZEN YFLC WPrep2XY, CHCl$_3$:MeOH:aqueous ammonia) to obtain a low-polarity product (6.17 g) and a high-polarity product (4.9 g) of 1-azabicyclo[3.2.1]octane-6-carbonitrile as a yellow oily substance and a diluted brown solid, respectively.

Production Example 54

A mixture of the high-polarity product (1.44 g) of 1-azabicyclo[3.2.1]octane-6-carbonitrile obtained in Production Example 53 and concentrated hydrochloric acid (15 mL) was heated under reflux for 4 hours, cooled to room temperature, and then concentrated under reduced pressure. Next, to the residue was added MeOH, followed by concentration under reduced pressure. To the residue were added MeOH (25 mL) and sulfuric acid (0.67 mL), followed by heating under reflux for 3 hours. The reaction mixture was concentrated under reduced pressure and solidified to dry, and to the residue were added CHCl$_3$ and a 1 M aqueous K$_2$CO$_3$ solution. The aqueous layer was extracted with CHCl$_3$, dried over MgSO$_4$, and then concentrated under reduced pressure. The residue was purified by medium-pressure preparative liquid chromatography (silica gel, YAMAZEN YFLC WPrep2XY, CHCl$_3$:

MeOH:aqueous ammonia) to obtain methyl 1-azabicyclo[3.2.1]octane-6-carboxylate (657 mg) as a colorless oily substance.

The compound of Production Example 54-1 shown in Tables below was synthesized in the same method as in Production Example 54, using the corresponding starting material.

Production Example 55

To DIPA (3.22 mL) was added dropwise a 2.64 M solution of n-butyl lithium in hexane (7.97 mL) at −78° C., followed by stirring for 30 minutes. To the reaction mixture was added ethyl 1-benzylazepane-4-carboxylate (5.0 g), followed by stirring for 30 minutes. Next, a solution of 1-bromo-2-chloroethane (3.02 g) in THF was added dropwise thereto, followed by warming to room temperature and stirring for 2 hours. To the reaction mixture was added an aqueous $K_2CO_3$ solution, followed by extraction with EtOAc. The organic layer was washed with water and brine in this order, dried over $MgSO_4$, and then concentrated under reduced pressure. The residue was purified by medium-pressure preparative liquid chromatography (silica gel, YAMAZEN YFLC WPrep2XY, $CHCl_3$:MeOH:aqueous ammonia). Desired fractions were collected, and concentrated under reduced pressure. After concentration under reduced pressure, to the residue, a part of which was solidified, was added EtOAc, followed by purification by silica gel column chromatography (EtOAc) to obtain ethyl 1-benzyl-4-(2-chloroethyl)azepane-4-carboxylate (4.11 g) as a colorless oily substance.

Production Example 56

A solution of ethyl 1-benzyl-4-(2-chloroethyl)azepane-4-carboxylate (4.1 g) in MeCN (200 mL) was stirred at 40° C. for 10 hours. The reaction mixture was concentrated under reduced pressure to obtain 1-benzyl-5-(ethoxycarbonyl)-1-azoniabicyclo[3.2.2]nonane chloride (4.1 g) as a colorless oily substance.

Production Example 57

The compounds of Production Examples 57 to 57-3 shown in Tables below were synthesized in the same method as in Example 6, using the corresponding starting material.

TABLE 4

| Pr | Structure | data |
|---|---|---|
| 1 | | ESI (+): 283 |
| 1-1 | | ESI (+): 301 |
| 1-2 | 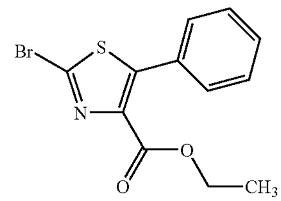 | ESI (+): 312 336 |
| 2 | 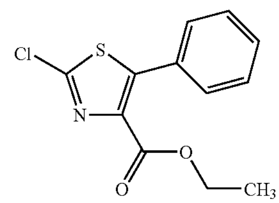 | ESI (+): 290 |
| 3 | 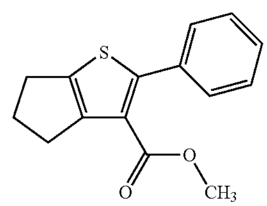 [SMILES: COC(=O)c1c(-c2ccccc2)sc2c1CCC2] | ESI (+): 281 |
| 3-1 | 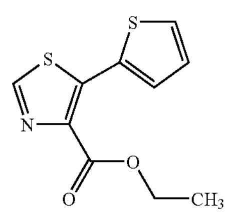 | ESI (+): 262 501 |
| 3-2 | 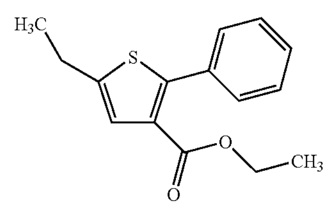 [SMILES: CCOC(=O)c1cc(CC)sc1-c1ccccc1] | ESI (+): 283 |
| 3-3 | 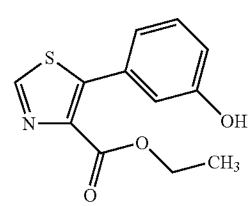 [SMILES: CCOC(=O)c1ncsc1-c1cccc(O)c1] | ESI (+): 272 |
| 3-4 | 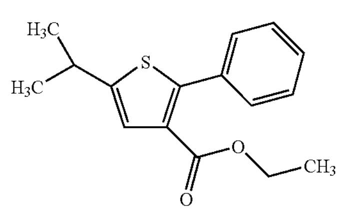 [SMILES: CCOC(=O)c1cc(C(C)C)sc1-c1ccccc1] | ESI (+): 297 |

TABLE 4-continued

| Pr | Structure | data |
|---|---|---|
| 3-5 | ethyl 5-(4-fluoro-3-methylphenyl)thiazole-4-carboxylate | ESI (+): 266 |
| 3-6 | ethyl 5-(2,5-difluorophenyl)thiazole-4-carboxylate | ESI (+): 292 |
| 3-7 | ethyl 5-(3-cyanophenyl)thiazole-4-carboxylate | ESI (+): 281 |
| 3-8 | ethyl 5-(3-chloro-4-fluorophenyl)thiazole-4-carboxylate | ESI (+): 286 |
| 3-9 | ethyl 5-(3-chloro-5-fluorophenyl)thiazole-4-carboxylate | ESI (+): 308 |

TABLE 5

| Pr | Structure | data |
|---|---|---|
| 3-10 | ethyl 5-(pyridin-4-yl)thiazole-4-carboxylate | ESI (+): 257 |
| 3-11 | ethyl 5-(3-cyano-4-fluorophenyl)thiazole-4-carboxylate | ESI (+): 277 |
| 3-12 | ethyl 5-(2-methylphenyl)thiazole-4-carboxylate | ESI (+): 270 |
| 3-13 | ethyl 5-(3,5-dichlorophenyl)thiazole-4-carboxylate | ESI (+): 302 |
| 3-14 | ethyl 5-(3-methylphenyl)thiazole-4-carboxylate | ESI (+): 270 |
| 3-15 | ethyl 5-(pyridin-3-yl)thiazole-4-carboxylate | ESI (+): 257 |
| 3-16 | ethyl 5-(3-trifluoromethylphenyl)thiazole-4-carboxylate | ESI (+): 302 |
| 3-17 | ethyl 5-(5-chlorothiophen-2-yl)thiazole-4-carboxylate | ESI (+): 296 |

TABLE 5-continued

| Pr | Structure | data |
|---|---|---|
| 3-18 | ethyl 5-(3,4-difluorophenyl)thiazole-4-carboxylate | ESI (+): 270 |
| 3-19 | 3-fluoro-2-phenylaniline | ESI (+): 188 |
| 3-20 | ethyl 5-(5-chloro-2-fluorophenyl)thiazole-4-carboxylate | ESI (+): 308 |
| 3-21 | 3-methyl-2-phenylaniline | ESI (+): 184 |
| 3-22 | ethyl 5-(2-chlorophenyl)thiazole-4-carboxylate | ESI (+): 290 |
| 3-23 | 2-methyl-6-phenylaniline | ESI (+): 184 |

TABLE 6

| Pr | Structure | data |
|---|---|---|
| 3-24 | ethyl 5-(3-chlorophenyl)-2-methylthiazole-4-carboxylate | ESI (+): 304 |
| 4 | 2-phenyl-5,6-dihydro-4H-cyclopenta[b]thiophene-3-carboxylic acid | ESI (+): 267 |
| 4-1 | 5-(2,4-difluorophenyl)thiazole-4-carboxylic acid | ESI (+): 264 |
| 4-2 | 5-ethyl-2-phenylthiophene-3-carboxylic acid | ESI (+): 255 |
| 4-3 | 5-(3,5-difluorophenyl)thiazole-4-carboxylic acid | ESI (+): 264 |
| 4-4 | 5-isopropyl-2-phenylthiophene-3-carboxylic acid | ESI (+): 269 |
| 4-5 | 5-(3-chlorophenyl)thiazole-4-carboxylic acid | ESI (−): 238 |

TABLE 6-continued
| Pr | Structure | data |
|---|---|---|
| 4-6 | 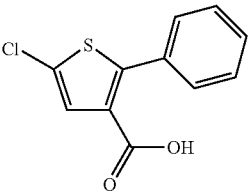 [SMILES: O=C(O)c1cc(Cl)sc1-c1ccccc1] | ESI (+): 261 |
| 4-7 | 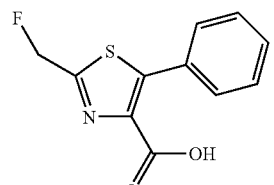 | ESI (−): 236 |
| 4-8 | 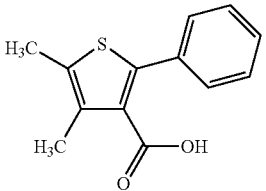 [SMILES: Cc1sc(-c2ccccc2)c(C(=O)O)c1C] | ESI (+): 255 |
| 4-9 | 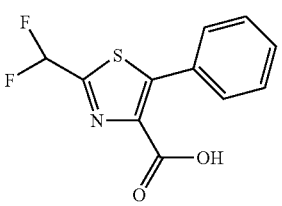 [SMILES: O=C(O)c1nc(C(F)F)sc1-c1ccccc1] | ESI (−): 254 |
| 4-10 | 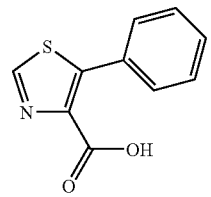 [SMILES: O=C(O)c1ncsc1-c1ccccc1] | ESI (−): 204 |
| 4-11 | 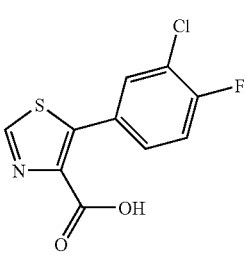 [SMILES: O=C(O)c1ncsc1-c1ccc(F)c(Cl)c1] | ESI (−): 256 |
| 4-12 | 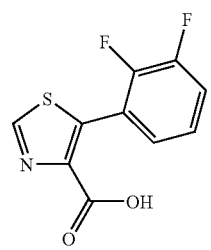 [SMILES: O=C(O)c1ncsc1-c1cccc(F)c1F] | ESI (+): 264 |
TABLE 7
| Pr | Structure | data |
|---|---|---|
| 4-13 | 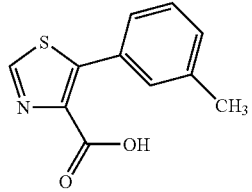 | ESI (−): 218 |
| 4-14 | 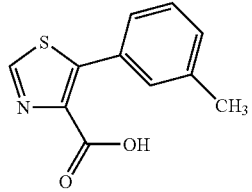 | ESI (+): 264 |
| 4-15 | 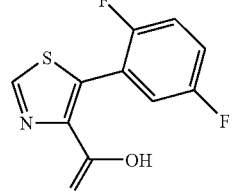 | ESI (−): 238 |
| 4-16 | 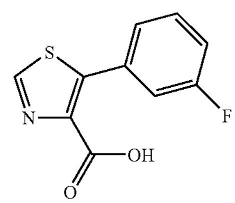 [SMILES: O=C(O)c1ncsc1-c1cccc(F)c1] | ESI (−): 222 |
| 4-17 | 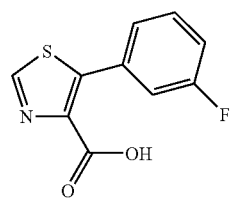 | ESI (+): 234 |
| 4-18 | 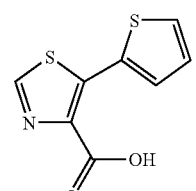 | ESI (+): 246 |
| 4-19 | 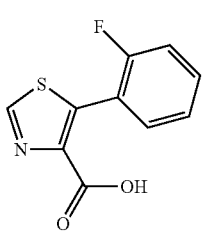 [SMILES: O=C(O)c1ncsc1-c1ccccc1F] | ESI (−): 244 |

TABLE 7-continued

| Pr | Structure | data |
|---|---|---|
| 4-20 | 2-(trifluoromethyl)-5-phenylthiazole-4-carboxylic acid | ESI (+): 296 |
| 5 | 2-chloro-5-phenylthiazole-4-carboxylic acid | ESI (+): 262 |
| 5-1 | 2-bromo-5-phenylthiazole-4-carboxylic acid | ESI (+): 306, 308 |
| 5-2 | 2-methoxy-5-phenylthiazole-4-carboxylic acid | ESI (+): 258 |
| 5-3 | 5-(3-cyanophenyl)thiazole-4-carboxylic acid | ESI (−): 229 |
| 5-4 | 5-(pyridin-4-yl)thiazole-4-carboxylic acid | ESI (−): 205 |
| 5-5 | 5-(3-chloro-5-fluorophenyl)thiazole-4-carboxylic acid | ESI (−): 256 |

TABLE 8

| Pr | Structure | data |
|---|---|---|
| 5-6 | 5-(2-methylphenyl)thiazole-4-carboxylic acid | ESI (+): 242 |
| 5-7 | 5-(1-methyl-1H-pyrazol-3-yl)thiazole-4-carboxylic acid | ESI (−): 208 |
| 5-8 | 5-(3-trifluoromethylphenyl)thiazole-4-carboxylic acid | ESI (−): 272 |
| 5-9 | 5-(3-cyano-4-fluorophenyl)thiazole-4-carboxylic acid | ESI (−): 247 |
| 5-10 | 5-(3,4-difluorophenyl)thiazole-4-carboxylic acid | ESI (−): 240 |
| 5-11 | 5-(3,5-dichlorophenyl)thiazole-4-carboxylic acid | ESI (−): 272, 274 |
| 5-12 | 5-(5-chloro-2-fluorophenyl)thiazole-4-carboxylic acid | ESI (+): 280 |

TABLE 8-continued

| Pr | Structure | data |
|---|---|---|
| 5-13 | thiazole-pyridine carboxylic acid | ESI (−): 205 |
| 5-14 | thiazole-(3-hydroxyphenyl) carboxylic acid | ESI (−): 220 |
| 5-15 | thiazole-thiazole carboxylic acid | ESI (+): 235 |
| 5-16 | thiazole-(2,6-difluorophenyl) carboxylic acid | ESI (+): 264 |
| 5-17 | thiazole-pyrazine carboxylic acid | ESI (+): 230 |
| 5-18 | thiazole-(4-fluoro-3-methylphenyl) carboxylic acid | ESI (−): 236 |
| 5-19 | 2-(Boc-amino)-5-phenylthiazole-4-carboxylic acid | ESI (+): 343 |

TABLE 9

| Pr | Structure | data |
|---|---|---|
| 5-20 | 2-(N-Boc-N-ethylamino)-5-phenylthiazole-4-carboxylic acid | ESI (+): 371 |
| 5-21 | 2-(N-Boc-N-(3-phenylpropyl)amino)-5-phenylthiazole-4-carboxylic acid | ESI (+): 461 |
| 5-22 | 2-(N-Boc-N-(2-benzyloxyethyl)amino)-5-phenylthiazole-4-carboxylic acid | ESI (+): 477 |
| 5-23 | 2-difluoromethyl-5-(3-chlorophenyl)thiazole-4-carboxylic acid | ESI (+): 312 |
| 6 | 3-amino-2-phenyl-5,6-dihydro-4H-cyclopenta[b]thiophene | ESI (+): 216 |
| 7 | 2-bromothiophen-3-yl carbamate of quinuclidin-3-ol | SB |

TABLE 9-continued

| Pr | Structure | data |
|---|---|---|
| 7-1 | 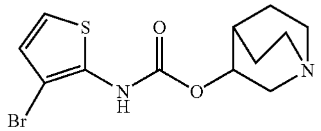 [SMILES: O=C(Nc1sccc1Br)OC1CN2CCC1CC2] | ESI (+): 331, 333 |
| 7-2 | 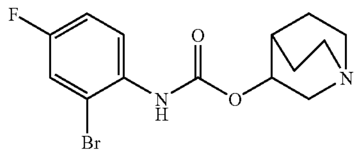 [SMILES: O=C(Nc1ccc(F)cc1Br)OC1CN2CCC1CC2] | ESI (+): 343, 345 |
| 7-3 | 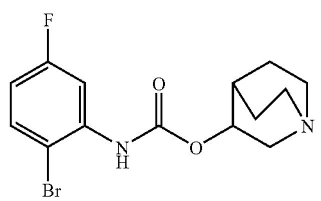 [SMILES: O=C(Nc1cc(F)ccc1Br)OC1CN2CCC1CC2] | ESI (+): 345 |
| 7-4 | 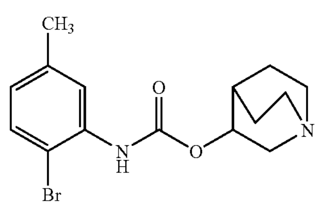 [SMILES: Cc1ccc(Br)c(NC(=O)OC2CN3CCC2CC3)c1] | ESI (+): 339, 341 |
| 7-5 | 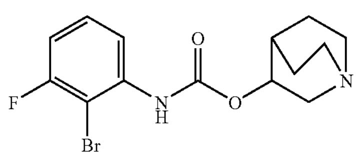 [SMILES: O=C(Nc1cccc(F)c1Br)OC1CN2CCC1CC2] | ESI (+): 343 |
| 8 | 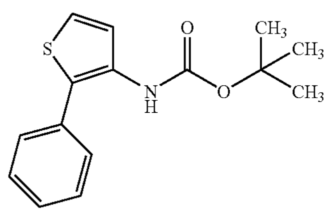 [SMILES: CC(C)(C)OC(=O)Nc1ccsc1-c1ccccc1] | ESI (+): 298 |

TABLE 10

| Pr | Structure | data |
|---|---|---|
| 9 | 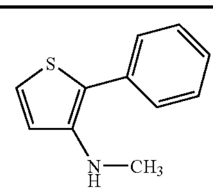 | ESI (+): 190 |

TABLE 10-continued

| Pr | Structure | data |
|---|---|---|
| 10 | 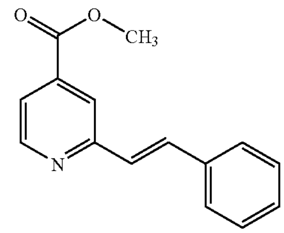 [SMILES: COC(=O)c1ccnc(/C=C/c2ccccc2)c1] | ESI (+): 240 |
| 11 | 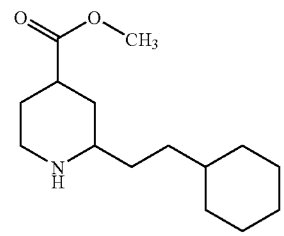 [SMILES: COC(=O)C1CCNC(CCC2CCCCC2)C1] | ESI (+): 254 |
| 12 | 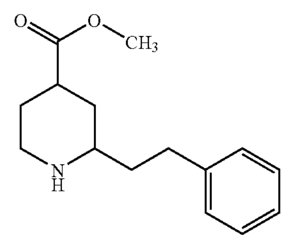 [SMILES: COC(=O)C1CCNC(CCc2ccccc2)C1] | ESI (+): 248 |
| 13 | 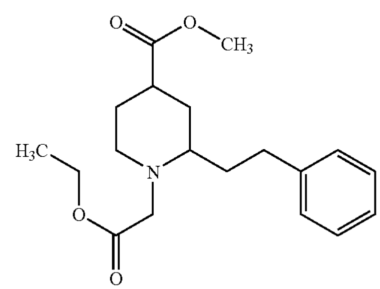 [SMILES: CCOC(=O)CN1CCC(C(=O)OC)CC1CCc1ccccc1] | ESI (+): 334 |
| 13-1 | 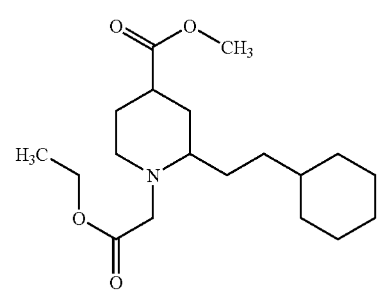 [SMILES: CCOC(=O)CN1CCC(C(=O)OC)CC1CCC1CCCCC1] | ESI (+): 340 |
| 14 | 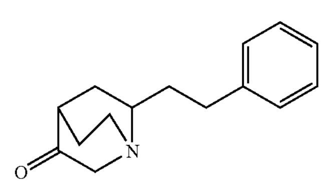 [SMILES: O=C1CN2CCC1CC2CCc1ccccc1] | ESI (+): 230 |

TABLE 10-continued

| Pr | Structure | data |
|---|---|---|
| 14-1 | 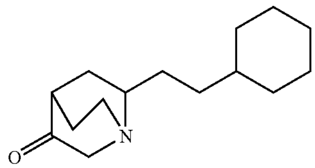 [SMILES: O=C1CN2CCC1CC2CCC1CCCCC1] | ESI (+): 236 |
| 15 | 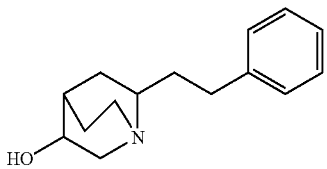 [SMILES: OC1CN2CCC1CC2CCc1ccccc1] | ESI (+): 232 |
| 15-1 | 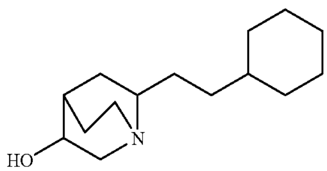 [SMILES: OC1CN2CCC1CC2CCC1CCCCC1] | ESI (+): 238 |
| 15-2 | 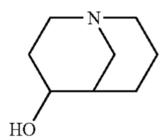 | ESI (+): 142 |
| 16 | 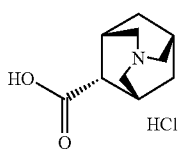 [SMILES: O=C(O)[C@@H]1[C@@H]2C[C@@H]3C[C@H]1CN(C3)C2 ; Cl] | ESI (+): 182 |
| 17 | 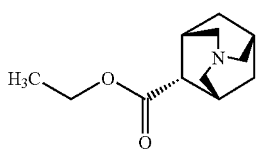 | ESI (+): 210 |
| 18 | 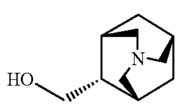 [SMILES: OC[C@@H]1[C@@H]2C[C@@H]3C[C@H]1CN(C3)C2] | ESI (+): 168 |

TABLE 11

| Pr | Structure | data |
|---|---|---|
| 18-1 | | ESI (+): 154 |
| 18-2 | | ESI (+): 142 |
| 18-3 | | ESI (+): 156 |
| 18-4 | 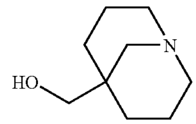 | ESI (+): 156 |
| 18-5 | 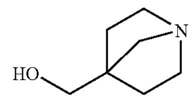 | ESI (+): 128 |
| 18-6 | 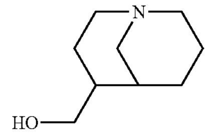 [SMILES: OCC1CCN2CCCC1C2] | ESI (+): 156 |
| 18-7 | 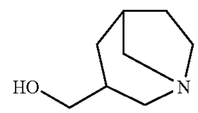 | ESI (+): 142 |
| 18-8 | 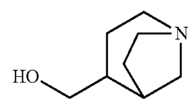 | ESI (+): 142 |
| 18-9 | 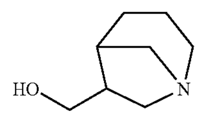 | SB |
| 18-10 | 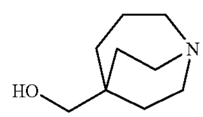 [SMILES: OCC12CCCN(CC1)CC2] | ESI (+): 156 |
| 18-11 | 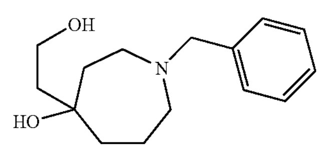 [SMILES: OCCC1(O)CCCN(Cc2ccccc2)CC1] | ESI (+): 250 |
| 19 | 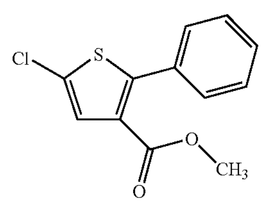 [SMILES: COC(=O)c1cc(Cl)sc1-c1ccccc1] | SB |
| 20 | 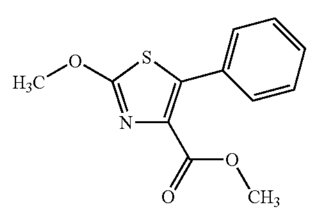 [SMILES: COC(=O)c1nc(OC)sc1-c1ccccc1] | ESI (+): 272 |

TABLE 11-continued

| Pr | Structure | data |
|---|---|---|
| 21a | (2-(bromomethyl)-5-phenylthiazole-4-carboxylic acid ethyl ester) | ESI (+): 348, 350 |
| 21b | (2-(dibromomethyl)-5-phenylthiazole-4-carboxylic acid ethyl ester) | ESI (+): 427 |
| 21-1 | (2-(dibromomethyl)-5-(3-chlorophenyl)thiazole-4-carboxylic acid ethyl ester) | ESI (+): 461 |

TABLE 12

| Pr | Structure | data |
|---|---|---|
| 22 | (2-(acetoxymethyl)-5-phenylthiazole-4-carboxylic acid ethyl ester) | ESI (+): 328 |
| 23 | (2-(hydroxymethyl)-5-phenylthiazole-4-carboxylic acid ethyl ester) | ESI (+): 286 |
| 24 | (2-(fluoromethyl)-5-phenylthiazole-4-carboxylic acid ethyl ester) | ESI (+): 288 |

TABLE 12-continued

| Pr | Structure | data |
|---|---|---|
| 24-1 | (2-(difluoromethyl)-5-phenylthiazole-4-carboxylic acid ethyl ester) | ESI (+): 306 |
| 24-2 | (2-(difluoromethyl)-5-(3-chlorophenyl)thiazole-4-carboxylic acid ethyl ester) | ESI (+): 340 |
| 25 | (2-formyl-5-phenylthiazole-4-carboxylic acid ethyl ester) | SB |
| 25-1 | (2-formyl-5-(3-chlorophenyl)thiazole-4-carboxylic acid ethyl ester) | SB |
| 26 | (2-(trifluoromethyl)-5-phenylthiazole-4-carboxylic acid ethyl ester) | ESI (+): 324 |
| 27 | (quinuclidin-3-yl (2-bromo-4-methylphenyl)carbamate) | ESI (+): 399, 241 |
| 28 | (5-(1-methyl-1H-pyrazol-4-yl)thiazole-4-carboxylic acid ethyl ester) | ESI (+): 260 |

TABLE 12-continued

| Pr | Structure | data |
|---|---|---|
| 29 | ethyl 3-(2,6-difluorophenyl)-2-chlorooxirane-2-carboxylate | ESI (+): 285 |
| 30 | ethyl 2-amino-5-(2,6-difluorophenyl)thiazole-4-carboxylate | ESI (+): 307 |

TABLE 13

| Pr | Structure | data |
|---|---|---|
| 31 | ethyl 5-(2,6-difluorophenyl)thiazole-4-carboxylate | ESI (+): 292 |
| 32 | ethyl 2-cyano-5-phenylthiazole-4-carboxylate | ESI (+): 281 |
| 33 | 2-carbamoyl-5-phenylthiazole-4-carboxylic acid | ESI (−): 247 |
| 34 | ethyl 5-(thiazol-2-yl)thiazole-4-carboxylate | ESI (+): 263 |
| 34-1 | ethyl 5-(pyrazin-2-yl)thiazole-4-carboxylate | ESI (+): 258 |
| 35 | ethyl 2-(tert-butoxycarbonylamino)-5-phenylthiazole-4-carboxylate | ESI (+): 371 |
| 36 | ethyl 2-(N-tert-butoxycarbonyl-N-ethylamino)-5-phenylthiazole-4-carboxylate | ESI (+): 399 |
| 36-1 | ethyl 2-(N-(3,3-dimethylbutanoyl)-N-(3-phenylpropyl)amino)-5-phenylthiazole-4-carboxylate | ESI (+): 489 |
| 36-2 | ethyl 2-(N-(2-(benzyloxy)ethyl)-N-tert-butoxycarbonylamino)-5-phenylthiazole-4-carboxylate | ESI (+): 505 |
| 37 | ethyl 2-(quinuclidin-3-ylidene)acetate | ESI (+): 196 |
| 38 | ethyl 2-(quinuclidin-4-yl)acetate | ESI (+): 198 |

US 8,367,696 B2
TABLE 13-continued
| Pr | Structure | data |
|---|---|---|
| 39 | 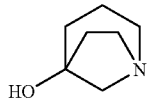 | ESI (+): 128 |
TABLE 14
| Pr | Structure | data |
|---|---|---|
| 39-1 | 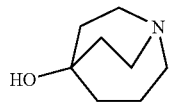 | ESI (+): 142 |
| 40 | 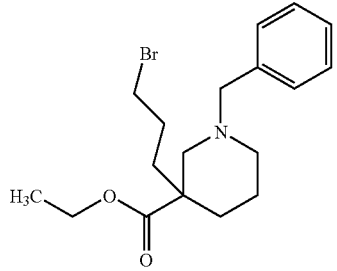 [SMILES: CCOC(=O)C1(CCCBr)CCCN(Cc2ccccc2)C1] | ESI (+): 368, 370 |
| 41 | 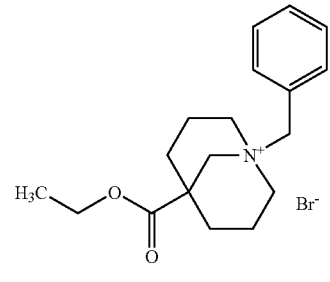 [SMILES: CCOC(=O)C12CCC[N+](Cc3ccccc3)(CCC1)C2 ; [Br-]] | ESI (+): 288 |
| 42 | 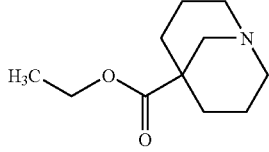 | ESI (+): 198 |
| 42-1 | 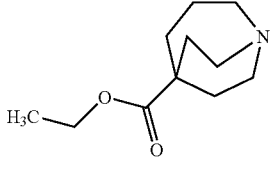 | ESI (+): 198 |
| 42-2 | 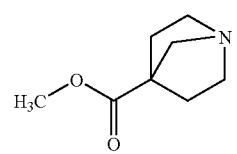 | ESI (+): 156 |
TABLE 14-continued
| Pr | Structure | data |
|---|---|---|
| 43 | 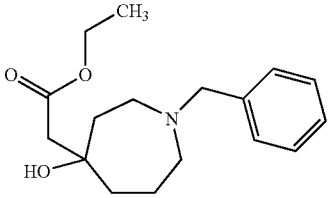 [SMILES: CCOC(=O)CC1(O)CCCN(Cc2ccccc2)CC1] | ESI (+): 292 |
| 43-1 | 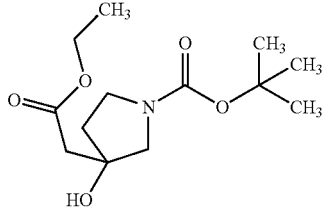 [SMILES: CCOC(=O)CC1(O)CCN(C(=O)OC(C)(C)C)C1] | ESI (+): 296 |
| 44 | 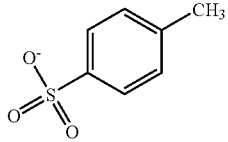 | ESI (+): 232 |
| 45 | 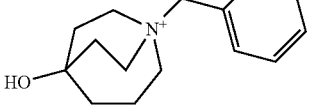 | ESI (+): 254 |
| 46 | 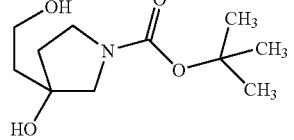 | ESI (+): 408 |
| 47 | 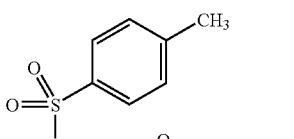 | ESI (+): 114 |
TABLE 15
| Pr | Structure | data |
|---|---|---|
| 48 | 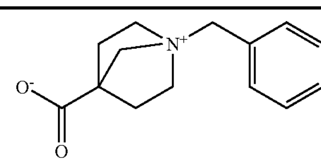 | ESI (+): 232, 254 |

TABLE 15-continued

| Pr | Structure | data |
|---|---|---|
| 49 | ethyl 5-bromo-2-methylthiazole-4-carboxylate | ESI (+): 272, 274 |
| 50 | 3-hydroxy-azabicyclic·HCl | ESI (+): 114 |
| 50-1 | 3-hydroxy-quinuclidine·HCl | ESI (+): 128 |
| 50-2 | 3-hydroxy-quinuclidine isomer·HCl | ESI (+): 128 |
| 51 | ethyl quinolizidine-carboxylate | ESI (+): 198 |
| 51-1 | ethyl quinuclidine-3-carboxylate | ESI (+): 184 |
| 52 | ethyl quinuclidine-3-carboxylate | ESI (+): 184 |
| 52-1 | ethyl 1-benzylazepane-4-carboxylate | ESI (+) 262 |
| 53 | 3-cyano-quinuclidine | SB |
| 54 | methyl quinuclidine-3-carboxylate | SB |
| 55 | ethyl 4-(2-chloroethyl)-1-benzylazepane-4-carboxylate | ESI (+): 324 |

TABLE 16

| Pr | Structure | data |
|---|---|---|
| 56 | ethyl 1-benzylquinuclidinium-3-carboxylate chloride | ESI (+): 288 |
| 57 | bis-Boc/phenethyl protected thiazole carbamate with quinuclidinylmethyl | ESI (+): 577 |

TABLE 16-continued

| Pr | Structure | data |
|---|---|---|
| 57-1 | 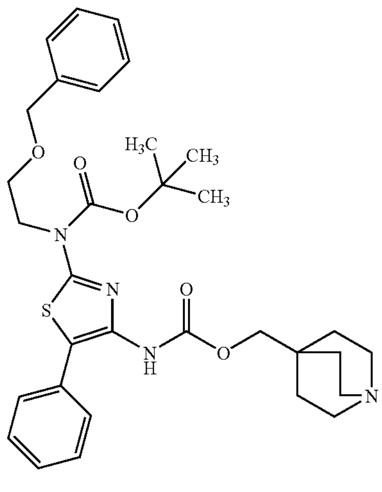 [SMILES: CC(C)(C)OC(=O)N(CCOCc1ccccc1)c1nc(NC(=O)OCC23CCN(CC2)CC3)c(-c2ccccc2)s1] | ESI (+): 593 |
| 57-2 | 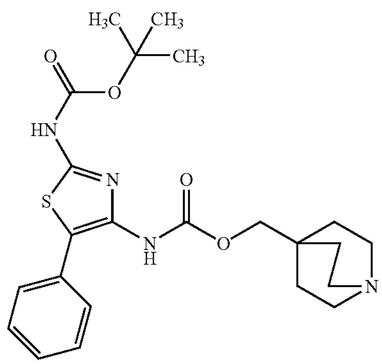 [SMILES: CC(C)(C)OC(=O)Nc1nc(NC(=O)OCC23CCN(CC2)CC3)c(-c2ccccc2)s1] | ESI (+): 459 |
| 57-3 | 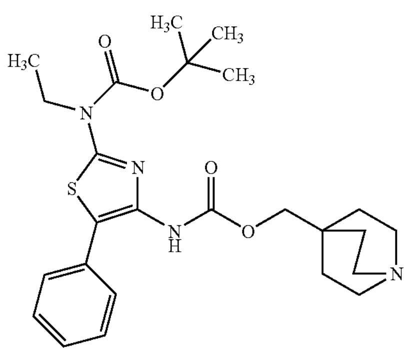 [SMILES: CCN(C(=O)OC(C)(C)C)c1nc(NC(=O)OCC23CCN(CC2)CC3)c(-c2ccccc2)s1] | ESI (+): 487 |

For the sake of saving space in the paper, the descriptions of SB (shown below) in Tables of Production Examples above are denoted as follows.

TABLE 17

| Pr | data |
|---|---|
| 7 | NMR: 1.3-1.37(1H, m), 1.46-1.53(1H, m), 1.57-1.65(1H, m), 1.76(1H, brs), 1.94(1H, brs), 2.55-2.74(5H, m), 3.12(1H, dd, J = 8.3, 14.4 Hz), 4.63-4.67(1H, m), 7.12(1H, d, J = 5.7 Hz), 7.55(1H, d, J = 5.7 Hz), 9.06(1H, brs) |
| 18-9 | NMR(CDCl$_3$): 1.33-1.41(1H, m), 1.65-1.79(3H, m), 2.09-2.13(1H, m), 2.36-2.46(1H, m), 2.52(1H, ddd, J = 2.0, 6.8, 12.4 Hz), 2.74-2.82(4H, m), 2.78-2.95(1H, m), 3.16(1H, dd, J = 10.4, 12.4 Hz), 3.81-3.99(2H, m) |

TABLE 17-continued

| Pr | data |
|---|---|
| 19 | NMR: 3.67(3H, s), 7.41-7.49(5H, m), 7.65(1H, d, J = 5.4 Hz) |
| 25 | NMR(CDCl$_3$): 1.27(3H, t, J = 7.0 Hz), 4.36(2H, q, J = 7.0 Hz), 7.39-7.55(5H, m), 10.03(1H, s). |
| 25-1 | NMR: 1.28(3H, t, J = 7.2 Hz), 4.36(2H, q, J = 7.2 Hz), 7.34-7.54(4H, m), 10.03(1H, s) |
| 53 Low-polarity product | NMR(CDCl$_3$)1.47-1.80(4H, m), 2.65-2.67(1H, m), 2.85-3.01(5H, m), 3.25(1H, dd, J = 5.2, 12.8 Hz), 3.38(1H, ddd, J = 2.0, 8.4, 12.8 Hz), ESI(+): 137 |
| 53 High-polarity product | NMR(CDCl$_3$): 1.48-1.54(1H, m), 1.78-2.01 (3H, m), 2.47-2.50(1H, m), 2.69-2.74(1H, m), 2.87-3.04(4H, m), 3.22(1H, ddd, J = 2.4, 5.2, 13.0 Hz), 3.41(1H, dd, J = 10.8, 13.0 Hz), ESI(+): 137 |
| 54 | NMR(CDCl$_3$): 1.26-1.30(1H, m), 1.67-1.85(3H, m), 2.44-2.47(1H, m), 2.78-2.82(1H, m), 2.87-2.92(3H, m), ESI(+): 170 |

Example 1

To a solution of 1-azabicyclo[2.2.2]oct-4-yl (2-phenyl-3-thienyl)carbamate (120 mg) in DCM (10 mL) was added MCPBA (90 mg) portion wise under ice-cooling. After stirring for 30 minutes, the reaction liquid was concentrated under reduced pressure, and the residue was purified by silica gel column chromatography (CHCl$_3$:MeOH=from 20:1 to 10:1, subjected to liquid separation by 28% aqueous ammonia) to obtain 1-oxide-1-azabicyclo[2.2.2]oct-4-yl(2-phenyl-3-thienyl)carbamate (105 mg) as a colorless amorphous substance.

Example 2

To a solution of 2-phenyl-5,6-dihydro-4H-cyclopenta[b]thiophene-3-amine (110 mg) in pyridine (2 mL) was added (3R)-quinuclidin-3-ol and (3R)-1-azabicyclo[2.2.2]octa-3-yl chlorocarbonate hydrochloride (231 mg) synthesized from triphosgene, followed by stirring at room temperature for 30 minutes, and then stirring at 80° C. for 15 hours. To the reaction mixture was added water, followed by extraction with EtOAc. The organic layer was washed with water and brine in this order, then dried over MgSO$_4$, and concentrated under reduced pressure. The residue was purified by medium-pressure preparative liquid chromatography (silica gel, YAMAZEN YFLC WPrep2XY, CHCl$_3$:MeOH) to obtain a colorless oily substance (135 mg). This was dissolved in EtOH, and fumaric acid (38 mg) was added thereto. The crystal precipitated was collected by filtration to obtain (3R)-1-azabicyclo[2.2.2]oct-3-yl (2-phenyl-5,6-dihydro-4H-cyclopenta[b]thien-3-yl)carbamate fumarate (103 mg) as a white solid.

Example 3

To a solution of triphosgene (362 mg) in DCM (3 mL) was added pyridine (162 mg) at 0° C., and subsequently a solution of cis-2-phenylcyclohexyl amine (300 mg) in DCM (3 mL) was added dropwise thereto, followed by stirring at room temperature for 40 minutes. To a suspension of 60% oily NaH (110 mg) in THF (1.5 mL) was added 1-azabicyclo[2.2.2]oct-3-yl methanol (363 mg) at 0° C., followed by stirring at room temperature for 20 minutes, and to the mixture was added dropwise the above-described DCM solution at 0° C., followed by stirring at 80° C. for 1 hour. To the reaction mixture was added a saturated aqueous NaHCO$_3$ solution, followed by extraction with EtOAc. The organic layer was washed with water and brine in this order, dried over MgSO$_4$, and concentrated under reduced pressure. The residue was purified by silica gel column chromatography (CHCl$_3$:MeOH:28% aqueous ammonia=80:10:1) to obtain a colorless oily substance (100 mg). The oily substance obtained was dissolved in a mixed solvent (EtOAc:EtOH=1:1) and fumaric acid (32 mg) was added thereto. The mixture was concentrated under reduced pressure, a mixed solvent (EtOAc:IPE) was then added thereto, and the solid precipitated was collected by filtration to obtain 1-azabicyclo[2.2.2]oct-3-ylmethyl rel-[(1R,2R)-2-phenylcyclohexyl]carbamate fumarate (103 mg) as a colorless solid.

Example 4

To a solution of 1-azabicyclo[2.2.2]oct-3-ylmethyl (2-phenyl-3-thienyl)carbamate (100 mg) in EtOAc (2 mL) was added iodomethane (36 µL) at room temperature, followed by stirring for overnight. The reaction mixture was filtered, then concentrated under reduced pressure, and freeze-dried to obtain 1-methyl-3-({[(2-phenyl-3-thienyl)carbamoyl]oxy}methyl)-1-azoniabicyclo[2.2.2]octane iodide (88 mg) as a yellow amorphous substance.

Example 5

A solution of a mixture of 1-azabicyclo[2.2.2]oct-3-yl(2-bromo-3-thienyl)carbamate (295 mg), Pd(PPh$_3$)$_4$ (103 mg), 4-fluorophenyl boric acid (187 mg), and 1,4-dioxane (3 mL) was added a 2 M aqueous Na$_2$CO$_3$ solution (0.89 mL), followed by stirring under heating at 90° C. for 5 hours. The reaction mixture was diluted with water, and extracted with EtOAc. The organic layer was washed with water, and adjusted into pH=1 with 1 M hydrochloric acid. Next, the aqueous layer was washed with EtOAc and adjusted to pH=10 with an aqueous NaOH solution, and the aqueous layer was extracted with CHCl$_3$. The organic layer was dried over MgSO$_4$, and concentrated under reduced pressure. The residue was purified by basic silica gel column chromatography (manufactured by Fuji Silysia Chemical Ltd., YAMAZEN YFLC WPrep2XY, CHCl$_3$). The collected fraction was concentrated under reduced pressure and the oil obtained was dissolved in EtOAc, followed by addition of 4 M HCl/EtOAc, concentration under reduced pressure, and solidification to dry. To the residue obtained were added EtOH and EtOAc for crystallization to obtain 1-azabicyclo[2.2.2]oct-3-yl [2-(4-fluorophenyl)-3-thienyl]carbamate hydrochloride (135 mg) as a white solid.

Example 6

To a solution of 5-phenyl-1,3-thiazole-4-carboxylic acid (250 mg) in toluene (6 mL) were added dropwise TEA (221 µL) and DPPA (315 µL) at room temperature, followed by stirring at the same temperature for 40 minutes. Next, after stirring at 90° C. for 40 minutes, a solution of 1-azabicyclo[2.2.2]oct-4-yl methanol (241 mg) in DMF (2 mL)/toluene (2 mL) was added thereto, followed by heating under reflux for 2 hours. To the reaction liquid was added a saturated aqueous NaHCO$_3$ solution, followed by extraction with EtOAc. The organic layer was washed with water and brine in this order, dried over MgSO$_4$, and then filtered, and the filtrate was concentrated under reduced pressure. The residue was purified by medium-pressure preparative liquid chromatography (YAMAZEN YFLC WPrep2XY, eluent; CHCl$_3$:MeOH:28% aqueous ammonia=80:10:1) to obtain a yellow oily substance. To this solution in EtOH (2 mL) was added 4 M HCl/EtOAc (1 mL) at room temperature, followed by stirring, and the solvent was concentrated under reduced pressure. The residue obtained was recrystallized from EtOH/ether to obtain 1-azabicyclo[2.2.2]oct-4-ylmethyl(5-phenyl-1,3-thiazol-4-yl)carbamate hydrochloride (145 mg) as a yellow solid.

Example 7

To a solution of 1-azabicyclo[2.2.2]oct-4-ylmethyl (2-carbamoyl-5-phenyl-1,3 thiazol-4-yl)carbamate (100 mg) in DMF (5 mL) was added phosphorous oxychloride (48 µL) at 0° C., followed by stirring for 1 hour. To the reaction mixture was added EtOAc, followed by dilution, addition of an aqueous NaHCO$_3$ solution, and extraction with EtOAc. The organic layer was washed with water and brine in this order, then dried, and concentrated under reduced pressure. The residue was purified by silica gel column chromatography (CHCl$_3$:MeOH:28% aqueous ammonia=9:1:0.1), and the brown oily substance obtained was dissolved in EtOAc, followed by addition of 4 M HCl/EtOAc and stirring. The mixture was concentrated under reduced pressure, EtOAc was added thereto, and the solid precipitated was collected by filtration to obtain 1-azabicyclo[2.2.2]oct-4-ylmethyl (2-cyano-5-phenyl-1,3-thiazol-4-yl)carbamate hydrochloride (33 mg) as a pale brown solid.

Example 8

1-azabicyclo[2.2.2]oct-3-ylmethyl [5-(4-fluorophenyl)-1,3-thiazol-4-yl]carbamate (120 mg) was subjected to HPLC (CHIRALPAK AD-H, 0.46 cm×25 cm) to separately collect an enantiomer 8a (retention time: about 12.8 minutes, 51 mg) and an enantiomer 8b (retention time: about 16.9 minutes, 54 mg) as a white solid, respectively.

Conditions: mobile phase; hexane:EtOH:diethylamine=50:50:0.1, flow rate; 0.5 mL/minute, column temperature; 40° C., detection wavelength; 254 nm.

Each of the enantiomers was dissolved in EtOH, and fumaric acid was added thereto to yield a fumarate, respectively.

Example 9

In a mixed solvent (MeOH:EtOAc=5 mL:5 mL), to 1-azabicyclo[2.2.2]oct-4-ylmethyl tert-butyl(5-phenyl-1,3-thiazole-2,4-diyl)biscarbamate was added 4 M HCl/EtOAc (7 mL), followed by stirring at room temperature for overnight. The reaction mixture was concentrated under reduced pressure, to the residue was added EtOAc, and the solid was collected by filtration to obtain 1-azabicyclo[2.2.2]oct-4-ylmethyl (2-amino-5-phenyl-1,3-thiazol-4-yl)carbamate dihydrochloride as a white solid.

Example 10

To a solution of 5-phenyl-1,3-thiazole-4-carboxylic acid (300 mg) in toluene (6 mL) were added dropwise TEA (672 µL) and DPPA (409 µL) at room temperature, followed by stirring at the same temperature for 20 minutes. Next, after stirring at 90° C. for 5 minutes, a mixture of 3-aminoquinuclidine dihydrochloride (407 mg) and DMF (2 mL) was added thereto, followed by heating under reflux for 1 hour. To the reaction liquid was added water, followed by extraction with EtOAc. The organic layer was washed with water and brine in this order, dried over MgSO$_4$, and then concentrated under reduced pressure. The residue was purified by medium-pressure preparative liquid chromatography (YAMAZEN YFLC WPrep2XY, eluent; CHCl$_3$:MeOH:28% aqueous ammonia=80:10:1) to obtain an oily substance. This was dissolved in EtOH, followed by addition of 10% HCl/MeOH at room temperature and concentration under reduced pressure. The residue obtained was added with EtOH and EtOAc, and left to stand, and the solid precipitated was collected by filtration, and washed with EtOAc to obtain 1-(1-azabicyclo[2.2.2]oct-3-yl)-3-(5-phenyl-1,3-thiazol-4-yl) urea hydrochloride (15 mg) as a white solid.

Example 11

To a solution of 5-phenyl-1,3-thiazole-4-carboxylic acid (400 mg) in toluene (5 mL) was added TEA (380 µL) at room temperature. To the reaction liquid was added dropwise a solution of DPPA (546 µL) in toluene (5 mL), followed by stirring at the same temperature for 20 minutes. After stirring at 90° C. for 5 minutes, a mixture of 1-azabicyclo [3.2.1]oct-5-yl methanol (357 mg) and DMF (2 mL) was added thereto, followed by heating under reflux for 1 hour. To the reaction liquid was added water, followed by extraction with EtOAc. The organic layer was washed with water and brine in this order, dried over $MgSO_4$, and then concentrated under reduced pressure. The residue was purified by medium-pressure preparative liquid chromatography (YAMAZEN YFLC WPrep2XY, $CHCl_3$:MeOH:28% aqueous ammonia=80:10:1) to obtain an oily substance. This was dissolved in EtOAc, followed by addition of 4 M HCl/dioxane at room temperature. The solid precipitated was collected by filtration and washed with EtOAc to obtain 1-azabicyclo[3.2.1]oct-5-ylmethyl (5-phenyl-1,3-thiazol-4-yl)carbamate hydrochloride (174 mg) as a white solid.

Example 12

To a solution of 5-phenyl-1,3-thiazole-4-carboxylic acid (385 mg) in toluene (5 mL) was added TEA (314 µL) at room temperature. Next, DPPA(486 µL) was added dropwise, followed by stirring at the same temperature for 30 minutes. After stirring at 90° C. for 5 minutes, a mixture of 1-azabicyclo[3.3.1]non-5-yl methanol (291 mg), DMF (1 mL), and toluene (4 mL) was added thereto, followed by stirring at 90° C. for 30 minutes. The reaction mixture was cooled to room temperature, and $CHCl_3$ and water were then added thereto to separate the organic layer. The organic layer was washed with water and brine in this order, dried over $MgSO_4$, and then concentrated under reduced pressure. The residue was purified by medium-pressure preparative liquid chromatography (silica gel, YAMAZEN YFLC WPrep2XY, $CHCl_3$:MeOH:aqueous ammonia). The collected fraction was concentrated under reduced pressure, followed by addition of 4 M HCl/EtOAc and concentration under reduced pressure. To the residue were added EtOAc and water to separate the aqueous layer. The aqueous layer was neutralized with $NaHCO_3$ and extracted with $CHCl_3$. The organic layer was washed with water and brine in this order, dried over $MgSO_4$, and then concentrated under reduced pressure to obtain a tacky substance (129 mg). This was dissolved in EtOH, followed by addition of a solution of fumaric acid (40 mg) in EtOH and concentrated under reduced pressure to obtain 1-azabicyclo[3.3.1]non-5-ylmethyl(5-phenyl-1,3-thiazol-4-yl)carbamate fumarate (161 mg) as a colorless amorphous fluorescent substance.

Example 13

To a mixture of 1-azabicyclo[2.2.2]oct-4-ylmethyl(2-{[2-(benzyloxy)ethyl]amino}-5-phenyl-1,3-thiazol-4-yl)carbamate dihydrochloride (350 mg) and TFA (3.5 mL) was added thioanisole (362 µL) under a nitrogen atmosphere, followed by stirring at room temperature for overnight. The reaction mixture was concentrated under reduced pressure, alkalified with addition of a 1 M aqueous NaOH solution, and extracted with a mixed solvent ($CHCl_3$:MeOH=8:1). The organic layer was dried over $MgSO_4$ and then concentrated under reduced pressure. The residue was purified by medium-pressure preparative liquid chromatography (silica gel, YAMAZEN YFLC WPrep2XY, $CHCl_3$:MeOH:aqueous ammonia). The collected fraction was concentrated under reduced pressure, EtOAc was then added to the residue, and the solid precipitated was pulverized, collected by filtration, and washed with EtOAc to obtain 1-azabicyclo[2.2.2]oct-4-ylmethyl {2-[(2-hydroxyethyl)amino]-5-phenyl-1,3-thiazol-4-yl}carbamate (110 mg) as a colorless solid.

Example 14

To a solution of 5-phenyl-1,3-thiazole-4-carboxylic acid (385 mg) in toluene (8 mL) was added TEA (285 µL) at room temperature. To the reaction mixture was added dropwise DPPA (404 µL), followed by stirring at the same temperature for 40 minutes. In addition, after stirring at 90° C. for 5 minutes, a mixture of 1-azabicyclo[3.2.2]nonan-5-ol (313 mg) and DMF (3 mL) was added thereto, followed by stirring at 110° C. for 1 hour. The reaction mixture was cooled to room temperature, followed by addition with 1 M hydrochloric acid for acidification, and extraction with EtOAc. The aqueous layer was alkalified with addition of a 1 M aqueous NaOH solution, and extracted with $CHCl_3$. The organic layer was washed with water and brine in this order, dried over $MgSO_4$, and then concentrated under reduced pressure. The residue was purified by medium-pressure preparative liquid chromatography (silica gel, YAMAZEN YFLC WPrep2XY, $CHCl_3$:MeOH:aqueous ammonia) to obtain a yellow amorphous fluorescent substance. To this was added EtOAc, and the resulting solid was collected by filtration, and washed with EtOAc to obtain 1-azabicyclo[3.2.2]non-5-yl(5-phenyl-1,3-thiazol-4-yl)carbamate (238 mg) as a colorless powder.

Example 15

A solution of 1-azabicyclo[3.2.1]oct-6-ylmethyl(5-phenyl-1,3-thiazol-4-yl)carbamate in EtOH (1 mL) was prepared, and subjected to preparative HPLC (CHIRALCEL OD, 0.46 cm×25 cm) to separately collect an enantiomer 15a (retention time: about 6.2 minutes) and an enantiomer 15b (retention time: about 7.9 minutes). Each was recrystallized from a mixed solvent (hexane:EtOH) to obtain a colorless solid.

Conditions: mobile phase; hexane:EtOH:diethylamine=50:50:0.1, flow rate; 0.9 mL/minute, column temperature; 40° C., detection wavelength; 254 nm.

By using the above-described preparation method, a method which is apparent to a skilled person in the art, or a modified method thereof, the compounds shown in Tables 18 to 41 below were prepared. The Example numbers (Syn) indicating that the compounds can be prepared in the same manner as the structure of the compounds of Examples are shown in Tables. The physicochemical data are shown in Tables 42 to 57 below.

TABLE 18

| Ex | Syn | Structure |
|---|---|---|
| 1 | — | 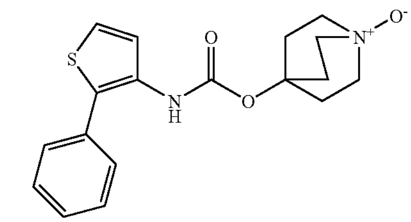 [SMILES: O=C(Nc1ccsc1-c1ccccc1)OC12CC[N+]([O-])(CC1)CC2] |
| 2 | — | 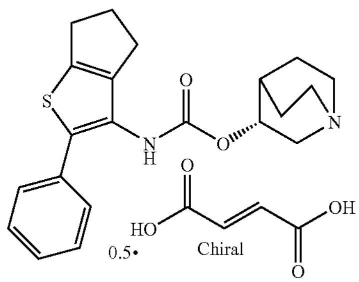 |
| 3 | — | 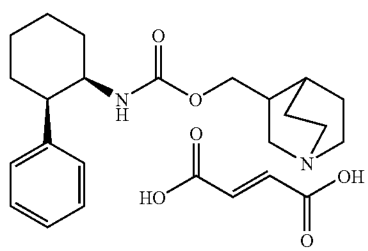 |
| 4 | — | 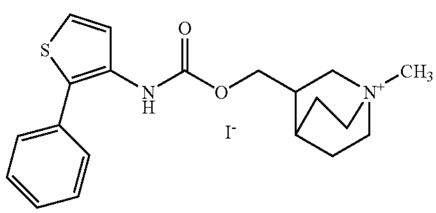 [SMILES: C[N+]12CCC(CC1)C(COC(=O)Nc1ccsc1-c1ccccc1)C2 ; [I-]] |
| 5 | — | 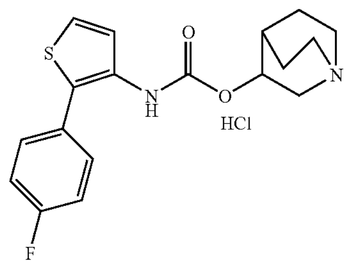 [SMILES: O=C(Nc1ccsc1-c1ccc(F)cc1)OC1CN2CCC1CC2 ; Cl] |
| 6 | — | 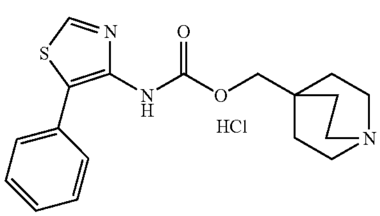 [SMILES: O=C(Nc1ncsc1-c1ccccc1)OCC12CCN(CC1)CC2 ; Cl] |

TABLE 18-continued

| Ex | Syn | Structure |
|---|---|---|
| 7 | — | 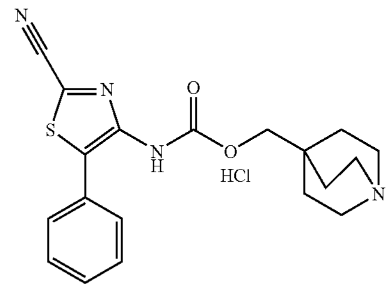 [SMILES: N#Cc1nc(NC(=O)OCC23CCN(CC2)CC3)c(-c2ccccc2)s1 ; Cl] |
| 8a | — | 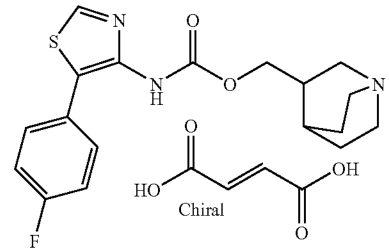 |
| 8b | — | 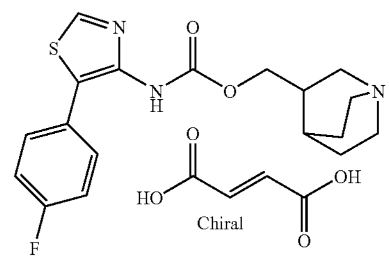 |
| 9 | — | 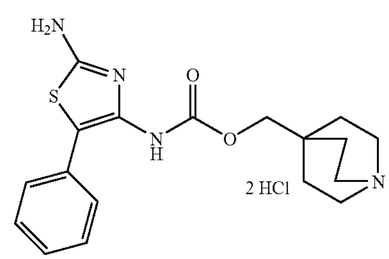 [SMILES: Nc1nc(NC(=O)OCC23CCN(CC2)CC3)c(-c2ccccc2)s1 ; "2 HCl"] |
| 10 | — | 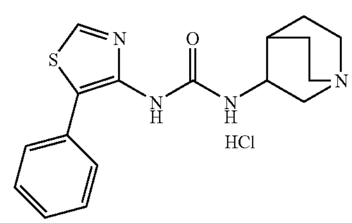 [SMILES: O=C(Nc1ncsc1-c1ccccc1)NC1CN2CCC1CC2 ; Cl] |
| 11 | — | 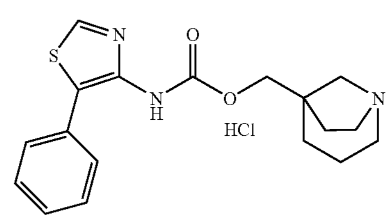 [SMILES: O=C(Nc1ncsc1-c1ccccc1)OCC12CCCN(CC1)C2 ; Cl] |

TABLE 19

| Ex | Syn | Structure |
|---|---|---|
| 12 | — | (structure) |
| 13 | — | (structure) |
| 14 | — | (structure) |
| 15a | — | (structure) |
| 15b | — | (structure) |
| 16 | 2 | (structure) |

TABLE 19-continued

| Ex | Syn | Structure |
|---|---|---|
| 17 | 2 | (structure) |
| 18 | 2 | (structure) |
| 19 | 2 | (structure) |
| 20 | 2 | (structure) |
| 21 | 2 | (structure) |
| 22 | 2 | (structure) |

TABLE 20
| Ex | Syn | Structure |
|---|---|---|
| 23 | 2 | 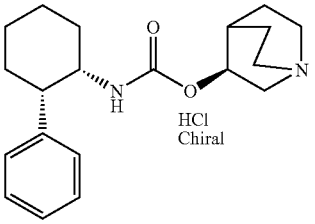 [SMILES: O=C(N[C@H]1CCCC[C@H]1c1ccccc1)O[C@@H]1CN2CCC1CC2] HCl Chiral |
| 24 | 2 | 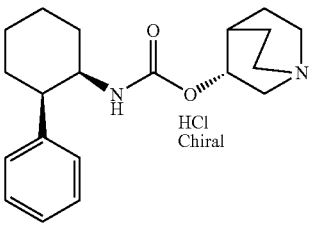 [SMILES: O=C(N[C@@H]1CCCC[C@@H]1c1ccccc1)O[C@H]1CN2CCC1CC2] HCl Chiral |
| 25 | 2 | 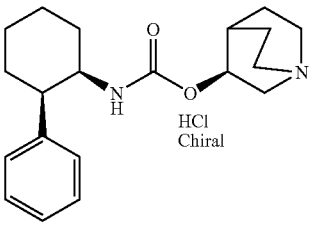 [SMILES: O=C(N[C@@H]1CCCC[C@@H]1c1ccccc1)O[C@@H]1CN2CCC1CC2] HCl Chiral |
| 26 | 2 | 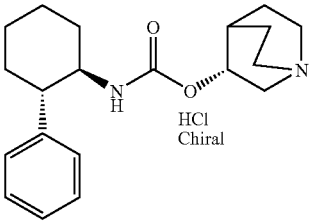 [SMILES: O=C(N[C@@H]1CCCC[C@H]1c1ccccc1)O[C@H]1CN2CCC1CC2] HCl Chiral |
| 27 | 2 | 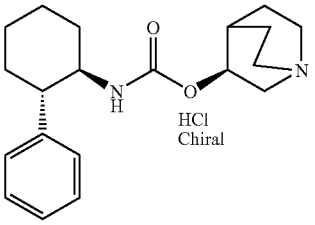 [SMILES: O=C(N[C@@H]1CCCC[C@H]1c1ccccc1)O[C@@H]1CN2CCC1CC2] HCl Chiral |
| 28 | 2 | 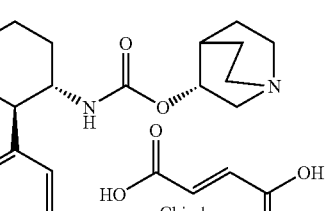 Chiral |
| 29 | 2 | 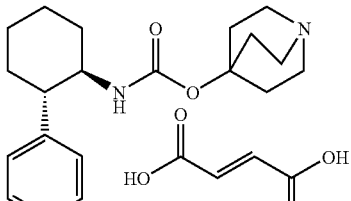 Chiral |
| 30 | 2 | 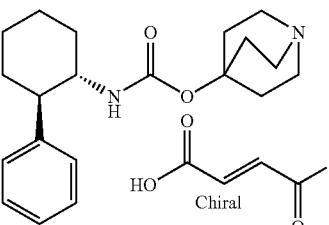 Chiral |
| 31 | 3 | 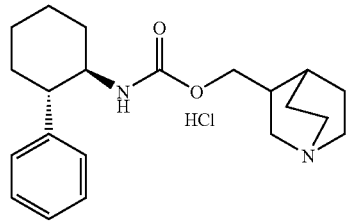 [SMILES: O=C(N[C@@H]1CCCC[C@H]1c1ccccc1)OCC1CN2CCC1CC2 ; Cl] HCl |
| 32 | 4 | 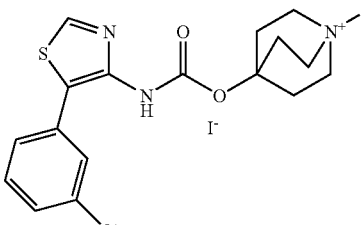 I⁻ |
| 33 | 4 | 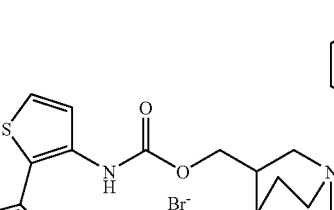 Br⁻ |
| 34 | 4 | 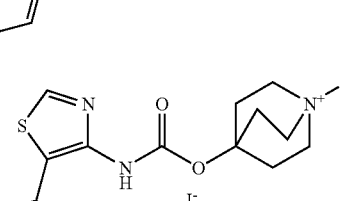 I⁻ |

TABLE 21

| Ex | Syn | Structure |
|---|---|---|
| 35 | 4 | (structure) |
| 36 | 4 | (structure) |
| 37 | 4 | (structure) |
| 38 | 4 | (structure) |
| 39 | 4 | (structure) |
| 40 | 4 | (structure) |
| 41 | 4 | (structure) |
| 42 | 4 | (structure) |
| 43 | 4 | (structure) |
| 44 | 4 | (structure) |

TABLE 21-continued

| Ex | Syn | Structure |
|---|---|---|
| 45 | 4 | 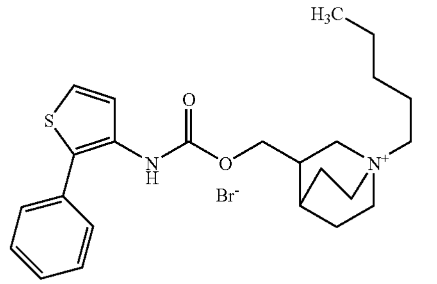 [SMILES: CCCCC[N+]12CCC(CC1)C(COC(=O)Nc1ccsc1-c1ccccc1)C2 ; [Br-]] |
| 46 | 4 | 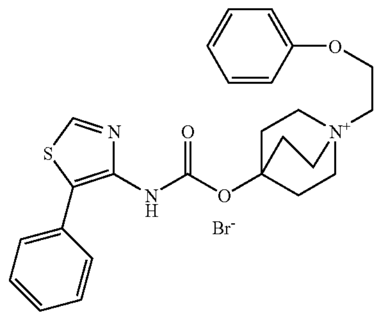 [SMILES: O=C(Nc1ncsc1-c1ccccc1)OC12CC[N+](CCOc3ccccc3)(CC1)CC2 ; [Br-]] |

TABLE 22

| Ex | Syn | Structure |
|---|---|---|
| 47 | 4 | 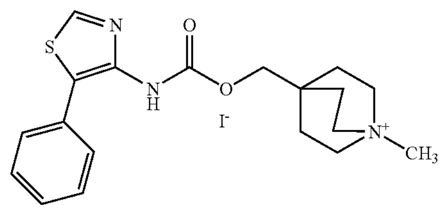 [SMILES: C[N+]12CCC(COC(=O)Nc3ncsc3-c3ccccc3)(CC1)CC2 ; [I-]] |
| 48 | 4 | 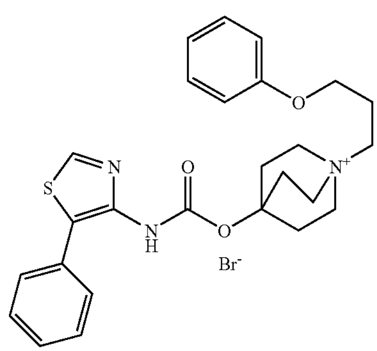 [SMILES: O=C(Nc1ncsc1-c1ccccc1)OC12CC[N+](CCCOc3ccccc3)(CC1)CC2 ; [Br-]] |
| 49 | 4 | 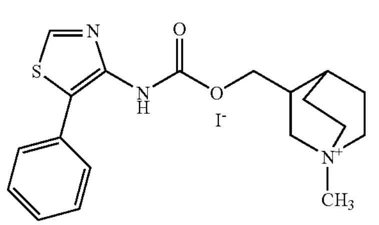 [SMILES: C[N+]12CCC(CC1)C(COC(=O)Nc1ncsc1-c1ccccc1)C2 ; [I-]] |

TABLE 22-continued

| Ex | Syn | Structure |
|---|---|---|
| 50 | 4 | 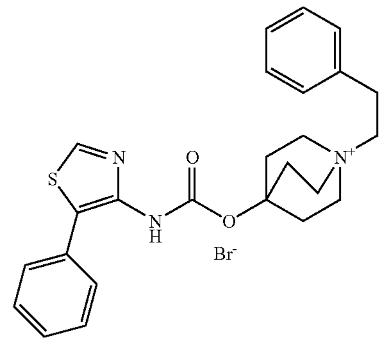 [SMILES: O=C(Nc1ncsc1-c1ccccc1)OC12CC[N+](CCc3ccccc3)(CC1)CC2 ; [Br-]] |
| 51 | 4 | 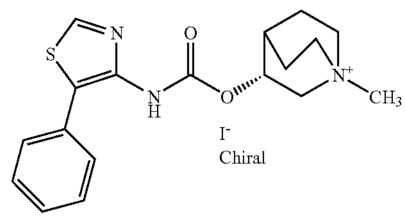 [SMILES: C[N+]12CCC(CC1)[C@@H](OC(=O)Nc1ncsc1-c1ccccc1)C2] |
| 52 | 4 | 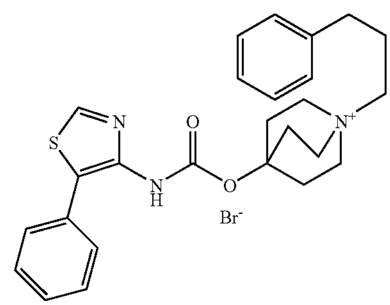 [SMILES: O=C(Nc1ncsc1-c1ccccc1)OC12CC[N+](CCCc3ccccc3)(CC1)CC2 ; [Br-]] |
| 53 | 4 | 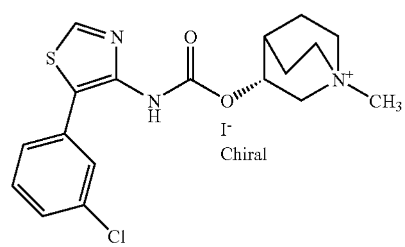 [SMILES: C[N+]12CCC(CC1)[C@@H](OC(=O)Nc1ncsc1-c1cccc(Cl)c1)C2] |
| 54 | 4 | 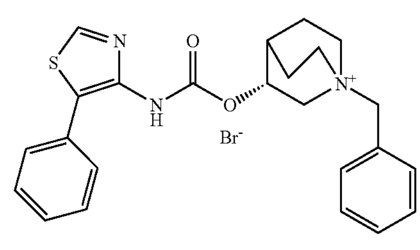 [SMILES: O=C(Nc1ncsc1-c1ccccc1)O[C@H]1C[N+]2(Cc3ccccc3)CCC1CC2 ; [Br-]] |
| 55 | 4 | 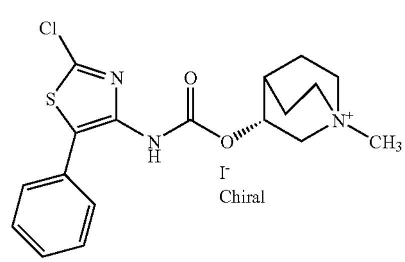 [SMILES: C[N+]12CCC(CC1)[C@@H](OC(=O)Nc1nc(Cl)sc1-c1ccccc1)C2] |

TABLE 22-continued

| Ex | Syn | Structure |
|---|---|---|
| 56 | 4 | 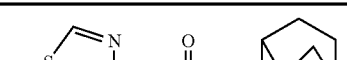 Br⁻ Chiral |

TABLE 23

| Ex | Syn | Structure |
|---|---|---|
| 57 | 4 | (2,5-difluorophenyl thiazole carbamate, 1-methyl piperidinium) I⁻ |
| 58 | 4 | 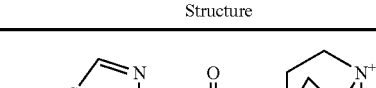 Br⁻ Chiral |
| 59 | 4 | (2,3-difluorophenyl thiazole carbamate, 1-methyl piperidinium) I⁻ |
| 60 | 4 | (phenyl thiazole carbamate, N-(3-phenoxypropyl) piperidinium) Br⁻ Chiral |

TABLE 23-continued

| Ex | Syn | Structure |
|---|---|---|
| 61 | 4 | (2,4-difluorophenyl thiazole carbamate, 1-methyl piperidinium) I⁻ |
| 62 | 4 | (5-chlorothiophene thiazole carbamate, 1-methyl quinuclidinium) I⁻ Chiral |
| 63 | 4 | (2-(difluoromethyl)-5-phenyl thiazole carbamate, 1-methyl piperidinium) I⁻ |
| 64 | 4 | (2-(difluoromethyl)-5-phenyl thiazole carbamate, N-(2-phenoxyethyl) piperidinium) Br⁻ |
| 65 | 4 | (5-phenyl thiazole carbamate, 1-methyl bicyclic ammonium) I⁻ |

TABLE 23-continued

| Ex | Syn | Structure |
|---|---|---|
| 66 | 4 | (structure) |

TABLE 24

| Ex | Syn | Structure |
|---|---|---|
| 67 | 4 | (structure) |
| 68 | 5 | (structure) |
| 69 | 5 | (structure) |
| 70 | 5 | (structure) |
| 71 | 5 | (structure) |

TABLE 24-continued

| Ex | Syn | Structure |
|---|---|---|
| 72 | 5 | (structure) |
| 73 | 5 | (structure) |
| 74 | 5 | (structure) |
| 75 | 5 | (structure) |
| 76 | 5 | (structure) |

TABLE 25

| Ex | Syn | Structure |
|---|---|---|
| 77 | 5 | 4-methyl-2-phenylphenyl carbamate of quinuclidin-3-ol; 0.5 fumarate |
| 78 | 5 | 2-(4-methylphenyl)thiophen-3-yl carbamate of quinuclidin-3-ol; HCl |
| 79 | 5 | 5-fluoro-2-phenylphenyl carbamate of quinuclidin-3-ol; fumarate |
| 80 | 5 | 2-(3-methylphenyl)thiophen-3-yl carbamate of quinuclidin-3-ol; HCl |
| 81 | 5 | 4-fluoro-2-phenylphenyl carbamate of quinuclidin-3-ol; HCl |
| 82 | 5 | 2-(2-methylphenyl)thiophen-3-yl carbamate of quinuclidin-3-ol; HCl |

TABLE 25-continued

| Ex | Syn | Structure |
|---|---|---|
| 83 | 5 | 6-fluoro-2-phenylphenyl carbamate of quinuclidin-3-ol; fumarate |
| 84 | 6 | 5-phenyloxazol-4-yl carbamate of quinuclidin-3-ol; HCl; Chiral |
| 85 | 6 | 2-phenylthiophen-3-yl carbamate of 6-(2-cyclohexylethyl)quinuclidin-3-ol; HCl |
| 86 | 6 | 5-phenyloxazol-4-yl carbamate of quinuclidin-4-ylmethanol; HCl |

TABLE 26

| Ex | Syn | Structure |
|---|---|---|
| 87 | 6 | 2-phenylthiophen-3-yl carbamate of 6-(2-cyclohexylethyl)quinuclidin-3-ol; HCl |

TABLE 26-continued

| Ex | Syn | Structure |
|---|---|---|
| 88 | 6 | 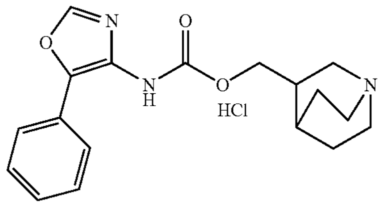 [SMILES: O=C(Nc1ncoc1-c1ccccc1)OCC1CN2CCC1CC2 ; Cl] |
| 89 | 6 | 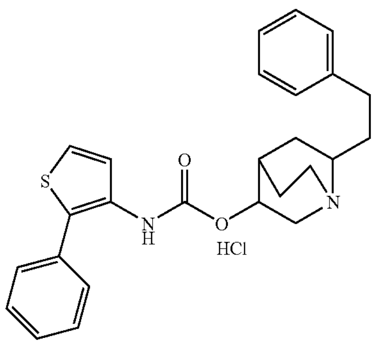 [SMILES: O=C(Nc1ccsc1-c1ccccc1)OC1CN2CCC1CC2CCc1ccccc1 ; Cl] |
| 90 | 6 | 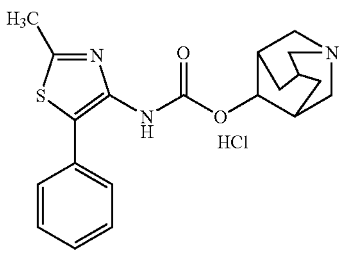 [SMILES: Cc1nc(NC(=O)OC2C3CC4CC2CN(C4)C3)c(-c2ccccc2)s1 ; Cl] |
| 91 | 6 | 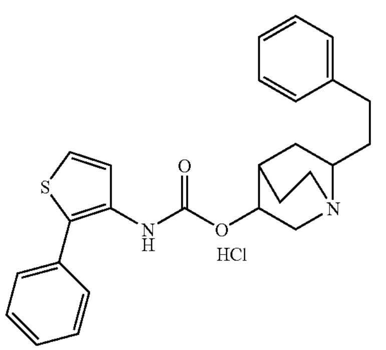 [SMILES: O=C(Nc1ccsc1-c1ccccc1)OC1CN2CCC1CC2CCc1ccccc1 ; Cl] |
| 92 | 6 | 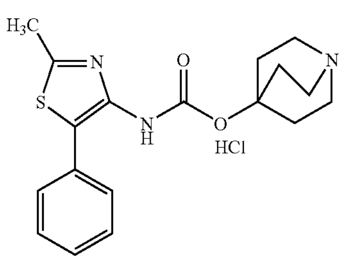 [SMILES: Cc1nc(NC(=O)OC23CCN(CC2)CC3)c(-c2ccccc2)s1 ; Cl] |

TABLE 26-continued

| Ex | Syn | Structure |
|---|---|---|
| 93 | 6 | |
| 94 | 6 | |
| 95 | 6 | |
| 96 | 6 | |

TABLE 27

| Ex | Syn | Structure |
|---|---|---|
| 97 | 6 | 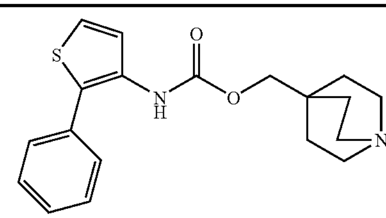 |
| 98 | 6 | 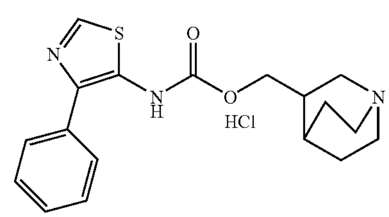 [SMILES: O=C(Nc1scnc1-c1ccccc1)OCC1CN2CCC1CC2 ; Cl] |

TABLE 27-continued

| Ex | Syn | Structure |
|---|---|---|
| 99 | 6 | (thiophene-phenyl carbamate quinuclidine, HCl) |
| 100 | 6 | (thiazole-phenyl carbamate quinuclidinylmethyl) |
| 101 | 6 | (5-chloro-2-phenyl-thiophene carbamate quinuclidinylmethyl) |
| 102 | 6 | (2-methyl-4-phenyl-thiazole carbamate quinuclidinylmethyl, 0.5 fumarate) |
| 103 | 6 | (5-chloro-2-phenyl-thiophene carbamate quinuclidinyl) |
| 104 | 6 | (2-methyl-4-phenyl-thiazole carbamate quinuclidinylmethyl, fumarate) |
| 105 | 6 | (3-phenyl-thiophene-2-carbamate quinuclidine) |
| 106 | 6 | (2-methyl-4-phenyl-thiazole carbamate quinuclidine, 0.5 fumarate) |
| 107 | 6 | (3-phenyl-thiophene-2-carbamate quinuclidinylmethyl) |
| 108 | 6 | (2-methyl-4-phenyl-thiazole carbamate quinuclidinyl, chiral, fumarate) |

TABLE 28

| Ex | Syn | Structure |
|---|---|---|
| 109 | 6 | (3-phenyl-thiophene-2-carbamate quinuclidinylmethyl) |
| 110 | 6 | (5-phenyl-thiazole-4-carbamate quinuclidinyl, HCl) |

TABLE 28-continued
| Ex | Syn | Structure |
|---|---|---|
| 111 | 6 | 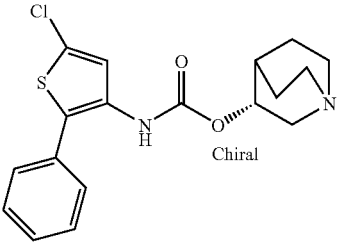 [SMILES: O=C(Nc1cc(Cl)sc1-c1ccccc1)O[C@H]1CN2CCC1CC2] Chiral |
| 112 | 6 | 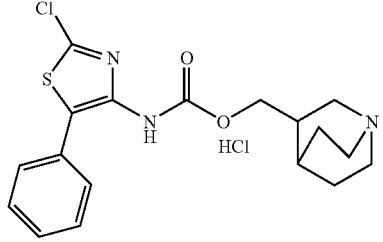 [SMILES: O=C(Nc1nc(Cl)sc1-c1ccccc1)OCC1CN2CCC1CC2 ; Cl] HCl |
| 113 | 6 | 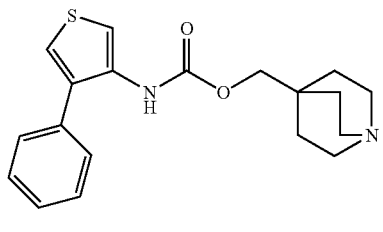 [SMILES: O=C(Nc1cscc1-c1ccccc1)OCC12CCN(CC1)CC2] |
| 114 | 6 | 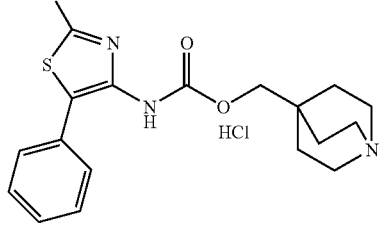 HCl |
| 115 | 6 | 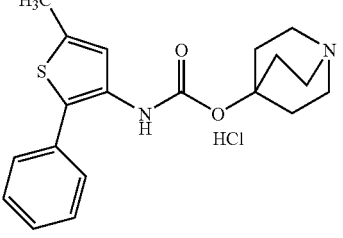 HCl |
| 116 | 6 | 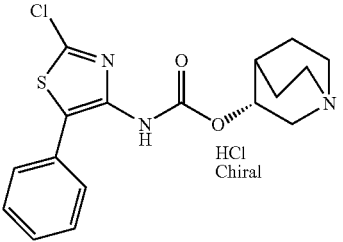 [SMILES: O=C(Nc1nc(Cl)sc1-c1ccccc1)O[C@H]1CN2CCC1CC2] HCl Chiral |
| 117 | 6 | 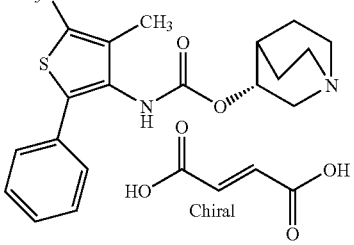 Chiral |
| 118 | 6 | 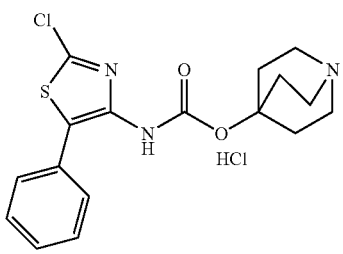 [SMILES: O=C(Nc1nc(Cl)sc1-c1ccccc1)OC12CCN(CC1)CC2 ; Cl] HCl |
| 119 | 6 | 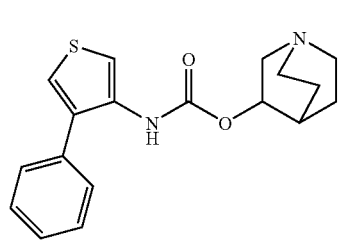 [SMILES: O=C(Nc1cscc1-c1ccccc1)OC1CN2CCC1CC2] |
| 120 | 6 | 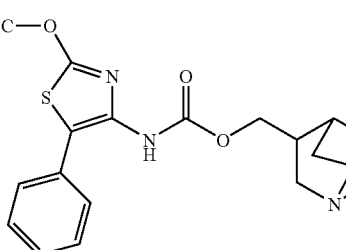 |
TABLE 29
| Ex | Syn | Structure |
|---|---|---|
| 121 | 6 | 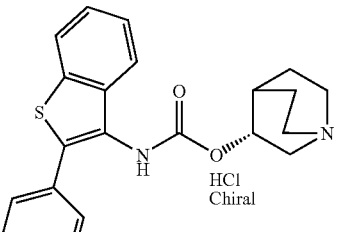 HCl Chiral |

TABLE 29-continued

| Ex | Syn | Structure |
|---|---|---|
| 122 | 6 | 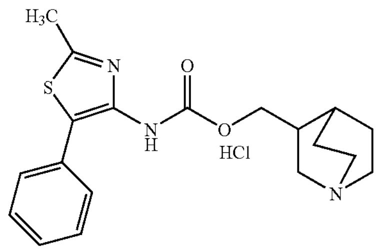 [SMILES: Cc1nc(NC(=O)OCC2CN3CCC2CC3)c(-c2ccccc2)s1 ; Cl] |
| 123 | 6 | 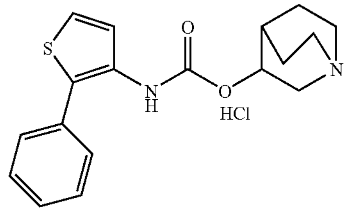 [SMILES: O=C(Nc1ccsc1-c1ccccc1)OC1CN2CCC1CC2 ; Cl] |
| 124 | 6 | 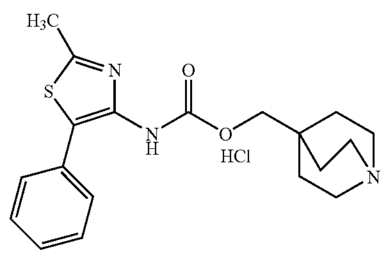 [SMILES: Cc1nc(NC(=O)OCC23CCN(CC2)CC3)c(-c2ccccc2)s1 ; Cl] |
| 125 | 6 | 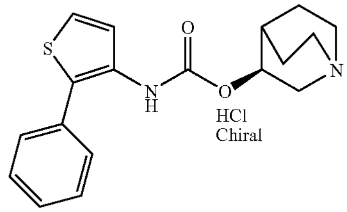 [SMILES: O=C(Nc1ccsc1-c1ccccc1)O[C@@H]1CN2CCC1CC2] |
| 126 | 6 | 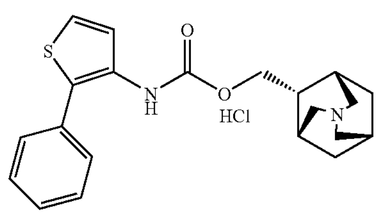 [SMILES: O=C(Nc1ccsc1-c1ccccc1)OC[C@@H]1[C@@H]2C[C@@H]3C[C@H]1CN(C3)C2 ; Cl] |
| 127 | 6 | 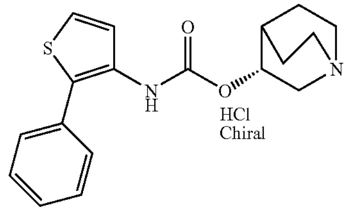 [SMILES: O=C(Nc1ccsc1-c1ccccc1)O[C@H]1CN2CCC1CC2] |
| 128 | 6 | 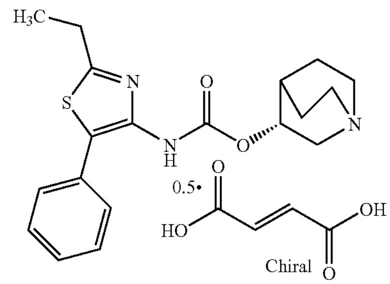 |
| 129 | 6 | 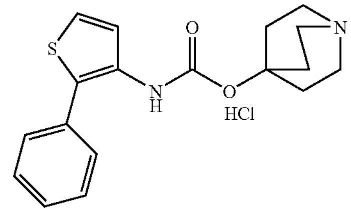 [SMILES: O=C(Nc1ccsc1-c1ccccc1)OC12CCN(CC1)CC2 ; Cl] |
| 130 | 6 | 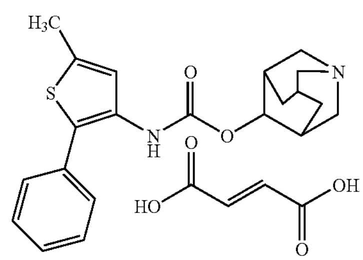 |
| 131 | 6 | 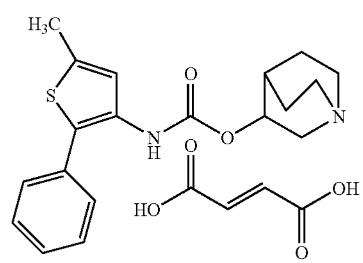 |
| 132 | 6 | 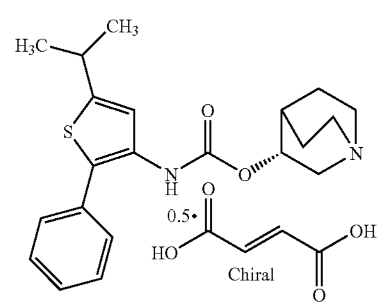 |

TABLE 30

| Ex | Syn | Structure |
|---|---|---|
| 133 | 6 | (structure: 4,5-dimethyl-2-phenylthiophen-3-yl carbamate of quinuclidin-3-ol; 0.5 fumarate) |
| 134 | 6 | (structure: 5-chloro-2-phenylthiophen-3-yl carbamate of quinuclidin-4-ol; HCl) |
| 135 | 6 | (structure: 1-(2-phenylthiophen-3-yl)-3-(quinuclidin-3-yl)urea; 0.5 fumarate) |
| 136 | 6 | (structure: (quinuclidin-3-yl)methyl (2-phenylthiophen-3-yl)carbamate; HCl) |
| 137 | 6 | (structure: 1-(5-chloro-2-phenylthiophen-3-yl)-3-(quinuclidin-3-yl)urea; HCl) |
| 138 | 6 | (structure: quinuclidin-3-yl (5-phenylthiazol-4-yl)carbamate; fumarate) |
| 139 | 6 | (structure: 1-(2-phenylthiophen-3-yl)-3-(quinuclidin-4-yl)urea; 0.5 fumarate) |
| 140 | 6 | (structure: (R)-quinuclidin-3-yl (5-phenylthiazol-4-yl)carbamate; HCl, Chiral) |
| 141 | 6 | (structure: 1-(quinuclidin-4-ylmethyl)-3-(2-phenylthiophen-3-yl)urea) |
| 142 | 6 | (structure: quinuclidin-4-yl (4,5-dimethyl-2-phenylthiophen-3-yl)carbamate; 0.5 fumarate) |
| 143 | 6 | (structure: 1-(5-chloro-2-phenylthiophen-3-yl)-3-(quinuclidin-4-yl)urea) |
| 144 | 6 | (structure: (R)-quinuclidin-3-yl (5-methyl-2-phenylthiophen-3-yl)carbamate; fumarate, Chiral) |

TABLE 31

| Ex | Syn | Structure |
|---|---|---|
| 145 | 6 | (structure) |
| 146 | 6 | (structure) |
| 147 | 6 | (structure) |
| 148 | 6 | (structure) |
| 149 | 6 | (structure) |
| 150 | 6 | (structure) |

TABLE 31-continued

| Ex | Syn | Structure |
|---|---|---|
| 151 | 6 | (structure) |
| 152 | 6 | (structure) |
| 153 | 6 | (structure) |
| 154 | 6 | (structure) |
| 155 | 6 | (structure) |
| 156 | 6 | (structure) |

TABLE 32
| Ex | Syn | Structure |
|---|---|---|
| 157 | 6 | 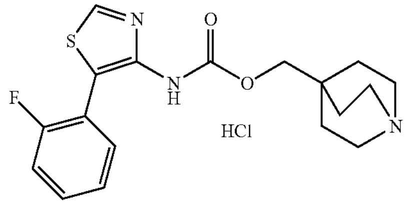 [SMILES: O=C(Nc1ncsc1-c1ccccc1F)OCC12CCN(CC1)CC2 ; Cl] |
| 158 | 6 | 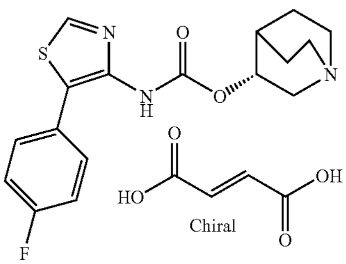 |
| 159 | 6 | 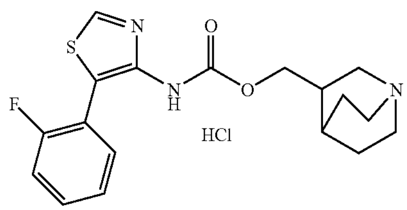 [SMILES: O=C(Nc1ncsc1-c1ccccc1F)OCC1CN2CCC1CC2 ; Cl] |
| 160 | 6 | 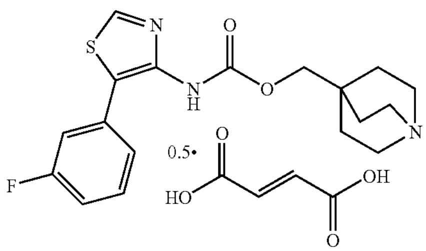 |
| 161 | 6 | 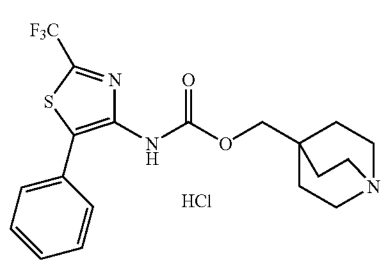 [SMILES: O=C(Nc1nc(C(F)(F)F)sc1-c1ccccc1)OCC12CCN(CC1)CC2 ; Cl] |
| 162 | 6 | 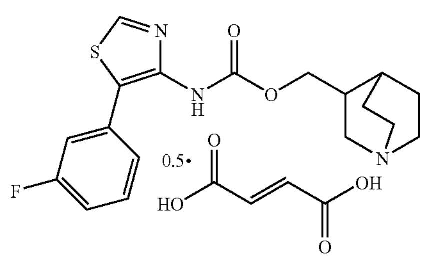 |
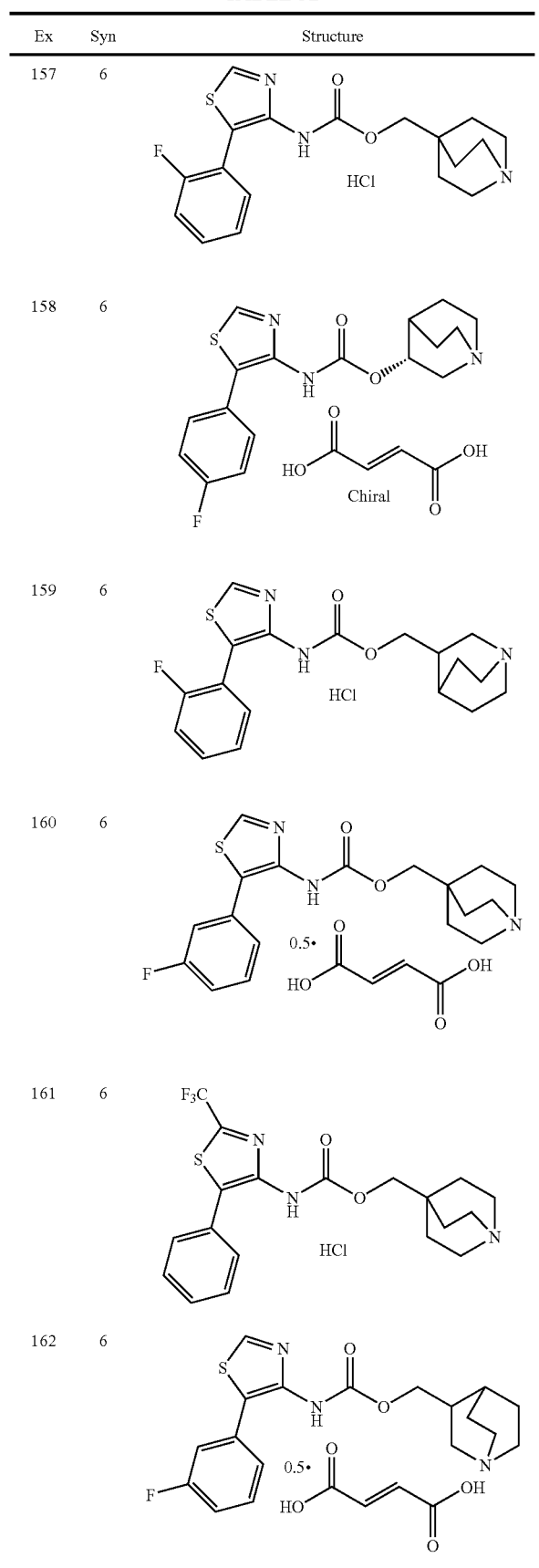
TABLE 32-continued
| Ex | Syn | Structure |
|---|---|---|
| 163 | 6 | 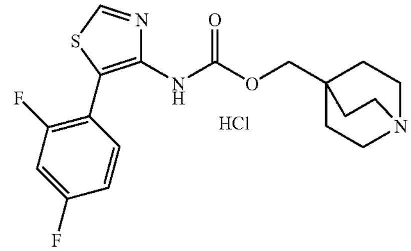 [SMILES: O=C(Nc1ncsc1-c1ccc(F)cc1F)OCC12CCN(CC1)CC2 ; Cl] |
| 164 | 6 | 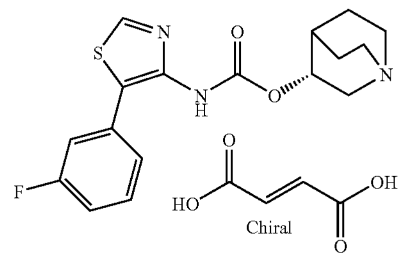 |
| 165 | 6 | 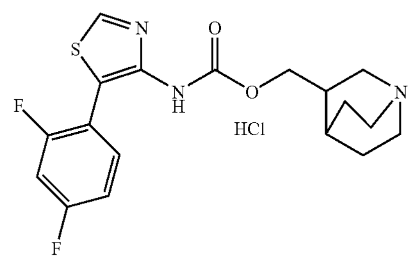 [SMILES: O=C(Nc1ncsc1-c1ccc(F)cc1F)OCC1CN2CCC1CC2 ; Cl] |
| 166 | 6 | 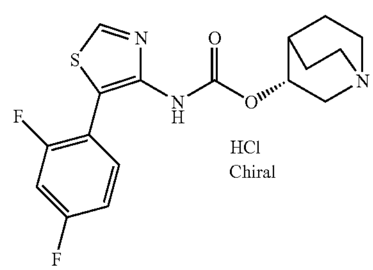 [SMILES: O=C(Nc1ncsc1-c1ccc(F)cc1F)O[C@H]1CN2CCC1CC2 ; Cl] |
| 167 | 6 | 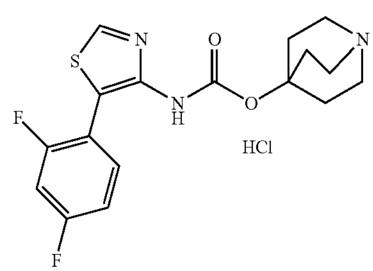 [SMILES: O=C(Nc1ncsc1-c1ccc(F)cc1F)OC12CCN(CC1)CC2 ; Cl] |
| 168 | 6 | 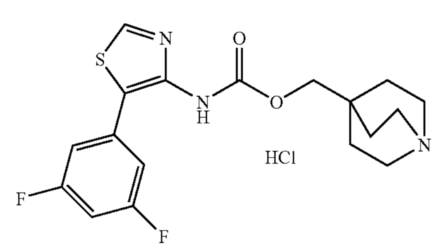 [SMILES: O=C(Nc1ncsc1-c1cc(F)cc(F)c1)OCC12CCN(CC1)CC2 ; Cl] |
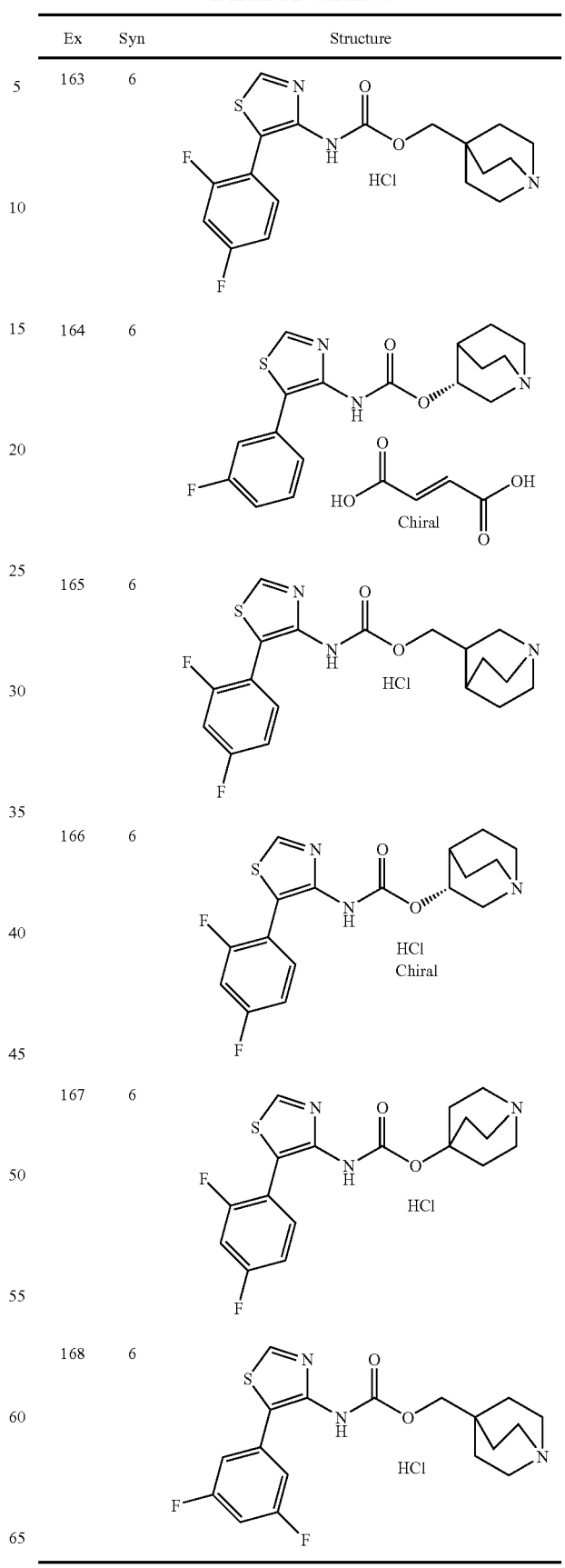

TABLE 33
| Ex | Syn | Structure |
|---|---|---|
| 169 | 6 | 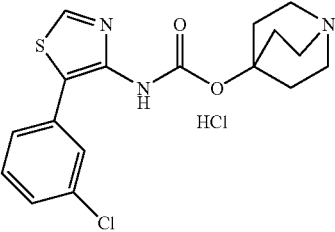 [SMILES: O=C(Nc1ncsc1-c1cccc(Cl)c1)OC12CCN(CC1)CC2 ; Cl] HCl |
| 170 | 6 | 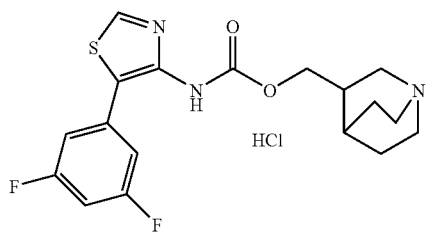 [SMILES: O=C(Nc1ncsc1-c1cc(F)cc(F)c1)OCC1CN2CCC1CC2 ; Cl] HCl |
| 171 | 6 | 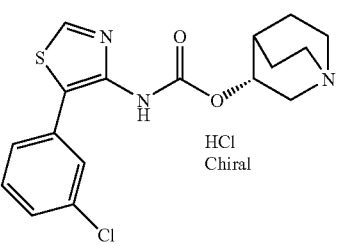 HCl Chiral |
| 172 | 6 | 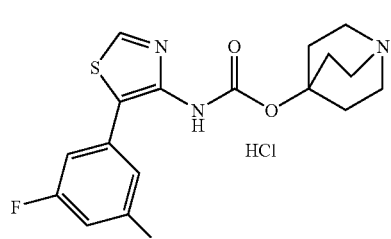 HCl |
| 173 | 6 | 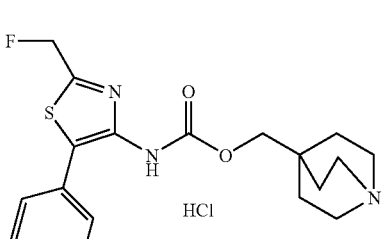 HCl |
| 174 | 6 | 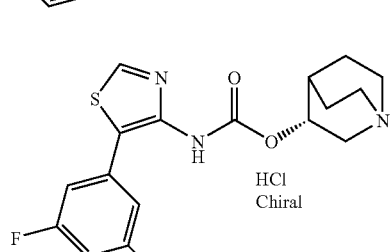 HCl Chiral |
TABLE 33-continued
| Ex | Syn | Structure |
|---|---|---|
| 175 | 6 | 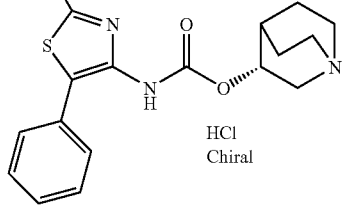 HCl Chiral |
| 176 | 6 | 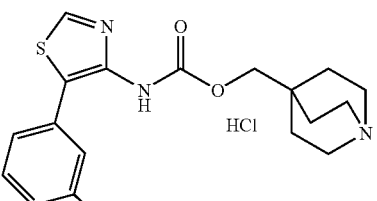 HCl |
| 177 | 6 | 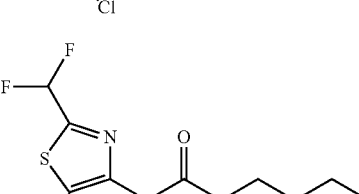 HCl |
| 178 | 6 | 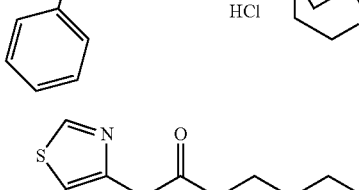 HCl |
| 179 | 6 | 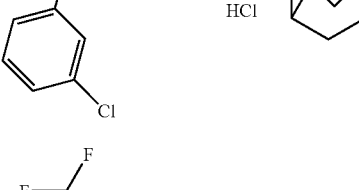 HCl Chiral |
| 180 | 6 | 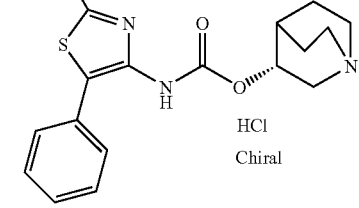 0.5· 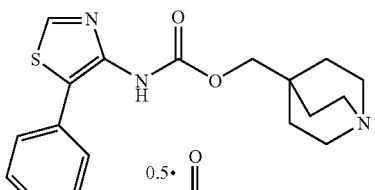 |

TABLE 34
| Ex | Syn | Structure |
|---|---|---|
| 181 | 6 | 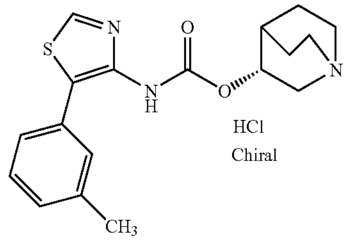 [SMILES: Cc1cccc(-c2scnc2NC(=O)O[C@H]2CN3CCC2CC3)c1 ; Cl] |
| 182 | 6 | 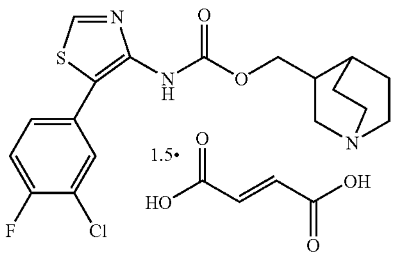 |
| 183 | 6 | 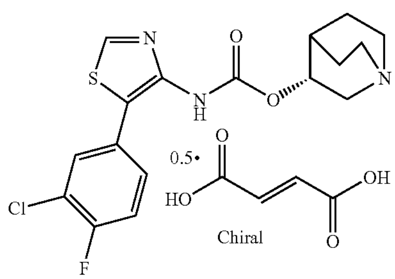 |
| 184 | 6 | 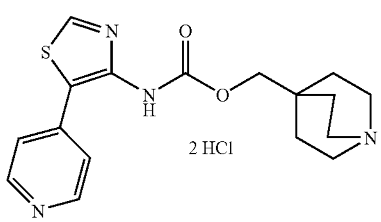 [SMILES: O=C(Nc1ncsc1-c1ccncc1)OCC12CCN(CC1)CC2 ; "2 HCl"] |
| 185 | 6 | 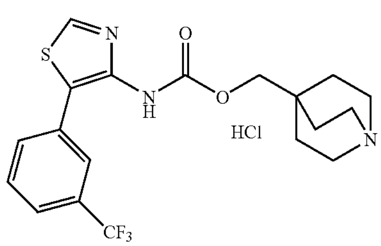 [SMILES: O=C(Nc1ncsc1-c1cccc(C(F)(F)F)c1)OCC12CCN(CC1)CC2 ; Cl] |
| 186 | 6 | 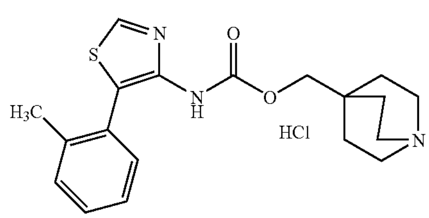 [SMILES: Cc1ccccc1-c1scnc1NC(=O)OCC12CCN(CC1)CC2 ; Cl] |
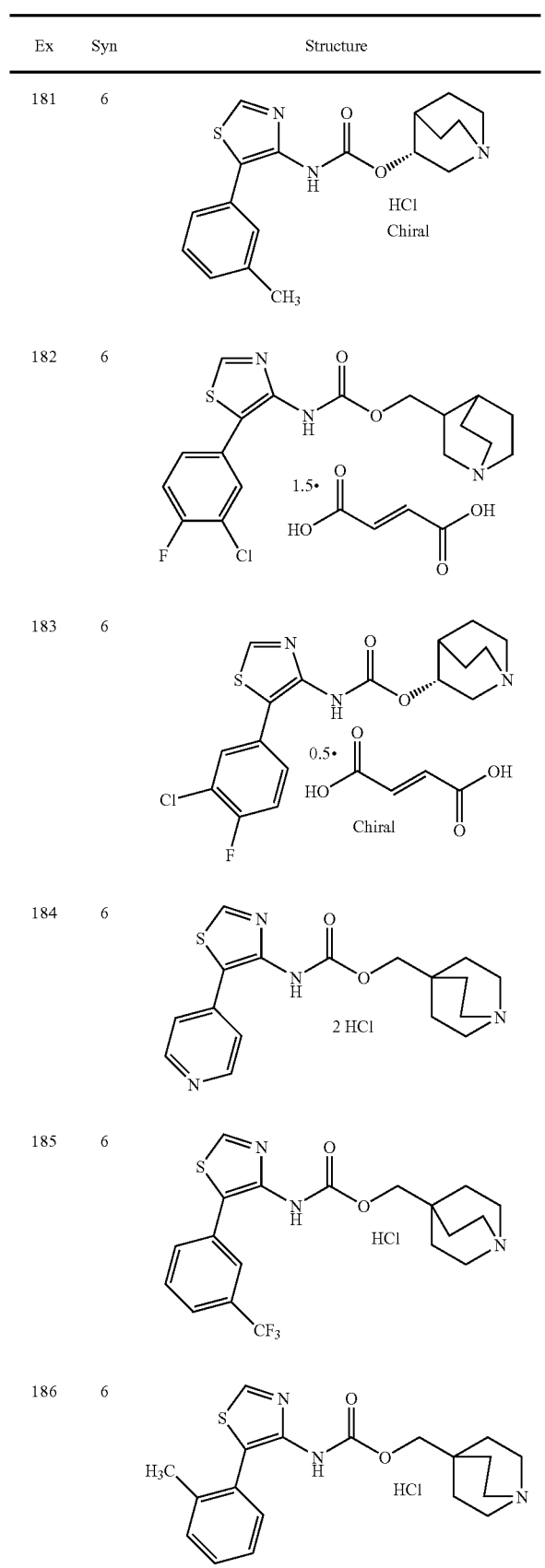
TABLE 34-continued
| Ex | Syn | Structure |
|---|---|---|
| 187 | 6 | 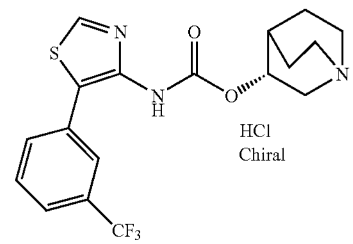 [SMILES: O=C(Nc1ncsc1-c1cccc(C(F)(F)F)c1)O[C@H]1CN2CCC1CC2 ; Cl] |
| 188 | 6 | 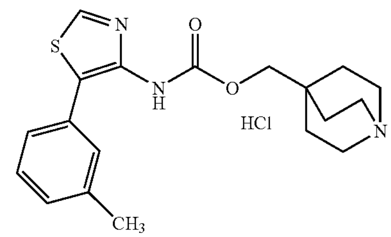 [SMILES: Cc1cccc(-c2scnc2NC(=O)OCC23CCN(CC2)CC3)c1 ; Cl] |
| 189 | 6 | 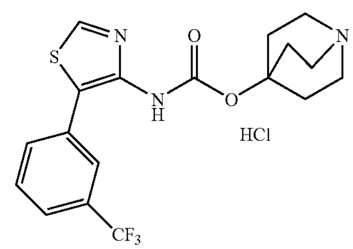 [SMILES: O=C(Nc1ncsc1-c1cccc(C(F)(F)F)c1)OC12CCN(CC1)CC2 ; Cl] |
| 190 | 6 | 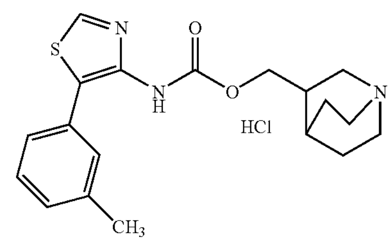 [SMILES: Cc1cccc(-c2scnc2NC(=O)OCC2CN3CCC2CC3)c1 ; Cl] |
| 191 | 6 | 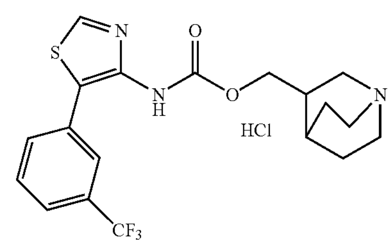 [SMILES: O=C(Nc1ncsc1-c1cccc(C(F)(F)F)c1)OCC1CN2CCC1CC2 ; Cl] |
| 192 | 6 | 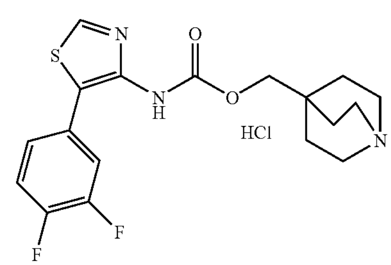 [SMILES: O=C(Nc1ncsc1-c1ccc(F)c(F)c1)OCC12CCN(CC1)CC2 ; Cl] |
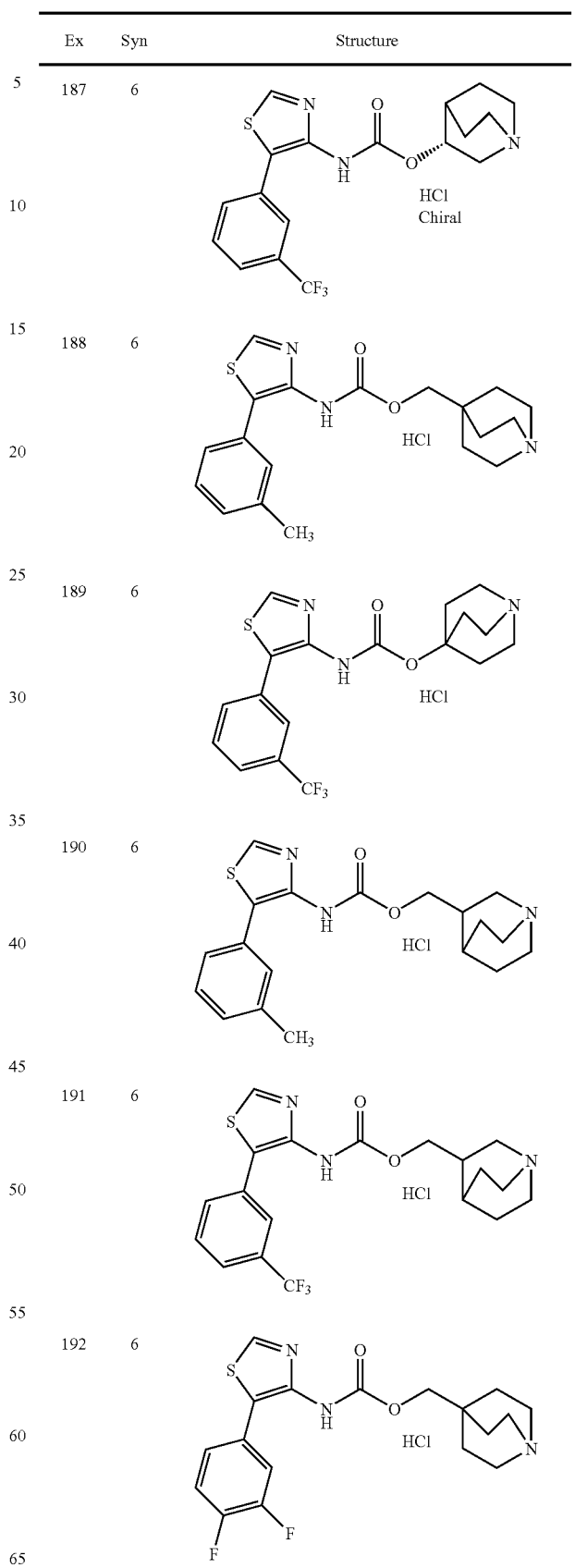

TABLE 35
| Ex | Syn | Structure |
|---|---|---|
| 193 | 6 | 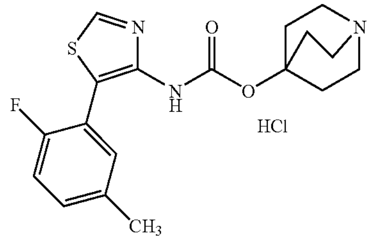 [SMILES: Cc1ccc(F)c(-c2scnc2NC(=O)OC23CCN(CC2)CC3)c1 ; Cl] |
| 194 | 6 | 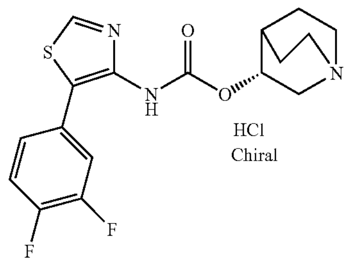 [SMILES: O=C(Nc1ncsc1-c1ccc(F)c(F)c1)O[C@H]1CN2CCC1CC2 ; Cl] |
| 195 | 6 | 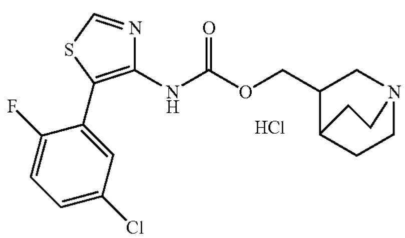 [SMILES: O=C(Nc1ncsc1-c1cc(Cl)ccc1F)OCC1CN2CCC1CC2 ; Cl] |
| 196 | 6 | 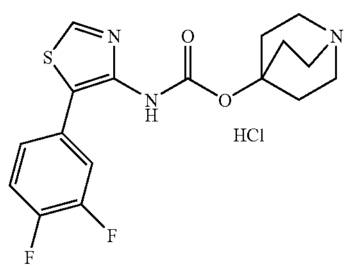 [SMILES: O=C(Nc1ncsc1-c1ccc(F)c(F)c1)OC12CCN(CC1)CC2 ; Cl] |
| 197 | 6 | 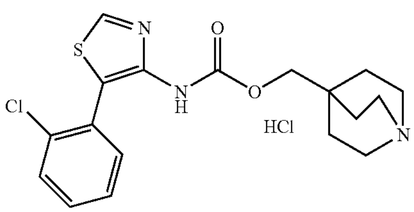 [SMILES: O=C(Nc1ncsc1-c1ccccc1Cl)OCC12CCN(CC1)CC2 ; Cl] |
| 198 | 6 | 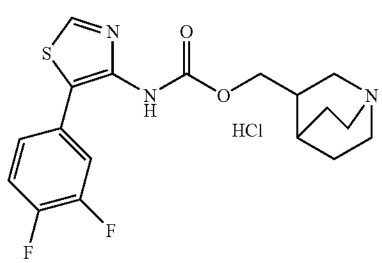 [SMILES: O=C(Nc1ncsc1-c1ccc(F)c(F)c1)OCC1CN2CCC1CC2 ; Cl] |
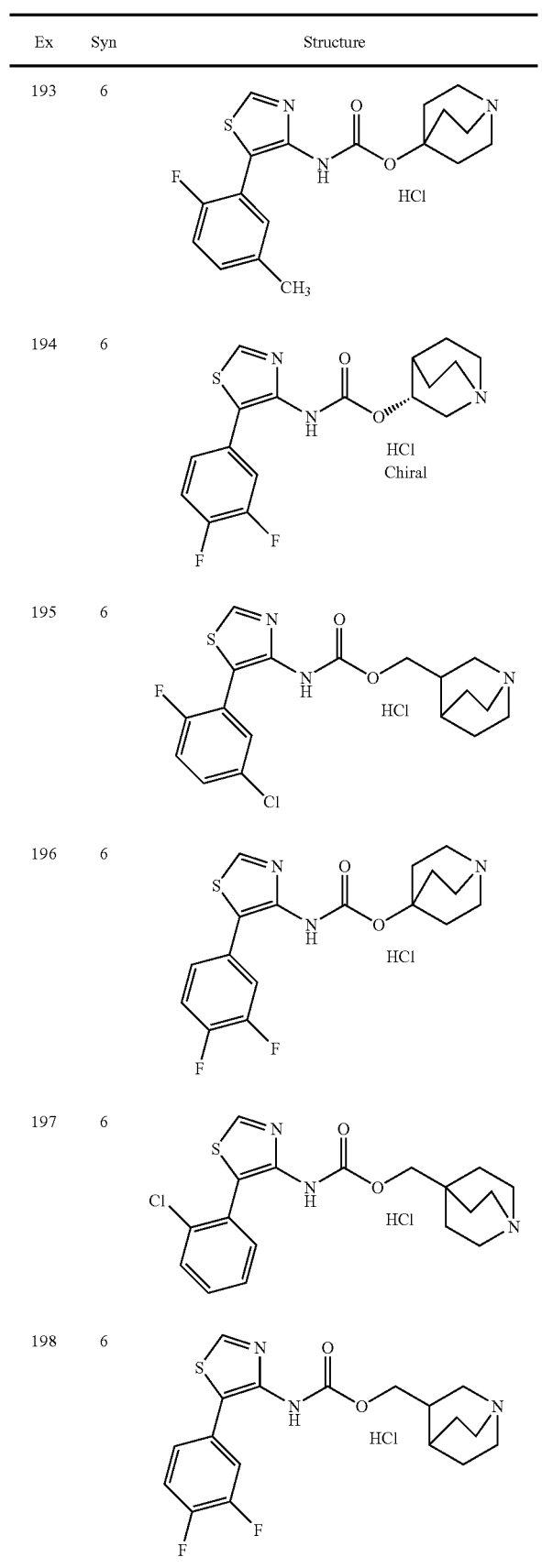
TABLE 35-continued
| Ex | Syn | Structure |
|---|---|---|
| 199 | 6 | 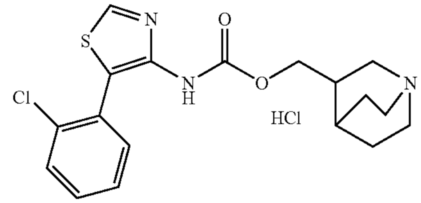 [SMILES: O=C(Nc1ncsc1-c1ccccc1Cl)OCC1CN2CCC1CC2 ; Cl] |
| 200 | 6 | 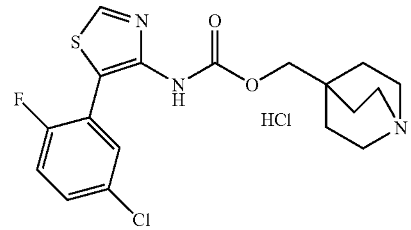 [SMILES: O=C(Nc1ncsc1-c1cc(Cl)ccc1F)OCC12CCN(CC1)CC2 ; Cl] |
| 201 | 6 | 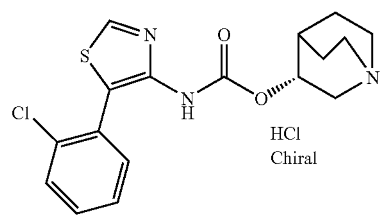 [SMILES: O=C(Nc1ncsc1-c1ccccc1Cl)O[C@H]1CN2CCC1CC2 ; Cl] |
| 202 | 6 | 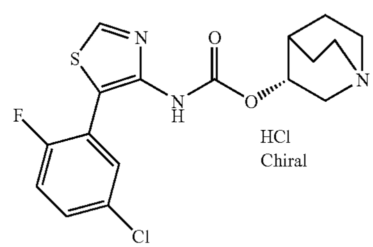 [SMILES: O=C(Nc1ncsc1-c1cc(Cl)ccc1F)O[C@H]1CN2CCC1CC2 ; Cl] |
| 203 | 6 | 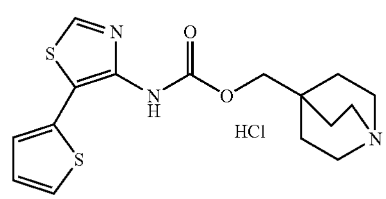 [SMILES: O=C(Nc1ncsc1-c1cccs1)OCC12CCN(CC1)CC2 ; Cl] |
| 204 | 6 | 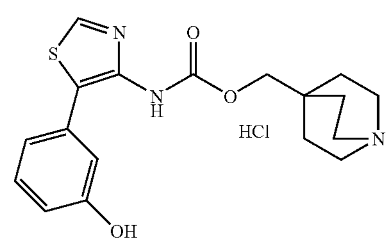 [SMILES: O=C(Nc1ncsc1-c1cccc(O)c1)OCC12CCN(CC1)CC2 ; Cl] |
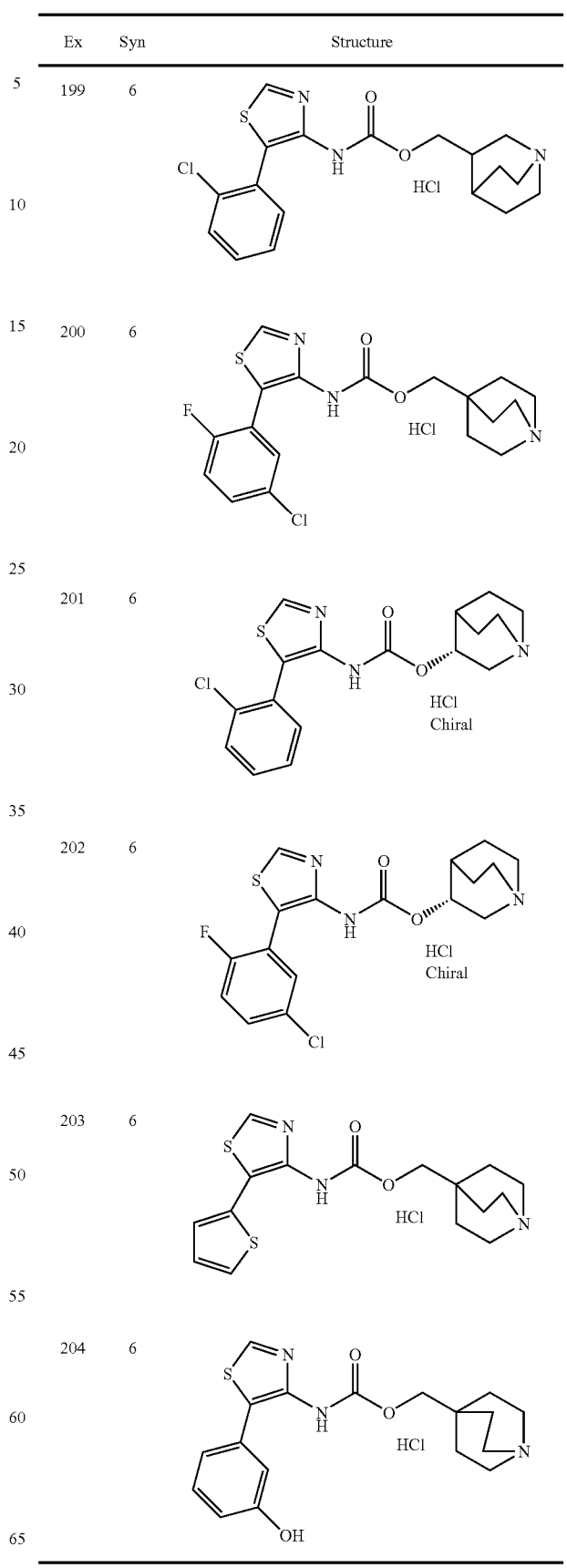

TABLE 36

| Ex | Syn | Structure |
|---|---|---|
| 205 | 6 | thiazole-thiophene carbamate quinuclidine, HCl |
| 206 | 6 | thiazole-(3-hydroxyphenyl) carbamate quinuclidine, 1.5 fumarate |
| 207 | 6 | thiazole-(4-fluoro-3-methylphenyl) carbamate quinuclidine, fumarate |
| 208 | 6 | thiazole-(2-methylphenyl) carbamate quinuclidin-3-yl, HCl |
| 209 | 6 | thiazole-(4-fluoro-3-methylphenyl) carbamate quinuclidine, 1.5 fumarate |
| 210 | 6 | thiazole-(2-methylphenyl) carbamate quinuclidine, HCl |

TABLE 36-continued

| Ex | Syn | Structure |
|---|---|---|
| 211 | 6 | thiazole-(4-fluoro-3-methylphenyl) carbamate (R)-quinuclidin-3-yl, 0.5 fumarate, Chiral |
| 212 | 6 | thiazole-(2,6-difluorophenyl) carbamate quinuclidine |
| 213 | 6 | thiazole-(4-fluoro-3-methylphenyl) carbamate (S)-quinuclidin-3-yl, 0.5 fumarate |
| 214 | 6 | thiazole-(2,6-difluorophenyl) carbamate quinuclidin-3-yl, HCl, Chiral |
| 215 | 6 | 2-bromo-5-phenyl-thiazole carbamate quinuclidine, fumarate |
| 216 | 6 | thiazole-(2-methylphenyl) carbamate quinuclidin-4-yl |

TABLE 37

| Ex | Syn | Structure |
|---|---|---|
| 217 | 6 | 2-bromo-5-phenyl-thiazol-4-yl carbamate of (R)-quinuclidin-3-ol; fumarate; Chiral |
| 218 | 6 | 5-(3-cyanophenyl)-thiazol-4-yl carbamate of (R)-quinuclidin-3-ol; fumarate; Chiral |
| 219 | 6 | 5-(3-chloro-5-fluorophenyl)-thiazol-4-yl carbamate of quinuclidin-3-yl-methanol |
| 220 | 6 | 5-(3-cyanophenyl)-thiazol-4-yl carbamate of 1-azabicyclo[2.2.2]oct-4-yl-methanol; 1.5 fumarate |
| 221 | 6 | 5-(1-methyl-1H-pyrazol-4-yl)-thiazol-4-yl carbamate of 1-azabicyclo[2.2.2]oct-4-yl-methanol; HCl |
| 222 | 6 | 5-(3-cyanophenyl)-thiazol-4-yl carbamate of 1-azabicyclo[2.2.2]oct-4-yl-methanol; 0.5 fumarate |

TABLE 37-continued

| Ex | Syn | Structure |
|---|---|---|
| 223 | 6 | 5-(1-methyl-1H-pyrazol-4-yl)-thiazol-4-yl carbamate of (R)-quinuclidin-3-ol; HCl; Chiral |
| 224 | 6 | 5-(2,6-difluorophenyl)-thiazol-4-yl carbamate of 1-azabicyclo[2.2.2]oct-4-yl-methanol; HCl |
| 225 | 6 | 2-carbamoyl-5-phenyl-thiazol-4-yl carbamate of 1-azabicyclo[2.2.2]oct-4-yl-methanol; HCl |
| 226 | 6 | 5-(3-chloro-5-fluorophenyl)-thiazol-4-yl carbamate of 1-azabicyclo[2.2.2]oct-4-yl-methanol; HCl |
| 227 | 6 | 5-(thiophen-2-yl)-thiazol-4-yl carbamate of (R)-quinuclidin-3-ol; HCl; Chiral |
| 228 | 6 | 5-(3-cyano-4-fluorophenyl)-thiazol-4-yl carbamate of 1-azabicyclo[2.2.2]oct-4-yl-methanol; 0.5 fumarate |

TABLE 38

| Ex | Syn | Structure |
|---|---|---|
| 229 | 6 | (thiazole-phenyl(F,CN) carbamate methyl-quinuclidine; 0.5· fumaric acid) |
| 230 | 6 | (thiazole-phenyl(F,CN) carbamate quinuclidin-3-yloxy; fumaric acid; Chiral) |
| 231 | 6 | (thiazole-(3,5-dichlorophenyl) carbamate quinuclidin-3-yloxy; 1.5· fumaric acid; Chiral) |
| 232 | 6 | (thiazole-phenyl(F,CN) carbamate quinuclidin-4-yloxy; fumaric acid) |
| 233 | 6 | (thiazole-(3,5-dichlorophenyl) carbamate quinuclidin-4-yloxy; 0.5· fumaric acid) |
| 234 | 6 | (thiazole-phenyl(F,CN) carbamate N-methyl-quinuclidinium; I⁻) |

TABLE 38-continued

| Ex | Syn | Structure |
|---|---|---|
| 235 | 6 | (thiazole-(2,6-difluorophenyl) carbamate quinuclidin-4-yloxy) |
| 236 | 6 | (thiazole-(3,5-dichlorophenyl) carbamate methyl-quinuclidine; fumaric acid) |
| 237 | 6 | (thiazole-(pyridin-3-yl) carbamate methyl-quinuclidine; 2 HCl) |
| 238 | 6 | (thiazole-(3,5-dichlorophenyl) carbamate methyl-quinuclidine; 0.5· fumaric acid) |
| 239 | 6 | (thiazole-pyrazinyl carbamate methyl-quinuclidine; HCl) |
| 240 | 6 | (thiazole-(5-chlorothiophen-2-yl) carbamate methyl-quinuclidine; HCl) |

TABLE 39
| Ex | Syn | Structure |
|----|-----|-----------|
| 241 | 6 | 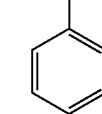 |
| 242 | 6 | 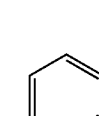 |
| 243 | 6 | 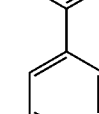 |
| 244 | 6 | 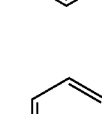 |
| 245 | 6 | 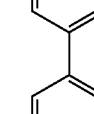 |
| 246 | 6 | 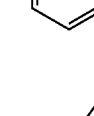 |
TABLE 39-continued
| Ex | Syn | Structure |
|----|-----|-----------|
| 247 | 6 | 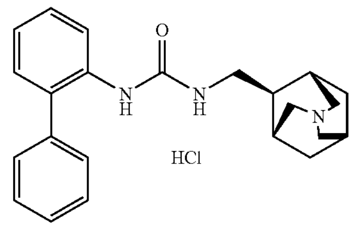 [SMILES: O=C(NC[C@H]1[C@@H]2C[C@@H]3C[C@H]1CN(C3)C2)Nc1ccccc1-c1ccccc1 ; Cl] |
| 248 | 6 | 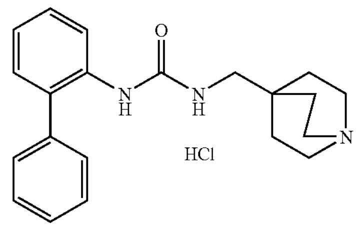 [SMILES: O=C(NCC12CCN(CC1)CC2)Nc1ccccc1-c1ccccc1 ; Cl] |
| 249 | 6 | 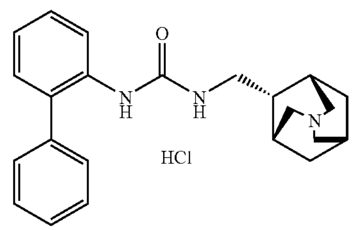 [SMILES: O=C(NC[C@@H]1[C@@H]2C[C@@H]3C[C@H]1CN(C3)C2)Nc1ccccc1-c1ccccc1 ; Cl] |
| 250 | 6 | 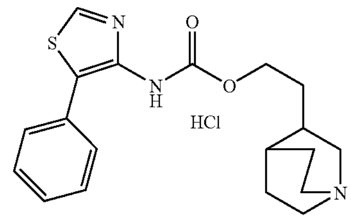 [SMILES: O=C(Nc1ncsc1-c1ccccc1)OCCC1CN2CCC1CC2 ; Cl] |
| 251 | 6 | 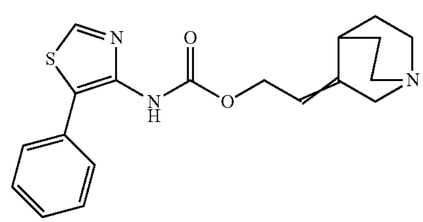 [SMILES: O=C(Nc1ncsc1-c1ccccc1)OCC=C1CN2CCC1CC2] |
| 252 | 6 | 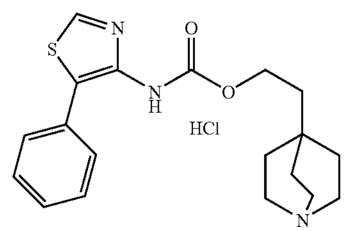 [SMILES: O=C(Nc1ncsc1-c1ccccc1)OCCC12CCN(CC1)CC2 ; Cl] |

TABLE 40
| Ex | Syn | Structure |
|----|-----|-----------|
| 253 | 6 | 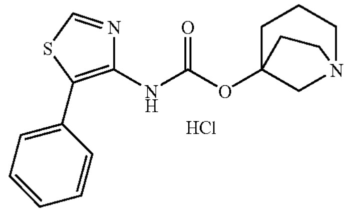 [SMILES: O=C(Nc1ncsc1-c1ccccc1)OC12CCCN(CC1)C2 ; Cl] |
| 254 | 6 | 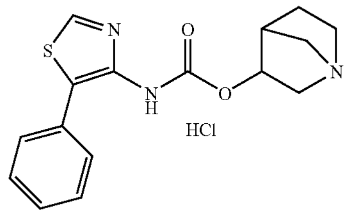 [SMILES: O=C(Nc1ncsc1-c1ccccc1)OC1CN2CCC1C2 ; Cl] |
| 255 | 6 | 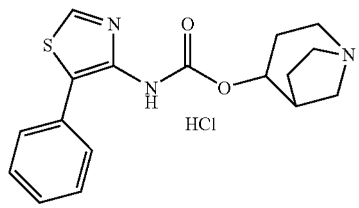 [SMILES: O=C(Nc1ncsc1-c1ccccc1)OC1CCN2CCC1C2 ; Cl] |
| 256 | 9 | 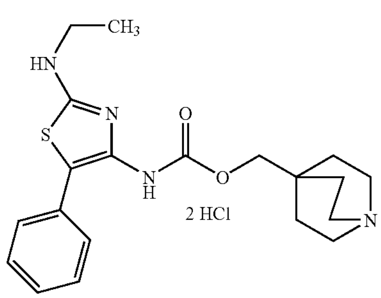 [SMILES: CCNc1nc(NC(=O)OCC23CCN(CC2)CC3)c(-c2ccccc2)s1 ; "2 HCl"] |
| 257 | 9 | 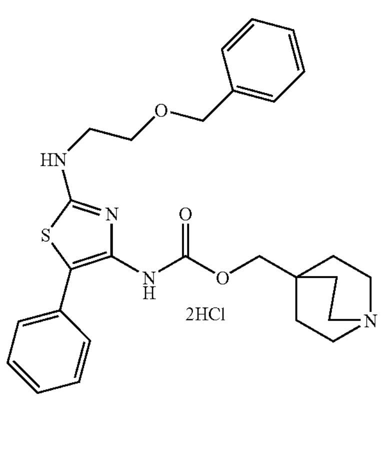 [SMILES: O=C(Nc1nc(NCCOCc2ccccc2)sc1-c1ccccc1)OCC12CCN(CC1)CC2 ; "2HCl"] |
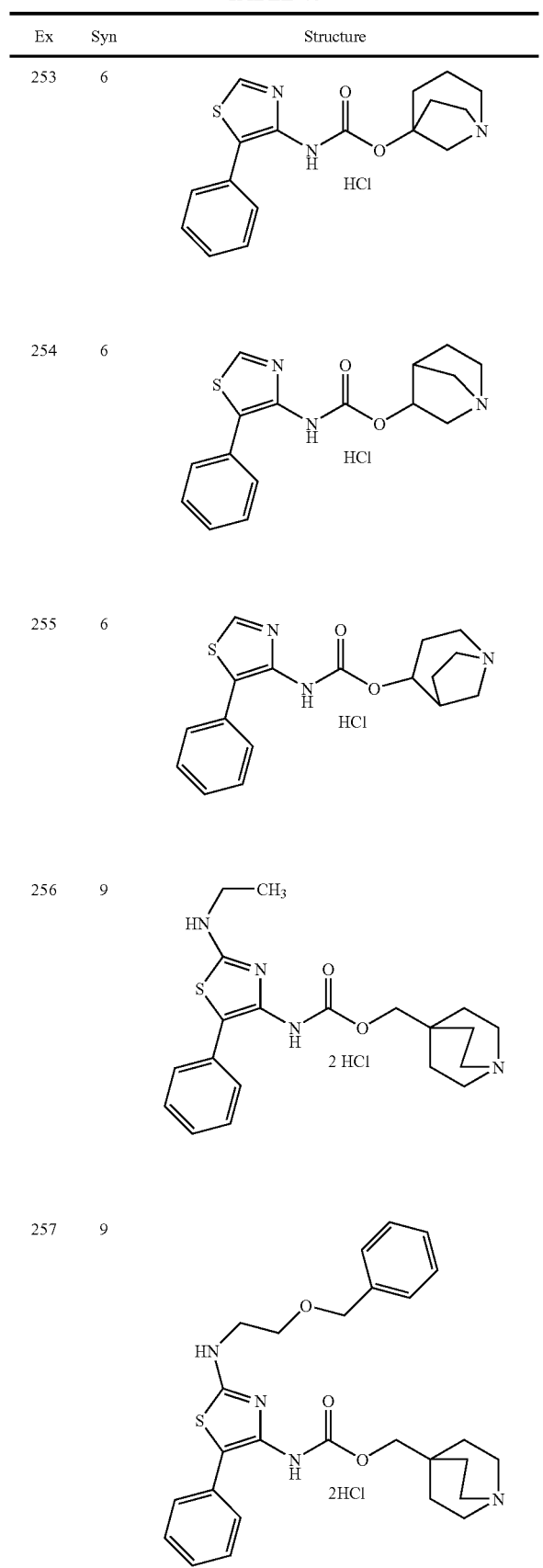
TABLE 40-continued
| Ex | Syn | Structure |
|----|-----|-----------|
| 258 | 9 | 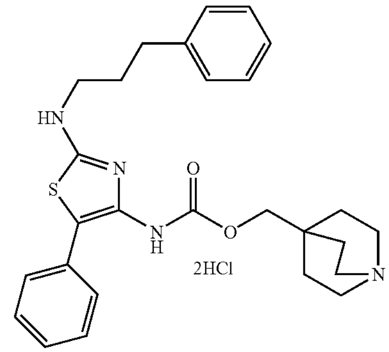 [SMILES: O=C(Nc1nc(NCCCc2ccccc2)sc1-c1ccccc1)OCC12CCN(CC1)CC2 ; "2HCl"] |
| 259 | 9 | 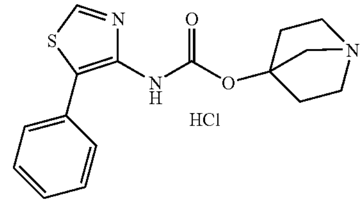 [SMILES: O=C(Nc1ncsc1-c1ccccc1)OC12CCN(CC1)C2 ; Cl ; Cl] |
| 260 | 11 | 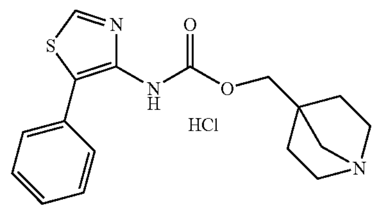 [SMILES: O=C(Nc1ncsc1-c1ccccc1)OCC12CCN(CC1)C2 ; Cl] |
| 261 | 11 | 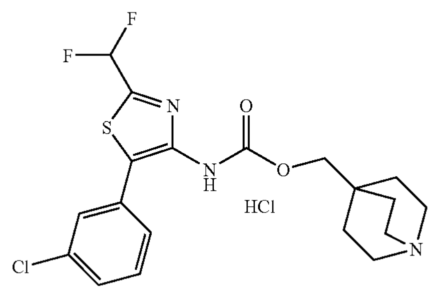 [SMILES: O=C(Nc1nc(C(F)F)sc1-c1cccc(Cl)c1)OCC12CCN(CC1)CC2 ; Cl] |
| 262 | 11 | 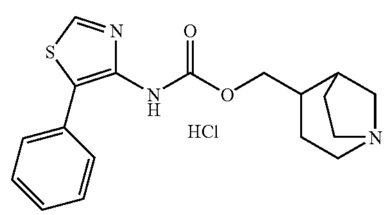 [SMILES: O=C(Nc1ncsc1-c1ccccc1)OCC1CCN2CCC1C2 ; Cl] |
| 263 | 11 | 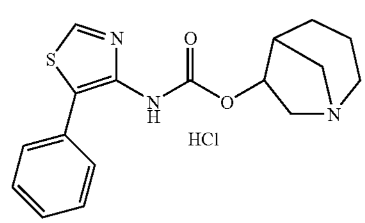 [SMILES: O=C(Nc1ncsc1-c1ccccc1)OC1CN2CCCC1C2 ; Cl] |
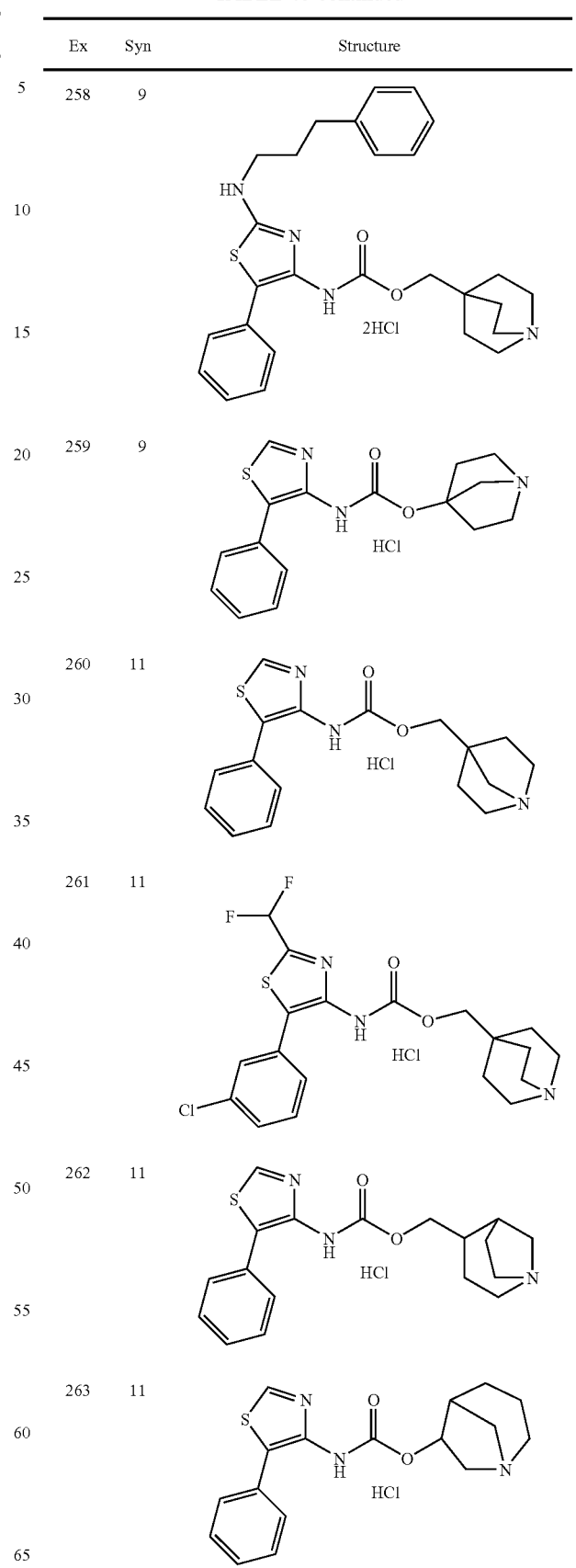

TABLE 40-continued

| Ex | Syn | Structure |
|---|---|---|
| 264 | 11 | (5-phenylthiazol-4-yl)carbamate of quinuclidin-3-ylmethyl · HCl |

TABLE 41

| Ex | Syn | Structure |
|---|---|---|
| 265 | 11 | (5-phenylthiazol-4-yl)carbamate of (1-azabicyclo[2.2.2]octan-4-yl)methyl · HCl |
| 266 | 12 | (5-phenylthiazol-4-yl)carbamate of quinuclidin-3-ylmethyl · fumarate |
| 267 | 12 | (5-phenylthiazol-4-yl)carbamate of quinuclidin-3-yl · fumarate |
| 268 | 14 | (2-trifluoromethyl-5-(3-chlorophenyl)thiazol-4-yl)carbamate of quinuclidin-3-yl |
| 269 | 14 | (5-(3-chlorophenyl)thiazol-4-yl)carbamate of 1-azabicyclo[2.2.2]octan-4-yl |

TABLE 41-continued

| Ex | Syn | Structure |
|---|---|---|
| 270 | 14 | (5-phenylthiazol-4-yl)carbamate of 1-azabicyclo[3.2.1]octan-3-ylmethyl |

TABLE 42

| Ex | data |
|---|---|
| 1 | NMR: 2.27(6H, br), 3.31(6H, br), 7.04(1H, s), 7.31-7.37(1H, m), 7.40-7.50(5H, m), 9.11(1H, br), ESI(+): 345. |
| 2 | NMR: 1.42(1H, brs), 1.53(1H, brs), 1.63(1H, brs), 1.81(1H, brs), 1.99(1H, brs), 2.32-2.39(2H, m), 2.58-2.62(2H, m), 2.67-2.81 (2H, m), 2.86-2.89(2H, m), 3.17(1H, brs), 4.61(1H, brs), 6.51(1H, s), 7.27-7.31(1H, m), 7.38-7.42(2H, m), 7.47-7.49(2H, m), 8.99(1H, brs), ESI(+): 369. |
| 3 | ESI(+): 343 |
| 4 | NMR: 1.76-1.9(5H, m), 2.4(1H, brs), 2.9(3H, s), 3.09(1H, brs), 3.3-3.4(5H, m), 2.04(2H, d, J = −1632.5 Hz), 7.11(1H, brs), 7.35(1H, t, J = 7.3 Hz), 7.44(2H, t, J = 7.6 Hz), 7.5-7.53(3H, m), 9.1(1H, brs), ESI(+): 357. |
| 5 | NMR: 1.8-2.22(5H, m), 3.13-3.24(5H, m), 3.6-3.65(1H, m), 4.87(1H, brs), 7.15(1H, d, J = 5.4 Hz), 7.28(1H, t, J = 8.9 Hz), 7.51(1H, d, J = 5.4 Hz), 7.54-7.55(2H, m), 9.22(1H, brs), 10.08(1H, brs), ESI: 347. |

TABLE 43

| Ex | data |
|---|---|
| 6 | NMR: 1.50-1.61(6H, m), 3.13-3.21(6H, m), 3.83(2H, s), 7.36-7.41(1H, m), 7.44-7.49(2H, m), 7.55-7.58(2H, m), 9.01 (1H, s), 9.48(1H, s), 10.46(1H, brs). ESI(+)344 |
| 7 | ESI(+): 369 |
| 8a | ESI(+): 362(free) <br> $[\alpha]_D^{24} = -36.0°(c = 0.1, MeOH)$ |
| 8b | ESI(+): 362(free) <br> $[\alpha]_D^{24} = +32.0°(c = 0.1, MeOH)$ |
| 9 | ESI(+): 359 |
| 10 | NMR: 1.72-2.01(5H, m), 2.87-2.92(1H, m), 3.11-3.2(4H, m), 3.95(1H, b.s), 7.15(1H, d, J = 6.5 Hz), 7.33-7.37(1H, m), 7.41-7.44(2H, m), 7.55-7.57(2H, m), 8.44(1H, s), 8.99(1H, s), 9.79(1H, brs), ESI(+): 329 |
| 11 | NMR: 1.45-1.76(7H, m), 2.93-3.35(5H, m), 4.01(2H, s), 7.37-7.4(1H, m), 7.45-7.48(2H, m), 7.55-7.57(2H, m), 9.01(1H, s), 9.5(1H, s), 10.1(1H, b.s), ESI(+): 344. |
| 12 | NMR: 1.52-1.64(6H, br), 2.10(2H, br), 2.78(2H, br), 3.03-3.07(2H, m), 3.18-3.22(2H, m), 3.70(2H, s), 6.52(2H, s), 7.35-7.38(1H, m), 7.44-7.47(2H, m), 7.55-7.57(2H, m), 9.01(1H, s), 9.46(1H, s), ESI(+): 359 |
| 13 | NMR: 1.52-1.64(6H, m), 3.16-3.57(10H, m), 3.82(2H, s), 7.17-7.57(5H, m), 7.82(1H, t, d = 6.0 Hz), 9.08(1H, s), 9.66(1H, s), ESI(+): 403 |
| 14 | NMR: 1.48-1.62(4H, m), 2.00-2.09(2H, m), 2.17-2.28(2H, m), 2.71-2.92(6H, m), 7.34-7.55(5H, m), 8.96(1H, s), 9.11(1H, s), ESI(+): 344 |
| 15a | ESI(+): 344 <br> $[\alpha]_D^{23} = -7.8°(c = 1.05, CHCl_3)$ |
| 15b | ESI(+): 344 <br> $[\alpha]_D^{23} = +5.2°(c = 0.2, CHCl_3)$ |
| 16 | NMR: 1.79-1.82(4.8H, m), 2.21(1.2H, brs), 3.02(0.6H, s), 3.09(2.4H, s), 3.21-3.25(4.8H, m), 3.39(1.2H, s), 7.12(1H, d, J = 5.3 Hz), 7.38-7.4(3H, m), 7.46-7.5(2H, m), 7.55(1H, d, J = 5.3 Hz), 10.04(1H, brs). ESI(+): 343 |
| 17 | ESI(+): 337 |
| 18 | ESI(+): 341 |
| 19 | ESI(+): 337 |

TABLE 44

| Ex | data |
|---|---|
| 20 | ESI(+): 341 |
| 21 | ESI(+): 329 |
| 22 | NMR: 1.27-2.32(14H, m), 2.75-3.30(6H, m), 3.91-3.97(1H, m), 4.33-4.51(1H, m), 6.52(2H, s), 6.97-7.27(6H, m). ESI(+): 329, $[\alpha]_D^{22}$ = +34.65°(c = 1.0, MeOH) |
| 23 | ESI(+): 329, $[\alpha]_D^{24}$ = +80.4°(c = 1.0, MeOH) |
| 24 | NMR: 1.29-2.12(14H, m), 2.77-3.55(6H, m), 3.92-3.98(1H, m), 4.50-4.60(1H, m), 7.11-7.30(6H, m), 10.39(1H, brs). ESI(+): 329, $[\alpha]_D^{24}$ = −75.3°(c = 1.0, MeOH) |
| 25 | ESI(+): 329, $[\alpha]_D^{23}$ = −44.75°(c = 1.0, MeOH) |
| 26 | NMR: 1.20-1.91(14H, m), 2.86-3.22(5H, m), 3.46-3.60(2H, m), 4.54-4.60(1H, m), 7.09-7.29(6H, m), 10.35(1H, brs). ESI(+): 329, $[\alpha]_D^{24}$ = −24.85°(c = 1.0, MeOH) |
| 27 | ESI(+): 329, $[\alpha]_D^{23}$ = +9.25°(c = 1.0, MeOH) |
| 28 | ESI(+): 329, $[\alpha]_D^{23}$ = −7.30°(c = 1.0, MeOH) |
| 29 | NMR: 1.19-1.50(4H, m), 1.66-1.88(10H, m), 2.43-2.50(1H, m), 3.00-3.07(6H, m), 3.43-3.53(1H, m), 6.50(2H, s), 6.80-6.83(1H, m), 7.11-7.29(5H, m). ESI(+): 329, $[\alpha]_D^{24}$ = +11.5°(c = 1.0, MeOH) |
| 30 | ESI(+): 329, $[\alpha]_D^{24}$ = −11.7°(c = 1.0, MeOH) |
| 31 | NMR: 1.20-2.11(14H, m), 2.45-2.67(2H, m), 3.02-3.22(5H, m), 3.50-3.59(1H, m), 3.69-3.95(2H, m), 6.92-7.28(6H, m), 10.09(1H, brs). ESI(+): 343 |
| 32 | NMR: 2.25(6H, brs), 2.92(3H, s), 3.59-3.63(6H, m), 7.44-7.51(3H, m), 7.57(1H, s), 9.05(1H, s), 9.68(1H, brs), ESI(+): 378 |
| 33 | NMR: 1.75-1.99(5H, m), 2.39(1H, brs), 3.04(1H, brs), 3.29-3.42(4H, m), 4.07(2H, brs), 4.41-4.45(2H, m), 7.09(1H, brs), 7.34(1H, t, J = 7.3 Hz), 7.43(2H, t, J = 7.6 Hz), 7.49-7.52(8H, m), 9.1(1H, brs). ESI(+): 433 |
| 34 | ESI(+): 362 |
| 35 | NMR: 2.32(6H, brs), 2.93(3H, s), 3.61(6H, brs), 7.05(1H, brs), 7.34(1H, t, J = 7.3 Hz), 7.44(2H, t, J = 7.6 Hz), 7.49-7.51 (2H, m), 9.14(1H, brs). ESI(+): 343 |
| 36 | ESI(+): 413 |
| 37 | NMR: 1.79-1.94(5H, m), 2.44(1H, brs), 3(2H, brs), 3.15(1H, brs), 3.37-3.6(6H, m), 4.08-4.14(2H, m), 7.13(1H, brs), 7.26-7.38(6H, m), 7.44(2H, t, J = 7.7 Hz), 7.51-7.54(3H, m), 9.11(1H, brs). ESI(+): 447 |
| 38 | ESI(+): 376 |

TABLE 45

| Ex | data |
|---|---|
| 39 | NMR: 1.78-1.93(5H, m), 2.42(1H, brs), 3.23(1H, brs), 3.54-3.63(7H, m), 4.09(2H, brs), 4.42(2H, brs), 6.98-7.02(3H, m), 7.1(1H, brs), 7.31-7.36(3H, m), 7.43(2H, t, J = 7.6 Hz), 7.51(3H, t, J = 7.5 Hz), 9.10(1H, brs). ESI(+): 463 |
| 40 | ESI(+): 394 |
| 41 | NMR: 1.77-2.13(7H, m), 2.42(1H, brs), 3.1(1H, brs), 3.3-3.54(6H, m), 4-4.13(4H, m), 6.93-9.98(3H, m), 7.12(1H, brs), 7.29-7.36(3H, m), 7.44(2H, t, J = 7.7 Hz), 7.5-7.54(3H, m), 9.10(1H, brs). ESI(+): 477 |
| 42 | ESI(+): 412 |
| 43 | NMR: 1.73-1.97(7H, m), 2.39(1H, brs), 2.59(2H, t, J = 7.7 Hz), 3.04-3.14(3H, m), 3.29-3.38(5H, m), 4.09(2H, brs), 7.1(1H, brs), 7.21-7.26(3H, m), 7.3-7.35(3H, m), 7.42(2H, t, J = 7.6 Hz), 7.51(3H, t, J = 7.3 Hz), 9.07(1H, brs). ESI(+): 461 |
| 44 | NMR: 2.15-2.30(6H, m), 2.92(3H, s), 3.56-3.63(6H, m), 7.36-7.41(1H, m), 7.44-7.48(2H, m), 7.51-7.54(2H, m), 9.00(1H, s), 9.53(1H, brs). ESI: 344 |
| 45 | NMR: 0.89(3H, t, J = 7.2 Hz), 1.21-1.36(4H, m), 1.6-1.89(7H, m), 2.39(1H, brs), 3.09(3H, brs), 3.27-3.41(5H, m), 4.09(2H, brs), 7.11(1H, brs), 7.34(1H, t, J = 7.3 Hz), 7.43(2H, t, J = 7.6 Hz), 7.5-7.53(3H, m), 9.08(1H, brs). ESI(+): 413 |
| 46 | NMR: 2.19-2.32(6H, m), 3.62-3.77(8H, m), 4.37-4.41(2H, m), 6.97-7.02(3H, m)7.31-7.41(3H, m), 7.43-7.48(2H, m), 7.51-7.55(2H, m), 9.00(1H, s), 9.54(1H, brs). ESI(+): 450 |
| 47 | NMR: 1.60-1.69(6H, m), 2.92(3H, s), 3.37-3.44(6H, m), 3.87(2H, s), 7.37-7.41(1H, m), 7.44-7.49(2H, m), 7.54-7.58(2H, m), 9.01(1H, s), 9.47(1H, brs). ESI(+): 358 |
| 48 | NMR: 2.08-2.33(8H, m), 3.31-3.36(2H, m), 3.57-3.66(6H, m), 4.02(2H, t, J = 6.0 Hz), 6.92-6.97(3H, m)7.27-7.33(2H, m), 7.36-7.55(5H, m), 9.01(1H, s), 9.55(1H, brs). ESI(+): 464 |

TABLE 45-continued

| Ex | data |
|---|---|
| 49 | NMR: 1.71-1.91(5H, m), 2.39(1H, m), 2.89(3H, s), 3.03(1H, m), 3.34-3.47(5H, m), 3.98-4.10(2H, m), 7.37-7.56(5H, m), 9.00(1H, s), 9.48(1H, br). ESI(+): 358 |
| 50 | NMR: 2.20-2.32(6H, m), 2.96-3.02(2H, m), 3.34-3.45(2H, m), 3.62-3.70(6H, m), 7.25-7.41(6H, m)7.44-7.55(4H, m), 9.01(1H, s), 9.56(1H, brs). ESI(+): 434 |
| 51 | NMR1.81-1.93(4H, m), 2.16(1H, brs), 2.93(3H, s), 3.26-3.42(5H, m), 3.77-3.82(1H, m), 4.88-4.9(1H, m), 7.39(1H, t, J = 7.4 Hz), 7.47(2H, t, J = 7.6 Hz), 7.57(2H, d, J = 7.6 Hz), 9.02(1H, s), 9.68(1H, brs). ESI(+): 344 |
| 52 | ESI(+): 448 |
| 53 | NMR: 1.83-1.95(4H, m), 2.19(1H, brs), 2.95(3H, s), 3.27-3.44(5H, m), 3.79-3.85(1H, m), 4.9-4.93(1H, m), 7.45-7.51(3H, m), 7.62(1H, s), 9.07(1H, s), 9.8(1H, brs). ESI(+): 378 |

TABLE 46

| Ex | data |
|---|---|
| 54 | ESI(+): 420 |
| 55 | ESI(+): 378 |
| 56 | ESI(+): 434 |
| 57 | ESI(+): 380 |
| 58 | ESI(+): 450 |
| 59 | ESI(+): 380 |
| 60 | ESI(+): 464 |
| 61 | NMR: 2.19(6H, brs), 2.91(3H, s), 3.56-3.6(6H, m), 7.2(1H, dt, J = 2.5, 8.3 Hz), 7.37-7.43(1H, m), 7.53(1H, q, J = 8.3 Hz), 9.11(1H, br), 9.73(1H, brs), ESI(+): 380 |
| 62 | ESI(+): 384 |
| 63 | NMR: 2.20-2.31(6H, m), 2.93(3H, s), 3.58-3.64(6H, m), 7.31(1H, t, J = 54 Hz), 7.52-7.53(3H, m), 7.63-7.65(1H, m), 9.92(1H, s), ESI(+): 428 |
| 64 | NMR: 2.23-2.33(6H, m), 3.62-3.67(2H, m), 3.71-3.78(6H, m), 4.37-4.42(2H, m), 6.97-7.02(3H, m), 7.23-7.54(6H, m), 7.63-7.65(1H, m), 9.93(1H, s), ESI(+): 534 |
| 65 | NMR: 1.87-2.47(8H, m), 3.06(3H, m), 3.44-3.61(6H, m), 7.36-7.55(5H, m), 8.99(1H, s), 9.39(1H, s), ESI(+): 358 |
| 66 | NMR: 2.28(6H, br), 3.64(2H, br), 3.72-3.76(6H, m), 4.39(2H, br), 6.98-7.02(3H, m), 7.32-7.35(2H, m), 7.44-7.49(4H, m), 7.56(1H, s), 9.05(1H, s), ESI(+): 484,486 |
| 67 | NMR: 1.90-2.23(6H, m), 2.39-2.50(2H, m), 3.06(3H, m), 3.46-3.64(6H, m), 7.44-7.51(3H, m), 7.57-7.59(1H, m), 9.04(1H, s), 9.55(1H, s), ESI(+): 392 |
| 68 | NMR: 1.80-1.88(3H, m), 2.03(1H, brs), 2.24(1H, brs), 3.15(5H, brs), 3.62(1H, brs), 4.89(1H, brs), 7.17-7.21(2H, m), 7.35-7.39(2H, m), 7.46-7.52(1H, m), 7.57(1H, d, J = 5.4 Hz), 9.37(1H, brs), 10.2(1H, brs). ESI(+): 347 |
| 69 | NMR: 1.81(3H, brs), 2.08(1H, brs), 2.28(1H, brs), 3.14(5H, brs), 3.64(1H, brs), 4.91(1H, brs), 7.08(1H, d, J = 5.4 Hz), 7.11(1H, dd, J = 3.6, 5.1 Hz), 7.3(1H, dd, J = 1.1, 3.6 Hz), 7.46(1H, d, J = 5.4 Hz), 7.57(1H, dd, J = 1.1, 5.1 Hz), 9.25(1H, brs), 10.2(1H, brs). ESI(+): 335 |
| 70 | NMR: 1.72-1.99(4H, m), 2.2(1H, brs), 3.07-3.24(5H, m), 3.6-3.65(1H, m), 4.85-4.87(1H, m), 7.23-7.33(3H, m), 7.41-7.49(2H, m), 7.63(1H, d, J = 5.4 Hz), 9.29(1H, brs), 9.95(1H, brs). ESI(+)347 |
| 71 | NMR: 1.47(1H, brs), 1.62(1H, brs), 1.71(1H, brs), 1.83(1H, brs), 2.02(1H, brs), 2.82-2.89(5H, m), 3.29(1H, brs), 3.78(3H, s), 4.72(1H, brs), 6.52(2H, s), 7.01(1H, t, J = 7.5 Hz), 7.12(1H, d, J = 8.2 Hz), 7.2(1H, brs), 7.32-7.38(2H, m), 7.5(1H, d, J = 5.4 Hz), 8.63(1H, brs). ESI(+): 359 |

TABLE 47

| Ex | data |
|---|---|
| 72 | NMR: 1.81(3H, brs), 2.09(1H, brs), 2.29(1H, brs), 2.46(3H, d, J = .3 Hz), 3.13(5H, brs), 3.64(1H, brs), 4.91(1H, brs), 6.8(1H, dd, J = 1.1, 3.6 Hz), 7.04(1H, d, J = 5.3 Hz), 7.08(1H, d, J = 3.6 Hz), 7.41(1H, d, J = 5.3 Hz), 9.17(1H, brs), 10.19(1H, brs). ESI(+): 349 |
| 73 | NMR: 1.24-1.57(3H, m), 1.74(1H, br), 1.90(1H, br), 2.56-2.70(5H, m), 3.07(1H, br), 4.60(1H, br), 7.10(1H, br), 7.29-7.32(2H, m), 7.39-7.43(2H, m), 7.48-7.50(2H, m), 9.42(1H, br). ESI(+): 329 |

TABLE 47-continued

| Ex | data |
|---|---|
| 74 | NMR: 1.41(1H, brs), 1.55(1H, brs), 1.65(1H, brs), 1.83(1H, brs), 1.97(1H, brs), 2.72-2.82(5H, m), 3.19(1H, brs), 3.7(3H, s), 4.64(1H, brs), 6.5(1H, s), 6.98-7.02(2H, m), 7.07(1H, brs), 7.41(1H, d, J = 5.4 Hz), 7.45(2H, d, J = 8.7 Hz), 8.97(1H, brs). ESI(+): 359 |
| 75 | ESI(+): 337 |
| 76 | NMR: 1.45(1H, brs), 1.59(1H, brs), 1.68(1H, brs), 1.85(1H, brs), 1.99(1H, brs), 2.77-2.86(5H, m), 3.26(1H, brs), 3.78(3H, s), 4.68(1H, brs), 6.53(2H, s), 6.91-6.93(1H, m), 7.07-7.09(3H, m), 7.34(1H, t, J = 8 Hz), 7.49(1H, d, J = 5.2 Hz), 9.11(1H, brs). ESI(+): 359 |
| 77 | ESI(+): 337 |
| 78 | NMR: 1.8-1.88(3H, m), 2.04(1H, brs), 2.25(1H, brs), 2.33(3H, s), 3.14(5H, brs), 3.62(1H, brs), 4.88(1H, brs), 7.13(1H, d, J = 5.4 Hz), 7.25(2H, d, J = 7.8 Hz), 7.42(2H, d, J = 7.8 Hz), 7.47(1H, d, J = 5.4 Hz), 9.19(1H, brs), 10.04(1H, brs). ESI(+): 343 |
| 79 | ESI(+): 341 |
| 80 | NMR: 1.78-1.87(3H, m), 2.02(1H, brs), 2.24(1H, brs), 2.34(3H, s), 3.13(5H, brs), 3.61(1H, brs), 4.88(1H, brs), 7.13-7.17(2H, m), 7.3-7.34(3H, m), 7.5(1H, d, J = 5.4 Hz), 9.21(1H, brs), 10.2(1H, brs). ESI(+): 343 |
| 81 | ESI(+): 341 |
| 82 | NMR: 1.69-1.91 (4H, m), 2.16(4H, brs), 3.05-3.26(5H, m), 3.59-3.65(1H, m), 4.84-4.86(1H, m), 7.21-7.28(3H, m), 7.31-7.32(2H, m), 7.54(1H, d, J = 5.4 Hz), 8.98(1H, brs), 9.79(1H, brs). ESI(+): 343 |
| 83 | ESI(+): 341 |
| 84 | NMR: 1.81-1.87(4H, m), 2.24(1H, brs), 3.14(5H, brs), 3.64(1H, brs), 4.91(1H, brs), 7.4(1H, t, J = 7.6 Hz), 7.5(2H, t, J = 7.6 Hz), 7.67(2H, d, J = 7.6 Hz), 8.4(1H, s), 9.62(1H, brs), 9.87(1H, brs), ESI(+): 314 |
| 85 | ESI(+): 439, less polar(10% MeOH in CHCl₃, Rf = 0.25) |
| 86 | NMR: 1.64(6H, brs), 3.2(6H, brs), 3.91(2H, brs), 7.39(1H, t, J = 7.6 Hz), 7.5(2H, t, J = 7.6 Hz), 7.66(2H, d, J = 7.6 Hz), 8.39(1H, s), 9.46(1H, brs), 10.3(1H, brs). ESI(+): 328 |
| 87 | ESI(+): 439, more polar(10% MeOH in CHCl₃, Rf = 0.20) |

TABLE 48

| Ex | data |
|---|---|
| 88 | NMR: 1.64-1.89(5H, m), 2.33(1H, brs), 2.81(1H, brs), 3.17(5H, brs), 4.07-4.17(2H, m), 7.39(1H, t, J = 7.5 Hz), 7.5(2H, t, J = 7.5 Hz), 7.65(2H, d, J = 7.5 Hz), 8.39(1H, s), 9.46(1H, brs), 10.03(1H, brs), ESI(+): 328 |
| 89 | NMR: 1.48-2.27(6H, m), 2.61-2.67(2H, m), 3.01-3.32(4H, m), 3.74(1H, brs), 4.89(1H, brs), 7.16-7.25(4H, m), 7.29-7.37(4H, m), 7.45(2H, t, J = 7.6 Hz), 7.51-7.55(3H, m), 9.22(1H, brs), 10.00(1H, brs). ESI(+): 433 less polar(10% MeOH in CHCl₃, Rf = 0.25) |
| 90 | NMR: 1.60-2.20(7H, m), 2.63(3H, s), 3.32-3.38(6H, m), 4.88-4.92(2H, m), 7.20-7.54(5H, m), 9.48(1H, s), 10.49(1H, brs). ESI(+): 370 |
| 91 | NMR: 1.46-2.32(6H, m), 2.67(2H, m), 3.00-3.65(5H, m), 4.83-4.89(1H, m), 7.14-7.54(12H, m), 9.3(1H, brs), 10.27(1H, brs). ESI(+): 433 more polar(10% MeOH in CHCl₃, Rf = 0.20) |
| 92 | NMR: 2.14(6H, brs), 2.62(3H, s), 3.26-3.42(6H, m), 7.26-7.50(5H, m), 9.41(1H, s), 10.46(1H, brs). ESI(+): 344 |
| 93 | NMR: 1.53-1.86(5H, m), 2.14-2.22(1H, m), 2.65-2.72(1H, m), 3.01-3.26(5H, m), 3.97-4.09(4H, m), 6.54(2H, m), 7.35-7.40(1H, m), 7.43-7.47(2H, m), 7.53-7.56(2H, m), 9.00(1H, s), 9.44(1H, brs). ESI(+): 344 |
| 94 | NMR: 1.60-1.94(4H, m), 2.14(1H, brs), 2.63(3H, s), 2.82-3.26(4H, m), 3.48-3.64(2H, m), 4.80-4.86(1H, m), 7.32-7.54(5H, m), 9.58(1H, s), 10.44(1H, brs). ESI(+): 344 |
| 95 | NMR: 1.76(6H, brs), 2.78-2.82(6H, m), 7.36(1H, t, J = 7.3 Hz), 7.44(2H, t, J = 7.7 Hz), 7.52-7.54(2H, m), 8.96(1H, s), 9.16(1H, brs). ESI(+): 330 |
| 96 | NMR: 1.8(3H, brs), 2.05(1H, brs), 2.29(1H, brs), 3.16-3.23(5H, m), 3.64(1H, brs), 4.97(1H, brs), 7.37(1H, t, J = 7.4 Hz), 7.47(2H, t, J = 7.7 Hz), 7.78(2H, d, J = 7.4 Hz), 8.92(1H, s), 10.92(1H, brs), 10.4(1H, brs). ESI(+): 330 |
| 97 | NMR: 1.18-1.40(6H, m), 2.64-2.76(6H, m), 3.66-3.72(2H, m), 7.08(1H, brs), 7.31-7.36(1H, m), 7.40-7.45(2H, m), 7.48-7.54(3H, m), 8.96(1H, brs). ESI(+): 343 |

TABLE 48-continued

| Ex | data |
|---|---|
| 98 | NMR: 1.69-2.04(5H, m), 2.37(1H, brs), 2.86(1H, brs), 3.19-3.34(5H, m), 4.17(2H, brs), 7.36(1H, t, J = 7.6 Hz), 7.46(2H, t, J = 7.6 Hz), 7.77(2H, d, J = 7.6 Hz), 8.92(1H, brs), 9.96(1H, brs), 10.2(1H, brs). ESI(+): 344 |
| 99 | NMR: 1.80-2.26(6H, m), 3.28-3.40(6H, m), 7.31-7.44(5H, m), 7.52-7.53(1H, m), 8.85(1H, s), 10.52(1H, brs). ESI(+): 329 |
| 100 | ESI(+): 344 |
| 101 | NMR: 1.26(6H, brs), 2.69(6H, brs), 3.69(2H, brs), 7.15(1H, s), 7.36(1H, t, J = 7.2 Hz), 7.44(2H, t, J = 7.6 Hz), 7.48-7.5(2H, m), 9.14(1H, brs), ESI(+): 377 |
| 102 | NMR: 1.48(6H, br), 2.61(3H, s), 2.93(6H, br), 3.83(2H, brs), 6.42(1H, s), 7.34(1H, t, J = 7 Hz), 7.43(2H, t, J = 7 Hz), 7.75(2H, d, J = 7 Hz). ESI(+): 358 |

TABLE 49

| Ex | data |
|---|---|
| 103 | NMR: 1.27(1H, brs), 1.41(1H, brs), 1.51-1.65(3H, m), 1.85(1H, brs), 2.2-2.25(1H, m), 2.61-2.66(3H, m), 2.82(1H, brs), 3.97-4.04(2H, m), 7.15(1H, s), 7.34-7.38(1H, m), 7.43(2H, t, J = 7.6 Hz), 7.47-7.49(2H, m), 9.16(1H, brs). ESI(+): 377 |
| 104 | NMR: 1.5-1.9(4H, m), 2.61(3H, s), 3.0(4H, br), 4.11(2H, m), 6.47(1H, s), 7.33(1H, t, J = 7 Hz), 7.43(2H, t, J = 7 Hz), 7.75(2H, d, J = 7 Hz). ESI(+): 358 |
| 105 | NMR: 1.85(6H, brs), 2.84(6H, brs), 7.06(1H, d, J = 5.6 Hz), 7.27-7.32(2H, m), 7.41(1H, t, J = 7.6 Hz), 7.46-7.47(2H, m), 9.17(1H, brs). ESI(+)329 |
| 106 | NMR: 1.9(6H, br), 2.60(3H, s), 2.9(6H, br), 6.5(1H, s), 7.32(1H, t, J = 7 Hz), 7.42(2H, t, J = 7 Hz), 7.73(2H, brd, J = 7 Hz). ESI(+)344 |
| 107 | NMR: 1.3(6H, brs), 2.7(6H, brs), 3.72(2H, brs), 7.1(1H, brs), 7.31(2H, t, J = 7.2 Hz), 7.41(2H, t, J = 7.6 Hz), 7.48-7.5(2H, m), 9.38(1H, brs). ESI(+): 343 |
| 108 | NMR: 1.4-2.1(6H, m), 2.6(3H, s), 2.78-2.91(3H, m), 4.76(1H, br), 6.55(2H, s), 7.33(1H, t, J = 7.5 Hz), 7.43(2H, t, J = 7.5 Hz), 7.75(2H, d, J = 7.5 Hz). ESI(+): 344 |
| 109 | NMR: 1.27-1.89(6H, m), 2.23(1H, brs), 2.66(4H, brs), 2.84(1H, brs), 4.02(2H, brs), 7.09(1H, d, J = 5.6 Hz), 7.29-7.32(2H, m), 7.38-7.43(1H, m), 7.47-7.48(2H, m), 9.38(1H, brs), ESI(+): 343 |
| 110 | NMR: 1.69-2.14(7H, m), 3.30-3.46(6H, m), 4.76-4.48(0.4H, m), 4.89-4.92(0.6H, m), 7.35-7.40(1H, m), 7.42-7.48(2H, m), 7.54-7.58(2H, m), 9.02(1H, brs), 9.56(0.6H, brs), 9.62(0.4H, brs), 10.46(0.6H, brs), 10.69(0.4H, brs). ESI(+): 356 |
| 111 | NMR: 1.24-1.88(5H, m), 2.55-2.67(5H, m), 3.05(1H, brs), 4.57(1H, brs), 7.16(1H, s), 7.36(1H, t, J = 7.2 Hz), 7.44(2H, t, J = 7.6 Hz), 7.47-7.51(2H, m), 9.17(1H, brs). ESI(+)363 |
| 112 | NMR: 1.58-1.90(5H, m), 2.20-2.29(1H, m), 2.73-2.80(1H, m), 3.08-3.31(5H, m), 3.99-4.13(2H, m), 7.35-7.55(5H, m), 9.65(1H, brs), 10.3(1H, brs). ESI(+): 378 |
| 113 | NMR: 1.15-1.36(6H, m), 2.64-2.75(6H, m), 3.65(2H, brs), 7.31-7.53(7H, m), 8.72(1H, brs). ESI(+): 343 |
| 114 | NMR: 1.53-1.62(6H, m), 3.14-3.23(6H, m), 3.85(2H, s), 7.40-7.56(5H, m), 9.64(1H, brs), 10.20(1H, brs). ESI(+): 378 |
| 115 | NMR: 2.21(6H, brs), 2.41(3H, d, J = 1.1 Hz), 3.37(6H, brs), 6.77(1H, brs), 7.28-7.32(1H, m), 7.4-7.46(4H, m), 9.04(1H, brs), 9.98(1H, brs). ESI(+): 343 |
| 116 | NMR: 1.62-1.96(4H, m), 2.11-2.20(1H, m), 2.90-3.26(5H, m), 3.54-3.63(1H, m), 4.82-4.88(1H, m), 7.37-7.58(5H, m), 9.82(1H, brs), 10.33(1H, brs). ESI(+)364 |

TABLE 50

| Ex | data |
|---|---|
| 117 | NMR: 1.19-2.07(5H, m), 1.93(3H, s), 2.34(3H, m), 2.74-2.96(5H, m), 3.3-3.35(1H, m), 4.55(0.3H, brs), 4.72(0.7H, brs), 6.58(2H, s), 7.27-7.31(1H, m), 7.38-7.47(4H, m), 8.67(0.3H, brs), 8.93(0.7H, brs). ESI(+): 357 |
| 118 | NMR: 2.08-2.19(6H, m), 3.30-3.40(6H, m), 7.39-7.53(5H, m), 9.66(1H, brs), 10.37(1H, brs). ESI(+): 364 |

TABLE 50-continued

| Ex | data |
|---|---|
| 119 | NMR: 1.17-1.92(5H, m), 2.43-2.74(5H, m), 2.94-3.09(1H, m), 4.42-4.60(1H, m), 7.30-7.53(7H, m), 8.75(1H, brs). ESI(+): 329 |
| 120 | NMR: 1.22-1.88(5H, m), 2.19-2.26(1H, m), 2.62-2.86(5H, m), 3.25-3.48(1H, m), 3.91-4.02(5H, m), 7.29-7.47(5H, m), 9.26(1H, brs). ESI(+): 374 |
| 121 | NMR: 1.60-1.96(3H, m), 2.04-2.15(1H, m), 2.24-2.32(1H, m), 2.91-3.39(5H, m), 3.60-3.68(1H, m), 4.88-4.95(1H, m), 7.41-7.56(5H, m), 7.64-7.77(3H, m), 7.98-8.01(1H, m), 9.50(1H, brs), 10.25(1H, brs). ESI(+): 379 |
| 122 | NMR: 1.54-1.92(5H, m), 2.14-2.39(1H, m), 2.62(3H, s), 2.70-2.80(1H, m), 3.04-3.30(5H, m), 3.94-4.12(2H, m), 7.32-7.52(5H, m), 9.40(1H, s), 10.32(1H, brs). ESI(+): 358 |
| 123 | NMR: 1.79-1.90(3H, m), 2.00(1H, br), 2.23(1H, br), 3.12-3.20(5H, m), 3.60(1H, br), 4.87(1H, br), 7.15(1H, d, J = 5.2 Hz), 7.32-7.36(1H, m), 7.42-7.46(2H, m), 7.51-7.55(3H, m), 9.26(1H, br), 10.41(1H, br). ESI(+): 329 |
| 124 | NMR: 1.46-1.70(6H, m), 2.63(3H, s), 3.12-3.25(6H, m), 3.83(2H, brs), 7.32-7.54(5H, m), 9.40(1H, s), 10.25(1H, brs). ESI(+): 358 |
| 125 | NMR: 1.79-1.90(3H, m), 2.00(1H, br), 2.23(1H, br), 3.12-3.20(5H, m), 3.60(1H, br), 4.87(1H, br), 7.15(1H, d, J = 5.2 Hz), 7.32-7.36(1H, m), 7.42-7.46(2H, m), 7.51-7.55(3H, m), 9.26(1H, br), 10.55(1H, br). ESI(+)329 $[\alpha]^D_{26}$ = −9.2°(C = 1.0, MeOH). |
| 126 | NMR(CDCl$_3$)δ: 1.64-2.14(8H, m), 3.18-3.52(6H, m), 4.12-4.28(2H, m), 6.55(2H, s), 7.24-7.54(5H, m), 8.64(1H, s), 9.08(1H, brs). ESI (+): 369 |
| 127 | NMR: 1.79-1.90(3H, m), 2.00(1H, br), 2.23(1H, br), 3.12-3.20(5H, m), 3.60(1H, br), 4.87(1H, br), 7.15(1H, d, J = 5.2 Hz), 7.32-7.36(1H, m), 7.42-7.46(2H, m), 7.51-7.55(3H, m), 9.25(1H, br), 10.23(1H, br). ESI(+): 329 $[\alpha]^D_{26}$ = +9.4°(C = 1.0, MeOH) |
| 128 | NMR: 1.24(3H, t, J = 7.6 Hz), 1.43(1H, brs), 1.57(1H, brs), 1.66(1H, brs), 1.83(1H, brs), 1.99(1H, brs), 2.67-2.85(4H, m), 2.74-2.8(2H, m), 4.65(1H, brs), 6.52(1H, s), 6.85(1H, brs), 7.27-7.32(1H, m), 7.39-7.42(2H, m), 7.48-7.49(2H, m), 9.03(1H, brs). ESI(+): 357 |
| 129 | NMR: 2.26(6H, br), 3.36(6H, br), 7.07(1H, br), 7.31-7.34(2H, m), 7.41-7.51(4H, m), 9.12(1H, br), 10.42(1H, br). ESI(+): 329 |

TABLE 51

| Ex | data |
|---|---|
| 130 | NMR: 1.70-2.10(7H, m), 2.42(1.5H, s), 2.43(1.5H, s), 3.1-3.3(6H, m), 4.81(0.5H, brs), 4.86(0.5H, brs), 6.50(2H, s), 6.83(0.5H, brs), 6.90(0.5H, brs), 7.30(1H, t, J = 7.5 Hz), 7.40(2H, dt, J = 2.7, 7.5 Hz), 7.46-7.49(2H, m). ESI(+): 369. |
| 131 | NMR: 1.49(1H, brs), 1.6(1H, brs), 1.69(1H, brs), 1.87(1H, brs), 2.04(1H, brs), 2.42(3H, d, J = 2 Hz), 2.82-2.91(5H, m), 3.29(1H, brs), 4.69(1H, brs), 6.53(2H, s), 6.83(1H, brs), 7.27-7.32(1H, m), 7.39-7.43(2H, m), 7.48(2H, d, J = 7.3 Hz), 9.08(1H, brs). ESI(+): 343 |
| 132 | NMR: 1.28(6H, d, J = 6.7 Hz), 1.42(1H, brs), 1.55(1H, brs), 1.66(1H, brs), 1.82(1H, brs), 1.99(1H, brs), 2.64-2.84(4H, m), 3.1(1H, q, J = 6.8 Hz), 3.21(1H, brs), 4.65(1H, brs), 6.52(1H, s), 6.86(1H, brs), 7.28-7.31 (1H, m), 7.38-7.42(2H, m), 7.48-7.5(2H, m), 9.01(1H, brs). ESI(+): 371 |
| 133 | NMR: 1.47-1.55(2H, m), 1.66(1H, brs), 1.84(1H, brs), 1.91(3H, m), 1.93(1H, brs), 1.17(3H, d, J = −932.3 Hz), 2.62-2.85(5H, m), 3.18-3.24(1H, m), 4.65(1H, brs), 6.51(1H, s), 7.29(1H, t, J = 7.2 Hz), 7.4(2H, t, J = 6.7 Hz), 7.46(2H, d, J = 7.2 Hz), 8.88(1H, s). ESI(+): 357 |
| 134 | NMR: 2.2(6H, brs), 3.37(6H, brs), 7.13(1H, s), 7.35-7.38(1H, m), 7.42-7.49(4H, m), 9.91(1H, brs). ESI(+): 363 |
| 135 | NMR: 1.42-1.49(1H, m), 1.57-1.77(3H, m), 1.83(1H, q, J = 3 Hz), 2.75-2.87(4H, m), 3.27(1H, dd, J = 9.6, 13.2 Hz), 3.74(1H, brs), 6.45(1H, s), 6.94(1H, d, J = 6.9 Hz), 7.34-7.39(1H, m), 7.44(1H, d, J = 5.4 Hz), 7.47(2H, s), 7.48(2H, s), 7.53(1H, d, J = 5.4 Hz), 8.02(1H, s). ESI(+): 328 |
| 136 | NMR: 1.59-2.02(5H, m), 2.21-2.38(1H, m), 2.76-2.86(1H, m), 3.06-3.37(5H, m), 4.00-4.15(2H, m), 7.11(1H, m), 7.32-7.36(1H, m), 7.41-7.46(2H, m), 7.50-7.54(3H, m), 9.12(1H, brs), 10.37(1H, brs). ESI(+): 343 |

TABLE 51-continued

| Ex | data |
|---|---|
| 137 | NMR: 1.74(1H, brs), 1.85-1.91 (3H, m), 2.01-2.03(1H, m), 2.91(1H, dd, J = 4.4, 12.9 Hz), 3.16-3.2(4H, m), 3.59(1H, dd, J = 9.7, 13.3 Hz), 3.97(1H, brs), 7.25(1H, d, J = 6.2 Hz), 7.37-7.41(1H, m), 7.48(4H, d, J = 4.3 Hz), 7.51(1H, s), 8.2(1H, s), 9.8(1H, brs). ESI(+): 362 |
| 138 | NMR: 1.42-1.72(4H, m), 1.96(1H, br), 2.63(1H, br), 2.73-2.93(4H, m), 3.24-3.30(1H, m), 4.67-4.69(1H, m), 6.53(2H, s), 7.35-7.39(1H, m), 7.44-7.47(2H, m), 7.54-7.57(2H, m), 9.00(1H, s), 9.51(1H, s). ESI(+): 330 |
| 139 | NMR: 1.86-1.90(6H, m), 3.01-3.05(6H, m), 6.44(1H, s), 6.54(1H, br), 7.33-7.37(1H, m), 7.42(1H, d, J = 5.4 Hz), 7.43-7.49(5H, m), 7.51(1H, d, J = 5.4 Hz). ESI(+): 328 |
| 140 | NMR: 1.72-1.91(4H, m), 2.14(1H, brs), 2.93-3.21(5H, m), 3.56-3.61(1H, m), 4.83-4.85(1H, m), 7.39(1H, t, J = 7.3 Hz), 7.46(2H, t, J = 7.6 Hz), 7.56(2H, d, J = 7.4 Hz), 9.02(1H, brs), 9.65(1H, brs), 10.21(1H, brs). ESI(+): 330 |

TABLE 52

| Ex | data |
|---|---|
| 141 | NMR: 1.52-1.59(6H, m), 2.99(2H, d, J = 6.4 Hz), 3.12-3.18(6H, m), 6.70(1H, t, J = 6.4 Hz), 7.33-7.38(1H, m), 7.43-7.51(6H, m), 8.06(1H, s). ESI(+): 342 |
| 142 | NMR: 1.62(1.2H, brs), 1.91(3H, s), 1.95(4.8H, brs), 2.32(3H, brs), 2.84(1.2H, brs), 2.97(4.8H, brs), 6.51(1H, s), 7.27-7.31(1H, m), 7.39(2H, t, J = 7.6 Hz), 7.44-7.46(2H, m), 8.34(0.2H, brs), 8.66(0.8H, brs). ESI(+): 357 |
| 143 | NMR: 1.67-1.71(6H, m), 2.76-2.8(6H, m), 6.34(1H, s), 7.36-7.5(5H, m), 7.56(1H, s), 7.95(1H, s). ESI(+): 362 |
| 144 | NMR: 1.49-2.03(5H, m), 2.42(3H, s), 2.81-2.91(5H, m), 3.29(1H, brs), 4.69(1H, brs), 6.53(2H, s), 6.83(1H, brs), 7.29(1H, t, J = 7.3 Hz), 7.4(2H, t, J = 7.7 Hz), 7.47-7.49(2H, m), 9.07(1H, brs). ESI(+): 343 |
| 145 | NMR: 1.56-1.62(6H, m), 3.17-3.23(6H, m), 3.83(2H, s), 7.28-7.34(1H, m), 7.38-7.44(2H, m), 9.16(1H, s), 9.76(1H, brs), 10.35(1H, brs). ESI: (+)380 |
| 146 | NMR: 1.56-1.61(6H, m), 3.17-3.22(6H, m), 3.82(2H, s), 7.27-7.35 (2H, m), 7.44-7.51(1H, m), 9.16(1H, s), 9.80(1H, brs), 10.30(1H, brs). ESI: (+)380 |
| 147 | NMR: 1.18-1.26(1H, m), 1.33-1.42(1H, m), 1.46-1.59(3H, m), 1.72-1.82(1H, m), 2.13-2.19(1H, m), 2.58-2.72(4H, m), 2.74-2.82(1H, m), 3.87(1H, dd, J = 10.8, 6.4 Hz), 3.97(1H, dd, J = 10.8, 9.2 Hz), 7.27-7.41(3H, m), 9.13(1H, s), 9.64(1H, brs). ESI(+): 380 |
| 148 | NMR: 1.56-1.89(5H, m), 2.18-2.26(1H, m), 2.71-2.78(1H, m), 3.07-3.21(4H, m), 3.24-3.32(1H, m), 3.97(1H, dd, J = 11.2, 7.2 Hz), 4.07(1H, dd, J = 11.2, 8.8 Hz), 7.26-7.34(2H, m), 7.45-7.52(1H, m), 9.16(1H, s), 9.79(1H, brs), 10.20(1H, brs). ESI(+): 380 |
| 149 | NMR: 2.08-2.15(6H, m), 3.30-3.37(6H, m), 7.28-7.42(3H, m), 9.14(1H, s), 9.81(1H, brs), 10.46(1H, brs). ESI(+): 366 |
| 150 | NMR: 2.08-2.14(6H, m), 3.31-3.35(6H, m), 7.25-7.32(2H, m), 7.44-7.51(1H, m), 9.15(1H, s), 9.85(1H, brs), 10.51(1H, brs). ESI(+): 366 |
| 151 | NMR: 1.67-1.96(4H, m), 2.11-2.16(1H, m), 2.90-2.96(1H, m), 3.03-3.28(4H, m), 3.54-3.62(1H, m), 4.80-4.84(1H, m), 7.28-7.35(1H, m), 7.38-7.44(2H, m), 9.17(1H, s), 9.93(1H, brs), 10.51(1H, brs). ESI(+): 366 |
| 152 | NMR: 1.67-1.95(4H, m), 2.11-2.16(1H, m), 2.88-2.95(1H, m), 3.03-3.28(4H, m), 3.54-3.61(1H, m), 4.78-4.83(1H, m), 7.27-7.38(2H, m), 7.45-7.52(1H, m), 9.18(1H, s), 9.96(1H, brs), 10.48(1H, brs). ESI(+): 366 |
| 153 | NMR: 1.40-1.76(6H, m), 3.11-3.25(6H, m), 3.88(2H, s), 7.50-7.68(5H, m), 10.11(1H, s), 10.38(1H, brs). ESI(+): 345 |
| 154 | NMR: 1.50-1.82(5H, m), 2.14(1H, m), 2.59-2.64(1H, m), 2.96-3.07(4H, m), 3.15-3.20(1H, m), 3.96-4.09(2H, m), 6.47(2H, s), 7.28-7.32(2H, m), 7.56-7.59(2H, m), 9.00(1H, m), 9.46(1H, s). ESI(+): 362 |

TABLE 53

| Ex | data |
|---|---|
| 155 | NMR: 1.58(6H, br), 3.20(6H, br), 3.84(2H, s), 7.30-7.34(2H, m), 7.57-7.61(2H, m), 9.01(1H, s), 9.48(1H, s), 10.18(1H, br). ESI(+): 362 |

TABLE 53-continued

| Ex | data |
|---|---|
| 156 | NMR: 2.14(6H, br), 3.35-3.37(6H, br), 7.28-7.34(2H, m), 7.53-7.58(2H, m), 8.99(1H, s), 9.51(1H, br), 10.35(1H, br). ESI(+): 348 |
| 157 | NMR: 1.54-1.58(6H, m), 3.17-3.21(6H, m), 3.8(2H, s), 7.27-7.36(2H, m), 7.43-7.48(1H, m), 7.52-7.55(1H, m), 9.12(1H, s), 9.6(1H, brs), 10.09(1H, brs). ESI(+): 362 |
| 158 | NMR: 1.42-1.72(4H, m), 1.96(1H, br), 2.66(1H, br), 2.76-2.93(4H, m), 3.26-3.31(1H, m), 4.68-4.70(1H, m), 6.53(2H, s), 7.29-7.33(2H, m), 7.58-7.60(2H, m), 9.00(1H, s), 9.52(1H, s). ESI(+): 348 |
| 159 | NMR: 1.58-1.64(1H, m), 1.74-1.84(4H, m), 2.19-2.23(1H, m), 2.73-2.78(1H, m), 3.12-3.3(5H, m), 3.94-4.07(2H, m), 7.27-7.36(2H, m), 7.43-7.49(1H, m), 7.53(1H, dt, J = 1.6, 7.7 Hz), 9.11(1H, s), 9.6(1H, brs), 9.91(1H, brs). ESI(+): 362 |
| 160 | NMR: 1.39(6H, m), 2.92(6H, m), 3.76(2H, s), 6.42(1H, s), 7.24(1H, dt, J = 8.8 Hz, 2.6 Hz), 7.37-7.43(2H, m), 7.48-7.53(1H, m), 9.04(1H, s), 9.51 (1H, br). ESI(+): 362 |
| 161 | NMR: 1.54-1.58(6H, m), 3.16-3.2(6H, m), 3.85(2H, s), 7.48-7.55(3H, m), 7.64-7.65(2H, m), 9.85(1H, s), 10.03(1H, brs). ESI(+): 412 |
| 162 | NMR: 1.3-1.7(5H, m), 1.9-2.0(1H, m), 2.3-2.4(1H, m), 2.7-3.0(5H, m), 3.9-4.1(2H, m), 6.41(1H, s), 7.23(1H, dt, J = 8.8 Hz, 2.5 Hz), 7.35-7.40(2H, m), 7.46-7.52(1H, m), 9.03(1H, s), 9.50(1H, brs). ESI(+): 362 |
| 163 | NMR: 1.56-1.6(6H, m), 3.19-3.23(6H, m), 3.81(2H, s), 7.21(1H, dt, J = 2.3, 8.4 Hz), 7.38-7.44(1H, m), 7.56(1H, dt, J = 6.5, 8.6 Hz), 9.12(1H, s), 9.64(1H, brs), 9.83(1H, brs). ESI(+): 380 |
| 164 | NMR: 1.47-1.69(4H, m), 1.96(1H, m), 2.61-2.93(5H, m), 3.27(1H, m), 4.68(1H, m), 6.56(2H, s), 7.19-7.25(1H, m), 7.37-7.42(2H, m), 7.47-7.53(1H, m), 9.04(1H, s), 9.60(1H, br). ESI(+): 348 |
| 165 | NMR: 1.59-1.65(1H, m), 1.74-1.85(4H, m), 2.2-2.24(1H, m), 2.74-2.78(1H, m), 3.13-3.32(5H, m), 3.94-4.08(2H, m), 7.21 (2H, dt, J = 2.3, 8.3 Hz), 7.38-7.44(1H, m), 7.55(1H, dt, J = 6.5, 8.6 Hz), 9.12(1H, s), 9.64(1H, brs), 9.93(1H, brs). ESI(+): 380 |
| 166 | NMR: 1.72-1.89(4H, m), 2.14(1H, brs), 2.94(1H, d, J = 13.2 Hz), 3.09-3.24(4H, m), 3.55-3.61(1H, m), 4.79-4.81(1H, m), 7.21(1H, dt, J = 2.5, 8.5 Hz), 7.38-7.44(1H, m), 7.58(1H, dt, J = 6.5, 8.5 Hz), 9.13(1H, s), 9.82(1H, brs), 10.24(1H, brs). ESI(+): 366 |
| 167 | NMR: 2.08-2.11(6H, m), 3.32-3.35(6H, m), 7.2(1H, dt, J = 2.4, 8.6 Hz), 7.36-7.42(1H, m), 7.53(1H, dt, J = 6.5, 8.6 Hz), 9.11(1H, s), 9.68(1H, brs), 10(1H, brs). ESI(+): 366 |

TABLE 54

| Ex | data |
|---|---|
| 168 | NMR: 1.59-1.62(6H, m), 3.19-3.23(6H, m), 3.87(2H, s), 7.29-7.33(3H, m), 9.09(1H, s), 9.68(1H, brs), 9.91(1H, brs), ESI(+): 380 |
| 169 | NMR: 2.17(6H, brs), 3.34-3.39(6H, m), 7.44-7.49(3H, m), 7.58-7.58(1H, m), 9.04(1H, s), 9.64(1H, brs), 10.2(1H, brs), ESI(+): 364 |
| 170 | NMR: 1.59-1.65(1H, m), 1.75-1.91(4H, m), 2.24-2.28(1H, m), 2.77(1H, dd, J = 6.5, 13 Hz), 3.14-3.17(4H, m), 3.27-3.29(1H, m), 4-4.14(2H, m), 7.28-7.34(3H, m), 9.08(1H, s), 9.68(1H, brs), 9.97(1H, brs). ESI(+): 380 |
| 171 | NMR: 1.73-1.91(4H, m), 2.16(1H, brs), 2.93-3.23(5H, m), 3.57-3.63(1H, m), 4.85-4.87(1H, m), 7.44-7.51(3H, m), 7.61(1H, brs), 9.07(1H, s), 9.79(1H, brs), 10.47(1H, brs). ESI(+): 364 |
| 172 | NMR: 2.14-2.18(6H, m), 3.35-3.39(6H, m), 7.24-7.33(3H, m), 9.08(1H, s), 9.72(1H, brs), 10.06(1H, brs). ESI(+): 366 |
| 173 | NMR: 1.48-1.64(6H, m), 3.13-3.22(6H, m), 3.84(2H, s), 5.67(2H, d, J = 46.9 Hz), 7.38-7.60(5H, m), 9.56(1H, s), 10.05(1H, brs). ESI(+): 376 |
| 174 | NMR: 1.74-1.91(4H, m), 2.17(1H, brs), 2.98-3.24(5H, m), 3.59-3.64(1H, m), 4.86-4.89(1H, m), 7.29-7.33(3H, m), 9.1(1H, s), 9.85(1H, brs), 10.22(1H, brs). ESI(+): 366 |
| 175 | NMR: 1.62-2.20(5H, m), 2.80-3.64(6H, m), 4.80-4.88(1H, m), 5.67(2H, d, J = 47.2 Hz), 7.38-7.62(5H, m), 9.76(1H, s), 10.45(1H, brs). ESI(+): 362 |
| 176 | NMR: 1.58-1.61(6H, m), 3.18-3.22(6H, m), 3.86(2H, s), 7.44-7.51(3H, m), 7.63(1H, brs), 9.06(1H, s), 9.61(1H, brs), 10.26(1H, brs). ESI(+): 378 |
| 177 | NMR: 1.48-1.62(6H, m), 3.12-3.22(6H, m), 3.85(2H, s), 7.36(1H, t, J = 54.2 Hz), 7.43-7.65(5H, m), 9.71(1H, s), 10.32(1H, brs). ESI(+): 394 |
| 178 | NMR: 1.61(1H, brs), 1.74-1.86(4H, m), 2.24(1H, brs), 2.75-2.79(1H, m), 3.15-3.2(4H, m), 3.26-3.29(1H, m), 3.99-4.13(2H, m), 7.44-7.5(3H, m), 7.61(1H, brs), 9.05(1H, s), 9.61(1H, brs), 9.89(1H, brs). ESI(+): 378 |

TABLE 54-continued

| Ex | data |
|---|---|
| 179 | NMR: 1.60-2.20(5H, m), 2.80-3.26(5H, m), 3.50-3.62(1H, m), 4.81-4.87(1H, m), 7.36(1H, t, J = 54.2 Hz), 7.42-7.65(5H, m), 9.91(1H, s), 10.66(1H, brs). ESI(+): 380 |
| 180 | ESI(+): 396 |
| 181 | ESI(+): 344 |
| 182 | ESI(+): 396 |
| 183 | ESI(+): 382 |
| 184 | ESI(+): 345 |
| 185 | ESI(+): 412 |
| 186 | ESI(+): 358 |
| 187 | ESI(+): 398 |
| 188 | ESI(+): 358 |
| 189 | ESI(+): 398 |

TABLE 55

| Ex | data |
|---|---|
| 190 | ESI(+): 358 |
| 191 | ESI(+): 412 |
| 192 | ESI(+): 380 |
| 193 | ESI(+): 382 |
| 194 | ESI(+): 366 |
| 195 | ESI(+): 396 |
| 196 | ESI(+): 366 |
| 197 | ESI(+): 378 |
| 198 | ESI(+): 380 |
| 199 | ESI(+): 378 |
| 200 | ESI(+): 396 |
| 201 | ESI(+): 364 |
| 202 | ESI(+): 382 |
| 203 | ESI(+): 350 |
| 204 | ESI(+): 360 |
| 205 | ESI(+): 350 |
| 206 | ESI(+): 360 |
| 207 | ESI(+): 376 |
| 208 | ESI(+): 344 |
| 209 | ESI(+): 376 |
| 210 | ESI(+): 358 |
| 211 | ESI(+): 362 |
| 212 | ESI(+): 380 |
| 213 | ESI(+): 362 |
| 214 | ESI(+): 366 |
| 215 | ESI(+): 424 |
| 216 | ESI(+): 344 |
| 217 | ESI(+): 410 |
| 218 | ESI(+): 355 |
| 219 | ESI(+): 396 |
| 220 | ESI(+): 369 |
| 221 | ESI(+): 348 |
| 222 | ESI(+): 369 |
| 223 | ESI(+): 334 |
| 224 | ESI(+): 380 |
| 225 | ESI(+): 387 |
| 226 | ESI(+): 396 |
| 227 | ESI(+): 336 |
| 228 | ESI(+): 387 |

TABLE 56

| Ex | data |
|---|---|
| 229 | ESI(+): 387 |
| 230 | ESI(+): 373 |
| 231 | ESI(+): 398 |
| 232 | ESI(+): 373 |
| 233 | ESI(+): 398 |
| 234 | ESI(+): 387 |
| 235 | ESI(+): 366 |
| 236 | ESI(+): 413 |
| 237 | ESI(+): 345 |
| 238 | ESI(+): 413 |
| 239 | ESI(+): 346 |

TABLE 56-continued

| Ex | data |
|---|---|
| 240 | ESI(+): 384 |
| 241 | ESI(+): 384 |
| 242 | ESI(+): 370 |
| 243 | NMR: 1.50-1.57(6H, m), 3.14-3.20(6H, m), 3.78(2H, s), 7.29-7.46(9H, m), 8.77(1H, s), 10.26(1H, brs). ESI(+): 337 |
| 244 | ESI(+): 351 |
| 245 | ESI(+): 336 |
| 246 | NMR: 1.47-1.81(5H, m), 2.03-2.13(1H, m), 2.54-2.61(1H, m), 2.91-3.17(5H, m), 3.89-4.04(2H, m), 6.47(2H, s), 7.27-7.45(9H, m), 8.76(1H, s). ESI(+): 337 |
| 247 | ESI(+): 362 |
| 248 | ESI(+): 336 |
| 249 | ESI(+): 362 |
| 250 | NMR: 1.57-2.00(8H, m), 2.67-2.76(1H, m), 3.02-3.21(4H, m), 3.24-3.32(1H, m), 3.98(2H, t, d = 8.0 Hz), 7.36-7.41(1H, m), 7.44-7.48(2H, m), 7.54-7.57(2H, m), 9.01(1H, s), 9.41(1H, brs), 10.25(1H, brs). ESI(+): 358 |
| 251 | NMR: 1.41-1.70(4H, m), 2.28-2.32(1H, m), 2.62-2.82(4H, m), 3.27-3.40(2H, m), 4.39-4.50(1H, m), 4.39-4.50(1H, m), 5.18(1H, brs), 7.35-7.47(3H, m), 7.52-7.56(2H, m), 8.98-9.00(1H, m), 9.33-9.39(1H, m), ESI(+): 356 |
| 252 | NMR: 1.44-1.65(8H, m), 3.13-3.20(6H, m), 3.98-4.03(2H, m), 7.35-7.48(3H, m), 7.53-7.57(2H, m), 8.99(1H, s), 9.35(1H, s), 10.20(1H, s). ESI(+): 358 |
| 253 | NMR: 1.79-2.38(6H, m), 3.09-3.53(6H, m), 7.36-7.55(5H, m), 9.01(1H, s), 9.67(1H, s), 11.06(1H, s). ESI(+): 330 |
| 254 | NMR: 1.87(2H, brs), 2.82-3.33(6H, m), 3.59-3.64(2H, m), 5.01-5.04(1H, m), 7.37-7.41(1H, m), 7.45-7.49(2H, m), 7.54-7.57(2H, m), 9.02(1H, s), 9.73(1H, s), 10.33(1H, brs). ESI(+): 316 |
| 255 | NMR: 1.69-1.96(4H, m), 2.57(1H, b.s), 3.19-3.33(6H, m), 4.76-4.81(1H, m), 7.36-7.4(1H, m), 7.43-7.47(2H, m), 7.53-7.55(2H, m), 9(1H, s), 9.51(1H, s), 10.57(1H, brs), ESI(+): 330 |

TABLE 57

| Ex | data |
|---|---|
| 256 | ESI(+): 387 |
| 257 | NMR: 1.57(6H, brs), 3.14-3.20(6H, m), 3.49(2H, t, d = 5.2 Hz), 3.61 (2H, t, d = 5.2 Hz), 3.83(2H, s), 4.53(2H, s), 5.71(1H, brs), 7.22-7.43 (10H, m), 8.42(1H, brs), 9.25(1H, s), 10.32(1H, s). ESI(+): 493 |
| 258 | NMR: 1.57(6H, brs), 1.84-1.91(2H, m), 2.67(2H, t, d = 7.2 Hz), 3.17 (6H, brs), 3.26(2H, t, d = 7.2 Hz), 3.83(2H, s), 4.72(1H, brs), 7.17-7.43(10H, m), 8.50(1H, brs), 9.26(1H, s), 10.32(1H, s). ESI(+): 477 |
| 259 | NMR: 2.04(2H, brs), 2.18(2H, brs), 3.41(4H, brs), 3.52(2H, brs), 7.37-7.41(1H, m), 7.44-7.48(2H, m), 7.53-7.55(2H, m), 9.02(1H, s), 9.82(1H, s), 10.61(1H, s). ESI(+): 316 |
| 260 | NMR: 1.6(2H, brs), 1.82(2H, brs), 2.89(2H, brs), 3.29(4H, brs), 4.27(2H, s), 7.37-7.4(1H, m), 7.45-7.48(2H, m), 7.55-7.58(2H, m), 9.02(1H, s), 9.54(1H, s), 10.24(1H, s), ESI(+): 330 |
| 261 | NMR: 1.55-1.64(6H, m), 3.17-3.24(6H, m), 3.87(2H, s), 7.38(1H, t, J = 54 Hz), 7.52-7.58(3H, m), 7.69-7.71(1H, m), 9.85(1H, s), 10.23(1H, s). ESI(+): 428 |
| 262 | NMR: 1.46-2.4(6H, m), 2.86-3.38(6H, m), 3.83-4.17(2H, m), 7.36-7.4(1H, m), 7.44-7.47(2H, m), 7.54-7.56(2H, m), 9(0.6H, s), 9.01(0.4H, s), 9.44(0.6H, brs), 9.47(0.4H, brs), 10.32(0.4H, brs), 10.41(0.6H, brs): 344 |
| 263 | NMR: 1.65(3H, brs), 1.89(1H, brs), 2.58(1H, brs), 3.11-3.27(4H, m), 3.69-3.76(1H, m), 5.16-5.21(1H, m), 7.37-7.41(1H, m), 7.45-7.48 (2H, m), 7.56-7.58(2H, m), 9.02(1H, s), 9.7(1H, brs), 10.26(1H, brs). ESI(+): 330 |
| 264 | NMR: 1.6-1.68(3H, m), 1.86(1H, brs), 2.33-2.4(1H, m), 2.7(1H, brs), 3.05-3.26(4H, m), 4.14-4.23(2H, m), 7.36-7.4(1H, m), 7.44-7.48(2H, m), 7.54-7.56(2H, m), 9.00(1H, s), 9.48(1H, brs), 10.09(1H, brs). ESI(+): 344 |
| 265 | NMR: 1.53-1.63(6H, m), 1.79(2H, brs), 3.18-3.26(6H, m), 3.74(2H, s), 7.36-7.4(1H, m), 7.44-7.48(2H, m), 7.55-7.57(2H, m), 9.01(1H, s), 9.44(1H, brs), 10.58(1H, brs). ESI(+): 358 |
| 266 | NMR: 1.5-2.1(8H, m), 2.97-3.24(6H, m), 4.00(2H, m), 6.49(2H, s), 7.38(1H, m), 7.45(2H, m), 7.55(2H, m), 9.00(1H, s), 9.42(1H, brs). ESI(+): 358 |

TABLE 57-continued

| Ex | data |
|---|---|
| 267 | NMR: 1.5-1.9(7H, m), 3.0-3.2(6H, m), 4.90(1H, m), 6.52(2H, s), 7.37(1H, s), 7.44(2H, m), 7.55(2H, m), 9.00(1H, s), 9.47(1H, brs). ESI(+): 344 |
| 268 | NMR: 1.73-1.83(6H, m), 2.79-2.86(6H, m), 7.35(1H, t, J = 54 Hz), 7.50-7.53(3H, m), 7.64-7.65(1H, m), 9.57(1H, s). ESI(+): 414 |
| 269 | NMR: 1.49-1.66(4H, m), 2.03-2.10(2H, m), 2.18-2.30(2H, m), 2.73-2.94(6H, m), 7.42-7.50(3H, m), 7.58-7.60(1H, m), 9.01 (1H, s), 9.27(1H, s). ESI(+): 378 |
| 270 | NMR: 1.17-1.27(1H, m), 1.41-1.68(3H, m), 1.84-1.98(1H, m), 2.10-2.16(1H, m), 2.28-2.37(2H, m), 2.48-2.73(4H, m), 3.68-3.76(2H, m), 7.35-7.57(5H, m), 8.99(1H, s), 9.35(1H, s). ESI(+): 344 |

The compounds of A1 to A32 shown in Tables 58 to 60 below were prepared in the same manner as in Production Examples and Examples above, each using corresponding starting materials.

TABLE 58

| No | Structure |
|---|---|
| A1 | (structure) |
| A2 | (structure) |
| A3 | (structure) |

TABLE 58-continued

| No | Structure |
|---|---|
| A4 | 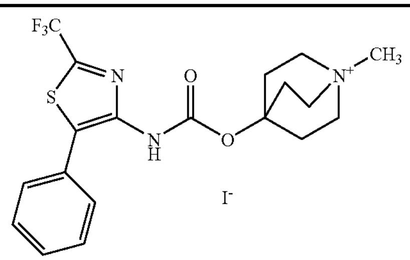 |
| A5 | 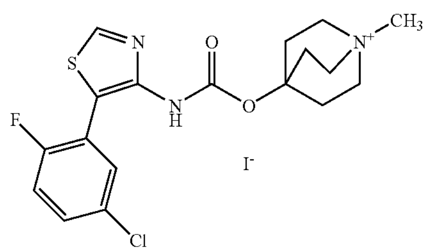 |
| A6 | 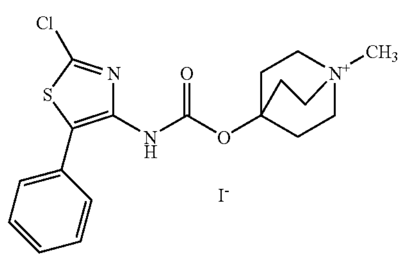 [SMILES: C[N+]12CCC(OC(=O)Nc3nc(C(F)(F)F)sc3-c3ccccc3)(CC1)CC2 ; [I-]] |
| A7 | 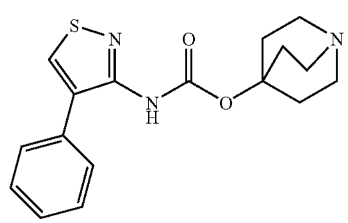 [SMILES: O=C(Nc1nscc1-c1ccccc1)OC12CCN(CC1)CC2] |
| A8 | 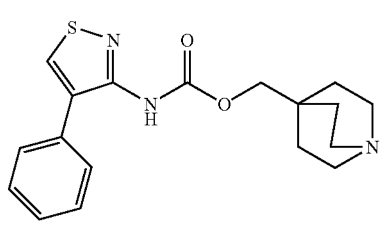 [SMILES: O=C(Nc1nscc1-c1ccccc1)OCC12CCN(CC1)CC2] |
| A9 | 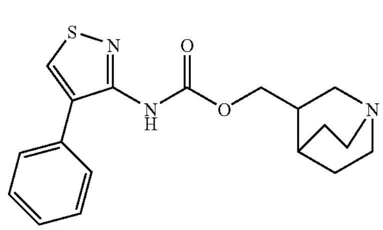 [SMILES: O=C(Nc1nscc1-c1ccccc1)OCC1CN2CCC1CC2] |
| A10 | 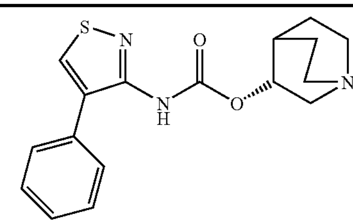 |

TABLE 59

| No | Structure |
|---|---|
| A11 | 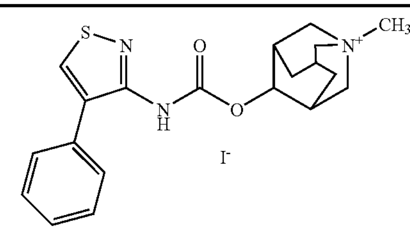 |
| A12 | 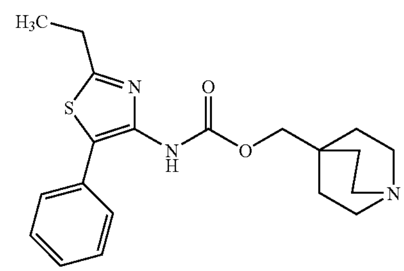 [SMILES: CCc1nc(NC(=O)OCC23CCN(CC2)CC3)c(-c2ccccc2)s1] |
| A13 | 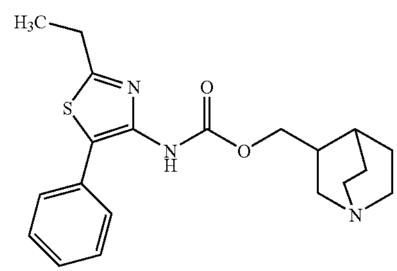 [SMILES: CCc1nc(NC(=O)OCC2CN3CCC2CC3)c(-c2ccccc2)s1] |
| A14 | 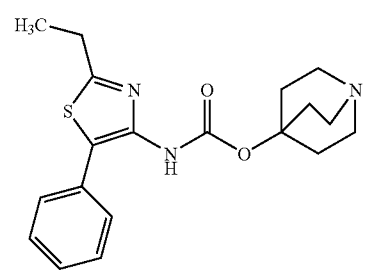 [SMILES: CCc1nc(NC(=O)OC23CCN(CC2)CC3)c(-c2ccccc2)s1] |

TABLE 59-continued

| No | Structure |
|---|---|
| A15 | (structure) |
| A16 | (structure) |
| A17 | (structure) |
| A18 | (structure) |
| A19 | (structure) |
| A20 | (structure) |

TABLE 60

| No | Structure |
|---|---|
| A21 | (structure) |
| A22 | (structure) |
| A23 | (structure) |
| A24 | (structure) |

INDUSTRIAL AVAILABILITY

The compound of the formula (I) or a salt thereof has an antagonistic action on the binding of a muscarinic $M_3$ receptor, and can be therefore used as a prophylactic and/or therapeutic agent for an inflammatory disease such as chronic obstructive pulmonary disease (COPD), asthma and the like.

The invention claimed is:

1. A compound of formula (I) or a salt thereof:

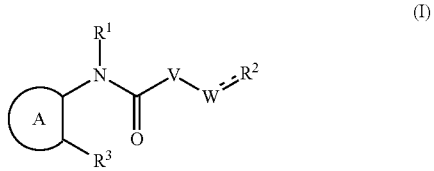

(I)

in which $R^1$ is —H;

$R^2$ is an aza-bridged-ring selected from the group consisting of the formulae (a) and (b), wherein the ring carbon in the aza-bridged-ring may be substituted with one or more $R^{22}$:

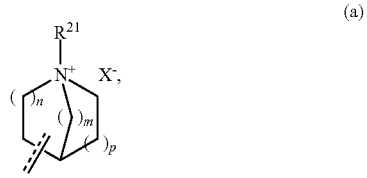

(a)

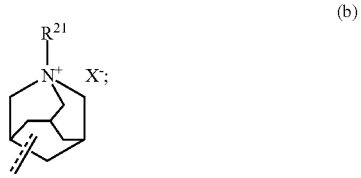

(b)

m, n, and p are independently 1 or 2;

$R^{21}$ is $C_{1-6}$ alkyl, —$C_{1-6}$ alkyl-O-phenyl, or —$C_{1-6}$ alkyl-phenyl;

$R^{22}$ is —$C_{1-6}$ alkyl-cycloalkyl or —$C_{1-6}$ alkyl-aryl;

R³ is phenyl which may be substituted with one or more R³¹;

R³¹ is halogen, —OH, —CN, —CF₃, $C_{1-6}$ alkyl or —O—$C_{1-6}$ alkyl;

Ring A is thiazole which may be substituted with one or more $R^A$;

$R^A$ is halogen, —CN, —NH₂, $C_{1-6}$ alkyl, —O—$C_{1-6}$ alkyl, —CONH₂, —NH—$C_{1-6}$ alkyl, —NH—$C_{1-6}$ alkyl-O—$C_{1-6}$-phenyl, —NH—$C_{1-6}$ alkyl-phenyl, or —NH—$C_{1-6}$ alkyl-OH, in which $C_{1-6}$ alkyl may be substituted with one or more halogen;

V is —NH— or —O—;

W is —(CH₂)$_q$— or —(CH₂)$_n$—CH=;

q is 0, 1, or 2;

s is 1 or 2;

X⁻ is a counter anion; and

═ is a single bond or a double bond.

2. The compound or salt thereof as described in claim 1, which is 4-({[5-(3-chlorophenyl)-1,3-thiazol-4-yl]carbamoyl}oxy)-1-methyl-1-azoniabicyclo[2.2.2]octane iodide, 1-(2-phenylethyl)-4-{[(5-phenyl-1,3-thiazol-4-yl)carbamoyl]oxy}-1-azoniabicyclo[2.2.2]octane bromide, 1-(2-phenoxyethyl)-4-{[(5-phenyl-1,3-thiazol-4-yl)carbamoyl]oxy}-1-azoniabicyclo[2.2.2]octane bromide, 4-({[5-(2,5-difluorophenyl)-1,3-thiazol-4-yl]carbamoyl}oxy)-1-methyl-1-azoniabicyclo[2.2.2]octane iodide, 1-methyl-5-{[(5-phenyl-1,3-thiazol-4-yl)carbamoyl]oxy}-1-azoniabicyclo[3.2.2]nonane iodide, 4-({[5-(3-chlorophenyl)-1,3-thiazol-4-yl]carbamoyl}oxy)-1-(2-phenoxyethyl)-1-azoniabicyclo[2.2.2]octane iodide, 4-({[5-(3-chlorophenyl)-1,3-thiazol-4-yl]carbamoyl}oxy)-1-methyl-1-azoniabicyclo[2.2.2]octane bromide, 4-({[5-(3,5-dichlorophenyl)-1,3-thiazol-4-yl]carbamoyl}oxy)-1-methyl-1-azoniabicyclo[2.2.2]octane iodide, 4-({[5-(2,5-difluorophenyl)-1,3-thiazol-4-yl]carbamoyl}oxy)-1-methyl-1-azoniabicyclo [2.2.2]octane bromide, 4-({[5-(2,4-difluorophenyl)-1,3-thiazol-4-yl]carbamoyl}oxy)-1-methyl-1-azoniabicyclo [2.2.2]octane bromide, 1 methyl-4-{[(5-phenyl-1,3-thiazol-4-yl)carbamoyl]oxy}-1-azoniabicyclo[2.2.2]octane bromide, 4 ({[5-(3,5-dichlorophenyl)-1,3-thiazol-4-yl]carbamoyl}oxy)-1-methyl-1-azoniabicyclo [2.2.2]octane bromide, or 1-methyl-5-{[(5-phenyl-1,3-thiazol-4-yl)carbamoyl]oxy}-1-azoniabicyclo[3.2.2]nonane bromide.

3. The compound or a salt thereof as described in claim 1, which is

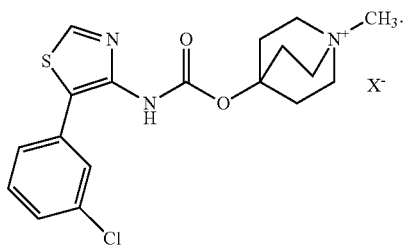

4. The compound or a salt thereof as described in claim 1, which is

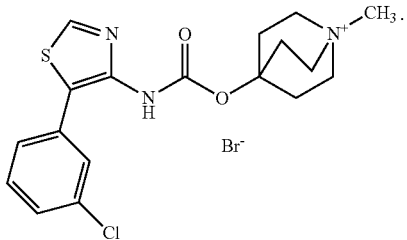 [SMILES: C[N+]12CCC(OC(=O)Nc3ncsc3-c3cccc(Cl)c3)(CC1)CC2 ; [Br-]]

5. A pharmaceutical composition comprising the compound or a salt thereof as described in claim 1, and a pharmaceutically acceptable excipient.

6. A method for treating chronic obstructive pulmonary disease or asthma, comprising administering to a patient an effective amount of the compound or a salt thereof as described in claim 1.

* * * * *

UNITED STATES PATENT AND TRADEMARK OFFICE
CERTIFICATE OF CORRECTION

PATENT NO. : 8,367,696 B2
APPLICATION NO. : 12/524758
DATED : February 5, 2013
INVENTOR(S) : Shinya Nagashima et al.

It is certified that error appears in the above-identified patent and that said Letters Patent is hereby corrected as shown below:

ON THE TITLE PAGE, ITEM (56) FOREIGN PATENT DOCUMENTS:

"JP 08198751 * 8/1996" should be deleted; and
"WO WO97/30998  8/1997" should read --WO  97/30998  8/1997--.

In the Specifications:

COLUMN 1:

Line 61, "pathetic." should read --pathetic nervous system.--.

COLUMN 5:

Line 54, "oxalzole," should read --oxazole,--.

COLUMN 8:

Line 2, close up right margin;
Line 3, close up left margin; and
Line 44, "thereof" should read --thereof.--.

COLUMN 10:

Line 23, "NB S:" should read --NBS:--.

COLUMN 11:

Line 30, "(1-a)" should read --(I-a)--; and
Line 39, "an" should read --a--.

Signed and Sealed this
Twenty-eighth Day of May, 2013

Teresa Stanek Rea
*Acting Director of the United States Patent and Trademark Office*

COLUMN 13:
Line 9, "Pd₂ dba₃" should read --Pd$_2$dba$_3$--.
COLUMN 14:
Line 28, "(1-c)" should read --(I-c)--; and
Line 65, "(5-b)'" should read --(5-b)--.
COLUMN 20:
Line 55, "tively)" should read --tively).--.
COLUMN 22:
Line 15, "generally used" should read --generally-used--.
COLUMN 54:
Table 12, Pr 27, "ESI(+):        --ESI(+):
              339,     should read      399,
              241"                      341--.
COLUMN 56:
Table 13, Pr 36-1, " 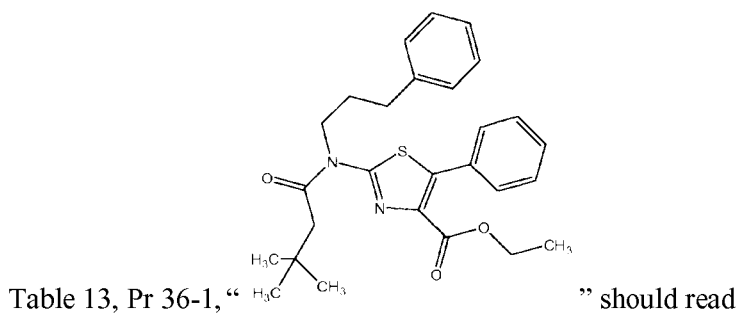 " should read
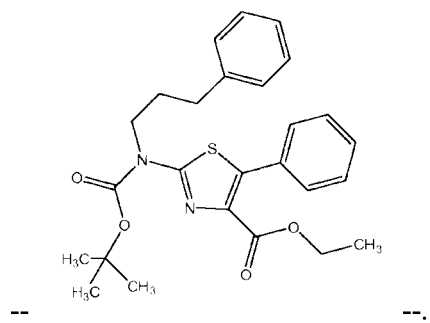
--.

CERTIFICATE OF CORRECTION (continued)

U.S. Pat. No. 8,367,696 B2

COLUMN 63:

Line 25, "A" should read --To a--.

COLUMN 69:

Ex 16, " 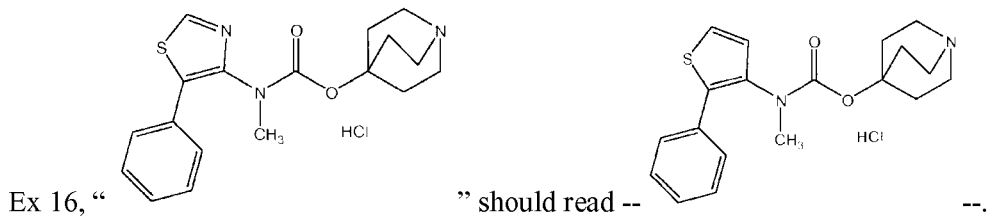 " should read -- --.

COLUMN 74:

Ex 41, " 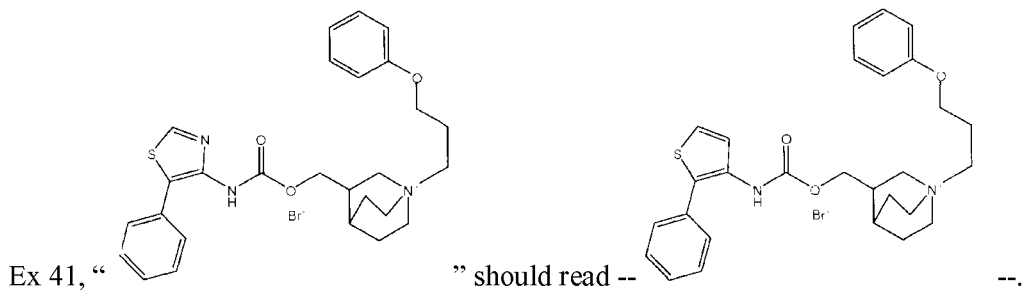 " should read -- --.

COLUMN 90:

Ex 128, " 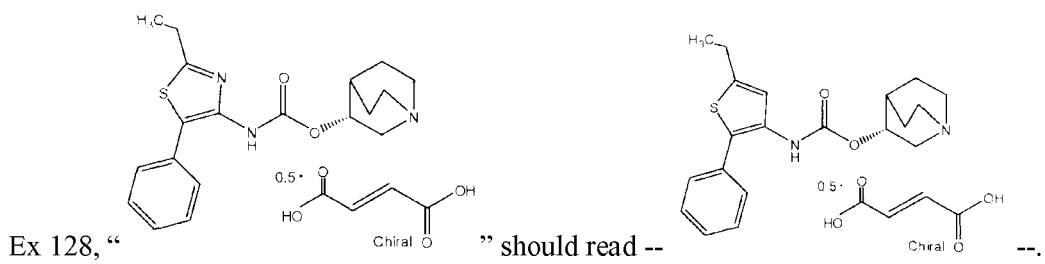 " should read -- --.

COLUMN 104:

Ex 213, " 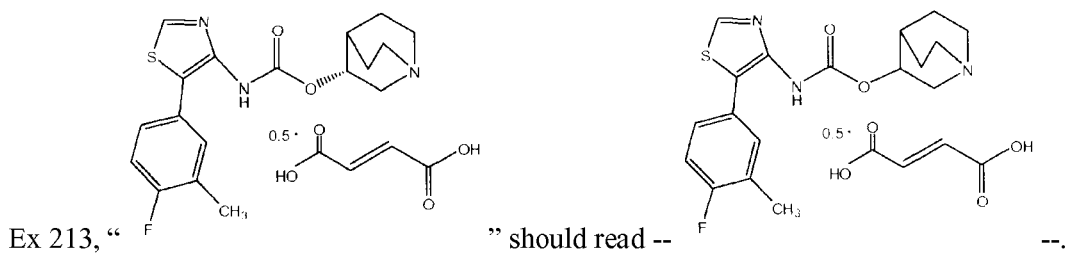 " should read -- --.

COLUMN 107:

Ex 229, " 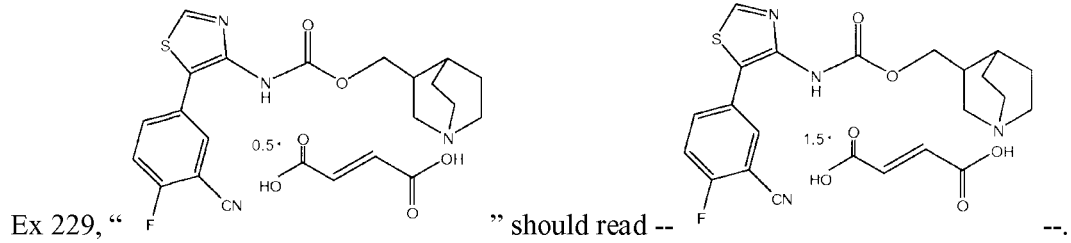 " should read -- --.

COLUMN 113:

Ex 268, " 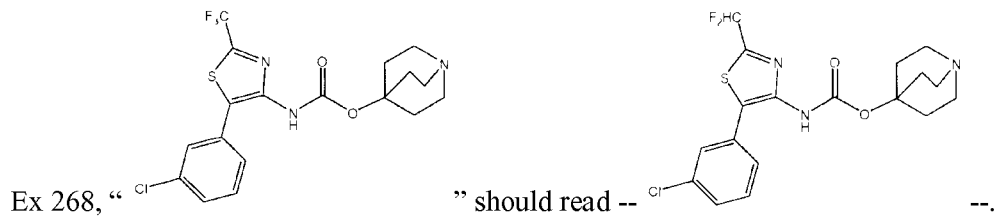 " should read -- --.

COLUMN 118:

Line 31, close up right margin; and
Line 40, close up right margin.

COLUMN 119:

Line 23, "[α]$^D_{26}$" should read --[α]$_D^{26}$--;
Lines 26-27, "(+):      should read    --( + ): 369--;
            369"
Line 30, "[α]$^D_{26}$" should read --[α]$_D^{26}$--;
Line 33, close up right margin; and
Line 53, close up right margin.

COLUMN 120:

Line 13, close up right margin;
Line 33, close up right margin; and
Line 38, close up right margin.

COLUMN 123:

Line 57, close up right margin.

CERTIFICATE OF CORRECTION (continued)
U.S. Pat. No. 8,367,696 B2

COLUMN 127:

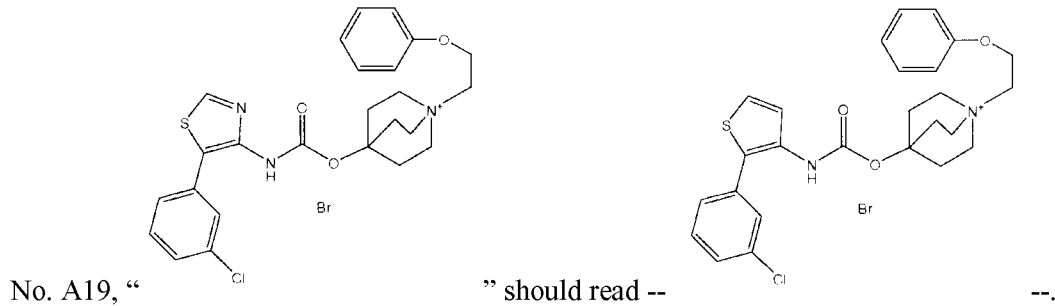

No. A19, " " should read -- --.

In the Claims:

COLUMN 131:

Line 14, "$-(CH_2)_n-CH=;$" should read -- $-(CH_2)_s-CH=;$ --.